US009119886B2

(12) United States Patent
Corti et al.

(10) Patent No.: US 9,119,886 B2
(45) Date of Patent: Sep. 1, 2015

(54) IMMUNOCONJUGATES FOR THE TREATMENT OF TUMOURS

(75) Inventors: Angelo Corti, Milan (IT); Flavio Curnis, Milan (IT)

(73) Assignee: MolMed SpA, Milan (IT)

(*) Notice: Subject to any disclaimer, the term of this patent is extended or adjusted under 35 U.S.C. 154(b) by 208 days.

(21) Appl. No.: 12/771,696

(22) Filed: Apr. 30, 2010

(65) Prior Publication Data

US 2010/0310506 A1 Dec. 9, 2010

Related U.S. Application Data

(62) Division of application No. 10/492,117, filed as application No. PCT/IB03/02187 on Apr. 30, 2003, now abandoned.

(30) Foreign Application Priority Data

Apr. 30, 2002 (GB) .................................. 0209896.0

(51) Int. Cl.
| | | |
|---|---|---|
| *A61K 38/19* | (2006.01) | |
| *A61K 47/42* | (2006.01) | |
| *A61K 47/48* | (2006.01) | |
| *C07K 14/525* | (2006.01) | |
| *C07K 14/57* | (2006.01) | |

(52) U.S. Cl.
CPC ......... *A61K 47/48423* (2013.01); *A61K 38/191* (2013.01); *A61K 47/48269* (2013.01); *A61K 47/48569* (2013.01); *C07K 14/525* (2013.01); *C07K 14/57* (2013.01); *C07K 2319/01* (2013.01)

(58) Field of Classification Search
None
See application file for complete search history.

(56) References Cited

U.S. PATENT DOCUMENTS

| | | | |
|---|---|---|---|
| 4,578,079 A | 3/1986 | Ruoslahti et al. | |
| 4,650,674 A | 3/1987 | Aggarwal et al. | |
| 4,791,101 A | 12/1988 | Adolf | |
| 4,879,237 A | 11/1989 | Rudslahti et al. | |
| 4,988,621 A | 1/1991 | Ruoslahti et al. | |
| 5,091,176 A | 2/1992 | Braatz et al. | |
| 5,114,711 A | 5/1992 | Bell et al. | |
| 5,120,829 A | 6/1992 | Pierschbacher et al. | |
| 5,169,930 A | 12/1992 | Ruoslahti et al. | |
| 5,180,811 A | 1/1993 | Doerper et al. | |
| 5,214,131 A | 5/1993 | Sano et al. | |
| 5,258,517 A | 11/1993 | Zepp et al. | |
| 5,264,209 A | 11/1993 | Mikayama et al. | |
| 5,498,694 A | 3/1996 | Ruoslahti | |
| 5,536,814 A | 7/1996 | Ruoslahti et al. | |
| 5,539,063 A | 7/1996 | Hakimi et al. | |
| 5,541,936 A | 7/1996 | Tanaka | |
| 5,580,853 A | 12/1996 | Sytkowski | |
| 5,587,456 A | 12/1996 | Pierschbacher et al. | |
| 5,612,311 A | 3/1997 | Pierschbacher et al. | |
| 5,648,330 A | 7/1997 | Pierschbacher et al. | |
| 5,650,150 A | 7/1997 | Gillies | |
| 5,672,585 A | 9/1997 | Pierschbacher et al. | |
| 5,700,908 A | 12/1997 | Ruoslahti | |
| 5,811,388 A | 9/1998 | Friend et al. | |
| 5,811,512 A | 9/1998 | Hirschmann et al. | |
| 5,888,814 A | 3/1999 | Kriegler et al. | |
| 5,891,418 A | 4/1999 | Sharma | |
| 6,180,084 B1 | 1/2001 | Ruoslahti et al. | |
| 6,576,239 B1 | 6/2003 | Ruoshiahti et al. | |
| 6,759,509 B1 | 7/2004 | King et al. | |
| 6,919,425 B2 | 7/2005 | Hong et al. | |
| 7,109,303 B2 | 9/2006 | Corti | |
| 7,150,869 B2 | 12/2006 | Corti | |
| 7,309,694 B2 | 12/2007 | Corti et al. | |
| 2003/0032164 A1 | 2/2003 | Wood et al. | |
| 2003/0077818 A1 | 4/2003 | Dickerson et al. | |
| 2003/0157056 A1 | 8/2003 | Corti | |
| 2004/0110933 A1 | 6/2004 | Rondon et al. | |
| 2005/0265965 A1 | 12/2005 | Corti | |
| 2006/0115451 A1 | 6/2006 | Corti | |
| 2007/0041939 A1 | 2/2007 | Corti | |

FOREIGN PATENT DOCUMENTS

| | | |
|---|---|---|
| EP | 0 239 400 | 9/1987 |
| EP | 0 251 494 | 1/1988 |
| EP | 0 396 387 | 11/1990 |
| EP | 0 496 074 | 7/1992 |
| EP | 1 149 913 | 10/2001 |
| EP | 1 217 070 | 6/2002 |
| WO | WO-90/10385 | 10/1990 |
| WO | WO-92/08495 | 5/1992 |
| WO | WO-95/15979 | 6/1995 |
| WO | WO-96/06641 | 3/1996 |
| WO | WO-96/36362 | 11/1996 |
| WO | WO-97/08203 | 3/1997 |
| WO | WO-98/10795 | 3/1998 |
| WO | WO-99/13329 | 3/1999 |

(Continued)

OTHER PUBLICATIONS

Curnis et al., Nat. Biotechnol., 2000, vol. 18:1185-1190.*
Aderka et al., Increased serum levels of soluble receptors for tumor necrosis factor in cancer patients, *Cancer Res.*, 51:5602-7 (1991).
Aderka et al., Shedding kinetics of soluble tumor necrosis factor (TNF) receptors after systemic TNF leaking during isolated limb perfusion. Relevance to the pathophysiology of septic shock, *J. Clin. Invest.*, 101(8):650-9 (1998).
Arap et al., Cancer treatment by targeted drug delivery to tumor vasculature in a mouse model, *Science*, 279(5349):377-80 (1998).
Asher et al., Murine tumor cells transduced with the gene for tumor necrosis factor-α, *J. Immunol.*, 146(9):3227-34 (1991).
Atkins et al., Phase I evaluation of intravenous recombinant human interleukin 12 in patients with advanced malignancies, *Clin. Cancer Res.* 3:409-17 (1997).
Balkwill et al., Human tumor xenografts treated with recombinant human tumor necrosis factor alone or in combination with interferons, *Cancer Res.*, 46:3990-3 (1986).
Barbara et al., Dissociation of TNF-α cytotoxic and proinflammatory activities by p55 receptor-and p75 receptor-selective TNF-α mutants, *EMBO J.*, 13(4):843-50 (1994).

(Continued)

*Primary Examiner* — Xiaozhen Xie
(74) *Attorney, Agent, or Firm* — Marshall, Gerstein & Borun LLP

(57) ABSTRACT

A pharmaceutical composition comprising a conjugate of a cytokine and a tumor targeting moiety (TTM) and a pharmaceutically acceptable excipient, wherein the cytokine is present in an amount which does not induce a negative feedback mechanism.

15 Claims, 10 Drawing Sheets

(56) References Cited

FOREIGN PATENT DOCUMENTS

Figure 1:
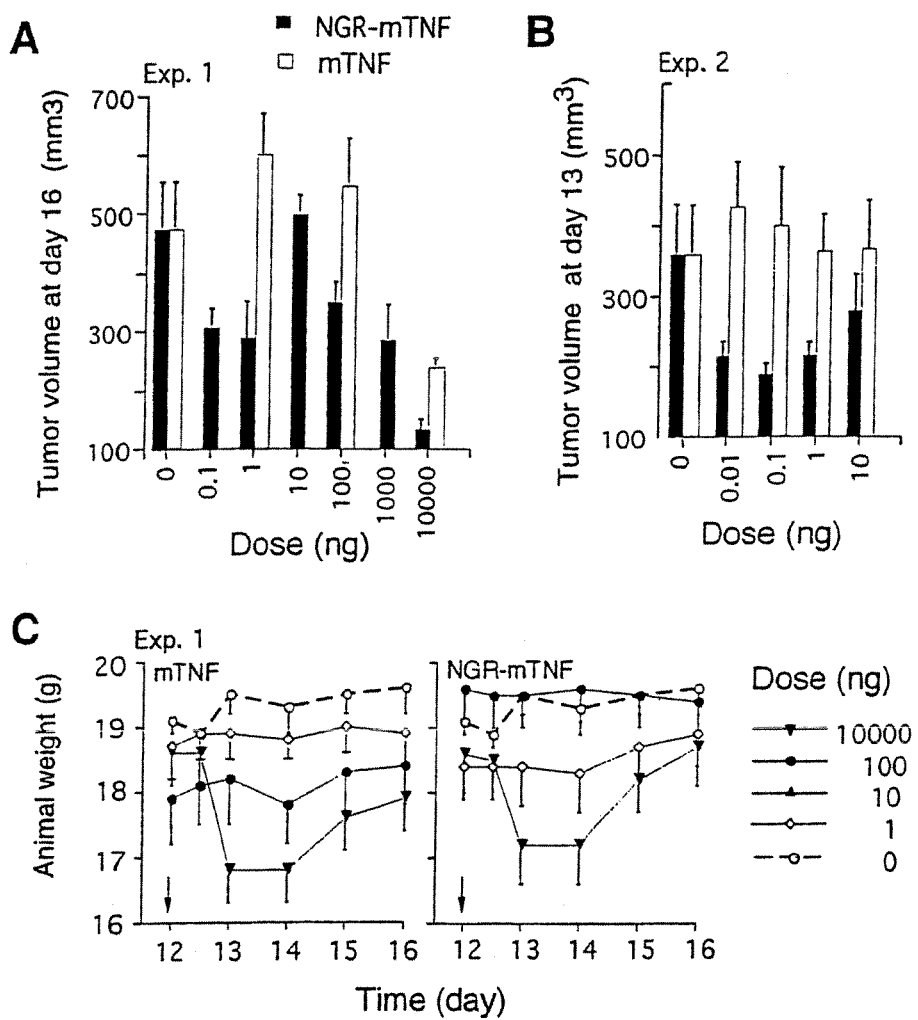

| | | |
|---|---|---|
| WO | WO-00/09143 | 2/2000 |
| WO | WO-01/61017 | 8/2001 |
| WO | WO 01/61017 A2 * | 8/2001 |
| WO | WO-01/62298 | 8/2001 |

OTHER PUBLICATIONS

Bartholeyns et al., Growing tumors induce hypersensitivity to endotoxin and tumor necrosis factor, *Infect. Immun.*, 55(9):2230-3 (1987).

Beyaert et al., Lithium chloride potentiates tumor necrosis factor-mediated cytotoxcity in vitro and in vivo, *Proc. Natl. Acad. Sci. USA*, 86(23):9494-8 (1989).

Beyaert et al., Sensitization of tumor cells to tumor necrosis factor action by the protein kinase inhibitor staurosporine, *Cancer Res.*, 53:2623-30 (1993).

Bigda et al., Dual role of the p75 tumor necrosis factor (TNF) receptor in TNF cytotoxicity, *J. Exp. Med.*, 180:445-60 (1994).

Borgia et al., Chemical synthesis of proteins, *Trends Biotechnol.*, 18:243-51 (2000).

Bregni et al., Human peripheral blood hematopoietic progenitors are optimal targets of retroviral-mediated gene transfer, *Blood*, 80(6):1418-22 (1992).

Brekken et al., Vascular endothelial growth factor as a marker of tumor endothelium, *Cancer Res.*, 58:1952-9 (1998).

Brett et al., Tumor necrosis factor/cachectin increases permeability of endothelial cell monolayers by a mechanism involving regulatory G proteins, *J. Exp. Med.*, 169:1977-91 (1989).

Brouckaert et al., Selective species specificity of tumor necrosis factor for toxicity in the mouse, *Lymphokine Cytokine Res.*, 11(4):193-6 (1992).

Carnemolla et al., Enhancement of the antitumor properties of interleukin-2 by its targeted delivery to the tumor blood vessel extracellular matrix, *Blood*, 99(5):1659-65 (2002).

Carswell et al., An endotoxin-induced serum factor that causes necrosis of tumors, *Proc. Natl. Acad. Sci. USA*, 72(9):3666-70 (1975).

Cassel et al., Retroviral-mediated gene transfer into CD34-enriched human peripheral blood stem cells, *Exp. Hematol.*, 21:585-91 (1993).

Celik et al., Demonstration of immunogenicity with the poorly immunogenic b16 melanoma, *Cancer Res.*, 43:3507-10 (1983).

Chen et al., Enhanced anti-tumor effect of an IFN-gamma-EGF fusion protein, *Biomed. Environ. Sci.* 10:387-95 (1997).

Clauss et al., A polypeptide factor produced by fibrosarcoma cells that induces endothelial tissue factor and enhances the procoagulant response to tumor necrosis factor/cachectin, *J. Exp. Med.*, 172:1535-45 (1990).

Clauss et al., Vascular permeability factor: a tumor-derived polypeptide that induces endothelial cell and monocyte procoagulant activity, and promotes monocyte migration, *J. Biol. Chem.*, 265(12):7078-83 (1990).

Colombo et al., Immunoscintigraphy with anti-chromogranin a antibodies in patients with endocrine/neuroendocrine tumors, *J. Endocrinol. Invest.*, 16:841-3 (1993).

Corti et al., Upregulation of p75 tumor necrosis factor alpha receptor in Mycobacterium avium-infected mice: evidence for a functional role. *Infect. Immunol.*, 67(11):5762-7 (1999).

Corti et al., Tumour necrosis factor: Strategies for improving the therapeutic index. *J. Drug Target.*, 5(6):403-13 (1998).

Corti et al., Oligomeric tumour necrosis factor α slowly converts into inactive forms at bioactive levels, *Biochem. J.*, 284:905-910, 1992.

Corti et al., Tumor necrosis factor (TNF) α quantification by ELISA and bioassay: Effects of TNFα- soluble TNF receptor (p55) complex dissociation during assay incubations, *J. Immunol.* 177: 191-8 (1994).

Corti et al., Tumor targeting with biotinylated tumor necrosis factor α: structure-activity relationships and mechanism of action on avidin pretargeted tumor cells, *Cancer Res.*, 58(17):3866-72 (1998).

Coughlin et al., The effect of interleukin 12 desensitization on the antitumor efficacy of recombinant interleukin 12, *Cancer Res.* 57: 2460-7 (1997).

Curnis et al., Differential binding of drugs containing the NGR motif to CD13 isoforms in tumor vessels, epithelia, and myeloid cells, *Cancer Res.*, 62(3):867-74 (2002).

Curnis et al., Enhancement of tumor necrosis factor alpha antitumor immunotherapeutic properties by targeted delivery to aminopeptidase N (CD13). *Nat. Biotechnol.*, 18(11):1185-90 (2000).

Curtis et al., Targeted delivery of tumor necrosis factor alpha (TNF) to tumor associated vessels. *Int. J. Mol. Med.* 6: Suppl. 1 (2000).

de Wilt et al., *Tumour necrosis factor alpha increases melphalan concentration in tumour tissue after isolated limb perfusion. Br. J. Cancer*, 82(5):1000-3 (2000).

Debs et al., Immunomodulatory and toxic effects of free and liposome-encapsulated tumor necrosis factor a in rats, *Cancer Res.*, 50:375-80 (1990).

Debs et al., Liposome-associated tumor necrosis factor retains bioactivity in the presence of neutralizing anti-tumor necrosis factor antibodies, *J. Immunol.* 143: 1192-7 (1989).

Eggermont et al., Isolated limb perfusion with tumor necrosis factor and melphalan for limb salvage in 186 patients with locally advanced soft tissue extremity sarcomas, *Ann. Surg.*, 224(6):756-65 (1996).

Eggermont et al., Isolated limb perfusion with high-dose tumor necrosis factor-alpha in combination with interferon-gamma and melphalan for nonresectable extremity soft tissue sarcomas: a multicenter trial, *J. Clin. Oncol.*, 14(10):2653-65 (1996).

Elliott et al., TNFα blockade in rheumatoid arthritis: Rationale, clinical outcomes and mechanisms of action, *Int. J. Immunopharmac.*, 17(2):141-5 (1995).

Engelmann et al., Antibodies to a soluble form of a tumor necrosis factor (TNF) receptor have TNF-like activity, *J. Biol. Chem.*, 265(24):14497-504 (1990).

Espevik et al., Characterization of binding and biological effects of monoclonal antibodies against a human tumor necrosis factor receptor, *J. Exp. Med.*, 171:415-26 (1990).

Fiers, Chapter 12: Biologic Therapy with TNF: Preclinical studies. *Biologic Therapy of Cancer: Principles and practice.* 295-327 (1995).

Fraker et al., Chapter 13: Biological Therapy with TNF: Systemic administration and isolation-perfusion. *Biologic Therapy of Cancer: Principles and practice.* 329-45 (1995).

Fraker et al., Treatment of patients with melanoma of the extremity using hyperthermic isolated limb perfusion with melphalan, tumor necrosis factor, and interferon gamma: results of a tumor necrosis factor dose-escalation study. *J. Clin. Oncol.*, 14(2):479-89 (1996).

Fransen et al., Recombinant tumor necrosis factor: its effect and its synergism with interferon-γ on a variety of normal and transformed human cell lines, *Eur. J. Cancer Clin. Oncol.*, 22(4):419-26 (1986).

Gasparri et al., Tumor pretargeting with avidin improves the therapeutic index of biotinylated tumor necrosis factor alpha in mouse models, *Cancer Res.*, 59(12):2917-23 (1999).

Gasparri et al., Chromogranin a fragments modulate cell adhesion, *J. Biol. Chem.*, 272(33):20835-43 (1997).

Genbank Accession No. AF033811.

Genbank Accession No. AF033819.

Ghiara et al., Enhancement of in vivo immune response by tumor necrosis factor, *J. Immunol.* 139(11): 3676-9 (1987).

Goldblum et al., Tumor necrosis factor-alpha augments pulmonary arterial transendothelial albumin flux in vitro, Am. J. Physiol., 258:L57-L67 (1990).

Goodwin, Tumor pretargeting: almost the bottom line, *J. Nucl. Med.*, 36(5):876-9 (1995).

Grell et al., The Transmembrane form of tumor necrosis factor is the prime activating ligand of the 80 kDa tumor necrosis factor receptor, *Cell*, 83(5):793-802 (1995).

Halin et al., Antibody-based targeting of angiogenesis, *News Physiol. Sci.*, 16:191-4 (2001).

Halin et al., Enhancement of the antitumor activity of interleukin-12 by targeted delivery to neovasculature, *Nat. Biotechnol.*, 20(3):264-9 (2002).

Hansen et al., A mouse aminopeptidase N is a marker for antigen-presenting cells and appears to be co-expressed with major histocompatibility complex class II molecules, *Eur. J. Immunol.*, 23:2358-64 (1993).

(56) References Cited

OTHER PUBLICATIONS

Hattori et al., Reduced immunogenicity of beta-lactoglobulin by conjugation with carboxymethyl dextran differing in molecular weight, *J. Agric. Food Chem.* 49: 3789-94 (2000).
Helson et al., Effect of tumour necrosis factor on cultured human melanoma cells, *Nature*, 258:731-2 (1975).
Hieber et al., Tumor necrosis factor for the treatment of malignancies, *Oncology*, 51:142-53 (1994).
Hill et al., Low-dose tumour necrosis factor α and melphalan in hyperthermic isolated limb perfusion, *Br. J. Surg.*, 80:995-7 (1993).
Hoogenboom et al., Construction and expression of antibody-tumor necrosis factor fusion proteins, *Mol. Immunol.*, 28(9):1027-37 (1991).
Jain, Barriers to drug delivery in solid tumors, *Sci. Am.*, 271:42-49 (1994).
Jones et al., A randomised phase ii study of carmustine alone or in combination with tumour necrosis factor in patients with advanced melanoma, *Cancer Chemother. Pharmacol.*, 30:73-76. 1992.
Kimura et al., Phase I study of recombinant human tumor necrosis factor, *Cancer Chemother. Pharmacol.*, 20:223-229, 1987.
Koivunen et al., Tumor targeting with a selective gelatinase inhibitor, *Nat. Biotechnol.*, 17(8):768-74 (1999).
Kost et al., Interferon-gamma and tumor necrosis factor-alpha synergistic cytolytic effects in ovarian cancer cell lines—Roles of the TR60 and TR80 tumor necrosis factor receptors. *Gynecologic Oncology*. 72: 392-401 (1999).
Kristensen et al., Reduction of interstitial fluid pressure after TNF-alpha treatment of three human melanoma xenografts, *Br. J. Cancer*, 74:533-6 (1996).
Lantz et al., Infusion of tumor necrosis factor (tnf) causes an increase in circulating tnf-binding protein in humans, *Cytokine*, 2(6):402-6 (1990).
Leach et al., Safety evaluation of recombinant human interleukin-4. II. Clinical studies, *Clin. Immunol. Immunopathol.* 83: 12-4 (1997).
Lejeune, High dose recombinant tumour necrosis factor (rTNF alpha) administered by isolation perfusion for advanced tumours of the limbs: a model for biochemotherapy of cancer, *Eur. J Cancer*, 31A(6):1009-16 (1995).
Leonard et al., Effects of single-dose interleukin-12 exposure on interleukin-12-associated toxicity and interferon-gamma production, *Blood.* 90: 2541-8 (1997).
Lienard et al., High-dose recombinant tumor necrosis factor alpha in combination with interferon gamma and melphalan in isolation perfusion of the limbs for melanoma and sarcoma, *J. Clin. Oncol.* 10: 52-60 (1992).
Lienard et al., In transit metastases of malignant treated by high dose rtnfα in combination with interferon-γ and melphalan in isolation perfusion, *World J. Surg.*, 16:234-40 (1992).
Ljunggren et al., Host resistance directed selectively against H-2 deficient lymphoma variants, *J. Exp. Med.*, 162:1745-59 (1985).
Loetscher et al., Human tumor necrosis factor alpha (TNF alpha) mutants with exclusive specificity for the 55-kDa or 75-kDa TNF receptors. *J. Biol. Chem.*, 268(35):26350-7 (1993).
Lohn et al., Cell cycle retardation in monocytoid cells induced by aminopeptidase N (CD13). *Leuk. Lymphoma.* 43: 407-13 (2002).
Lu et al., High efficiency retroviral mediated gene transduction into single isolated immature and replatable CD34(3+) hematopoietic stem/progenitor cells from human umbilical cord blood, *J. Exp. Med.*, 178:2089-96 (1993).
Luck et al., Single amino acid substitutions in recombinant bovine prolactin that markedly reduce its mitogenic activity in Nb2 cell cultures, *Mol. Endrocrinol.* 5: 1880-6 (1991).
Luk et al., Flow cytometric analysis of doxorubicin accumulation in cells from human and rodent cell lines, *J. Natl. Cancer Inst.*, 81:55-9 (1989).
McIntosh et al., Studies of effects of recombinant human tumor necrosis factor on autochthonous tumor and transplanted normal tissue in mice, *Cancer Res.*, 50:2463-9 (1990).

Meulders et al., Tumor necrosis factor α increases antifibrinolytic activity of cultured human mesangial cells, *Kidney Int.*, 42:327-34 (1992).
Miyata et al., Overcoming and metastasis-enhancing potential of human tumor-necrosis factor by introducing the cell-adhesive Arg-Gly-Asp sequence, *J. Interferon Cytokine Res.* 15: 161-9 (1995).
Mizuguchi et al., Tumor necrosis factor α-mediated tumor regression by the in vivo transfer of genes into the artery that leads to tumors, *Cancer Res.*, 58:5725-30 (1998).
Modorati et al., Immunoscintigraphy with three step monoclonal pretargeting technique in diagnosis of uveal melanoma: Preliminary results, *Br. J. Ophthalmol.*, 78:19-23 (1994).
Moro et al., Tumor cell targeting with antibody-avidin complexes and biotinylated tumor necrosis factor alpha, *Cancer Res.*, 57:1922-8 (1997).
Naume et al., Involvement of the 55- and 75-kDa tumor necrosis factor receptors in the generation of lymphokine-activated killer cell activity and proliferation of natural killer cells, *J. Immunol.*, 146(9):3045-8 (1991).
Nawroth et al., Modulation of endothelial cell hemostatic properties by tumor necrosis factor, *J. Exp. Med.*, 163:740-5 (1986).
Nawroth et al., Tumor necrosis factor/cachectin-induced intravascular fibrin formation in meth a fibrosarcomas, *J. Exp Med.*, 168:637-47 (1988).
Paganelli et al., Clinical application of the Avidin-Biotin system for tumor targeting. *Cancer Therapy with Radiolabelled Antibodies.* 239-54 (1995).
Paganelli et al., Three-step monoclonal antibody tumor targeting in carcinoembryonic antigen-positive patients, *Cancer Res.*, 51:5960-6 (1991).
Palladino et al., Characterization of the antitumor activities of human tumor necrosis factor-α and the comparsion with other cytokines: induction of tumor-specific immunity, *J. Immunol.*, 138(11):4023-32 (1987).
Pasqualini et al., Aminopeptidase N is a receptor for tumor-homing peptides and a target for inhibiting angiogenesis. *Cancer Res.* 60: 722-7 (2000).
Pasqualini et al., αv integrins as receptors for tumor targeting by circulating ligands, *Nat. Biotechnol.*, 15:542-6, (1997).
Pelagi et al., Caspase inhibition reveals functional cooperation between p55- and p75-TNF receptors in cell necrosis, *Eur. Cytokine Netw.*, 11(4):580-8 (2000).
Pennica et al., Cloning and expression in *Escherichia coli* of the cDNA for murine tumor necrosis factor, *Proc. Natl. Acad. Sci. USA*, 82(18):6060-4 (1985).
Pennica et al., Human tumour necrosis factor: Precursor structure, expression and homology to lymphotoxin, *Nature*. 312:20-9 (1984).
Pfizenmaier et al., Tumor necrosis factor enhances HLA-A,B,C and HLA-DR gene expression in human tumor cells, *J. Immunol.*, 138(3):975-80 (1987).
Ramakrishnan et al., Targeting tumor vasculature using VEGF-toxin conjugates, *Methods Mol. Biol.*, 166:219-34 (2001).
Rathjen et al., Selective enhancement of the tumour necrotic activity of TNF, with monoclonal antibody. *Br. J. Cancer*. 65: 852-6 (1992).
Robert et al., Cytokine targeting in tumors using a bispecific antibody directed against carcinoembryonic antigen and tumor necrosis factor α[1], *Cancer Res.*, 56:4758-65 (1996).
Robertson et al., Immunological effects of interleukin 12 administered by bolus intravenous injection to patients with cancer, *Clin. Cancer Res.* 5: 9-16 (1999).
Rossi et al., Soft tissue limb sarcomas: Italian clinical trials with hyperthermic antiblastic perfusion, *Cancer*, 86(9):1742-9 (1999).
Schiller et al., Clinical and biologic effects of combination therapy with gamma—Interferon and tumor necrosis factor, *Cancer*, 69:562-71 (1992).
Schraffordt-Koops et al., Hyperthermic isolated limb perfusion with tumour necrosis factor and malphalan as treatment of locally advanced or recurrent soft tissue sarcomas of the extremities, *Radiother. Oncol.* 48: 1-4 (1998).
Sella et al., Phase I study of tumor necrosis factor plus actinomycin D in patients with androgen-independent prostate cancer, *Cancer Biother.*, 10(3):225-35 (1995).

(56) References Cited

OTHER PUBLICATIONS

Shipp et al., Hematopoietic differentation antigens that are membrane-associated enzymes: cutting is the key! *Blood*, 82(4):1052-70 (1993).

Sidhu et al., Tumor necrosis factor activities and cancer therapy-A perspective, *Pharmac. Ther.*, 57:79-128 (1993).

Smith et al., The active form of tumor necrosis factor is a trimer, *J. Biol. Chem.*, 262(15):6951-4 (1987).

Soiffer et al., Interleukin-12 augments cytolytic activity of peripheral blood lymphocytes from patients with hematologic and solid malignancies, *Blood*. 82: 2790-6 (1993).

Sosman et al., Concurrent phase I trials of intravenous interleukin 6 in solid tumor patients: reversible dose-limiting neurological toxicity, *Clin. Cancer Res*. 3: 39-46 (1997).

Spriggs et al., Recombinant human tumor necrosis factor administered as a 24-hour intravenous infusion. A phase I and pharmacologic study, *J. Natl. Cancer Inst*. 80(13): 1039-44 (1988). Abstact.

Stadler et al., A phase II study of subcutaneous recombinant human interleukin-4 in metastatic renal cell carcinoma, *Cancer*, 76: 1629-33 (1995).

Stein et al., Cytokine-mediated reversal of multidrug resistance, *Cytotechnology*. 27: 271-82 (1998).

Suk et al., Interferon gamma (IFNgamma) and tumor necrosis factor alpha synergism in ME-180 cervical cancer call apoptosis and necrosis. IFNgamma inhibits cytoprotective NF-kappa B through STAT!/IRF-1 pathways, *J. Biol. Chem*. 276: 13153-9 (2001).

Suzuki et al., Augmentation for intratumoral accumulation and antitumor activity of liposome-encapsulated adriamycin by tumor necrosis factor-alpha in mice, *Int. J. Cancer*, 46:1095-100 (1990).

Tabata et al., Targeting of tumor necrosis factor to tumor by use of Dextran and metal coordination, *J. Control.Release*. 59: 187-96 (1999).

Talmadge et al., Immunomodulatory and immunotherapeutic properties of recombinant-γ interferon and recombinant tumor necrosis factor in mice, *Cancer Res.*, 47:2563-70 (1987).

Tartaglia et al., Ligand passing: The 75-kDa tumor necrosis factor (TNF) receptor recruits TNF for signaling by the 55-kDa TNF receptor, *J. Biol. Chem.*, 268(25):18542-8 (1993).

Tartaglia et al., The two different receptors for tumor necrosis factor mediate distinct cellular responses, *Proc. Natl. Acad. Sci. USA*, 88(20):9292-6 (1991).

Taylor, Aminopeptidases: Structure and function, *FASEB J.*, 7:290-8 (1993).

Tracey et al., Tumor necrosis factor, other cytokines and disease, *Annu. Rev. Cell Biol.*, 9:317-43 (1993).

van de Weil et al., Factors that define the susceptibility of endothelial cells to tumor necrosis factor and lipid A, *Immunopharmacology*, 23:49-56 (1992).

Van der Veen et al., TNF-alpha augments intratumoural concentrations of doxorubicin in TNF-alpha based isolated limb perfusion in rat sarcoma models and enhances anti-tumour effects, *Br. J. Cancer*, 82:973-80 (2000).

Van Ginkel et al., Hyperthermic isolated limb perfusion with TNFalpha and cisplatin in the treatment of osteosarcoma of the extremities: A feasibility study in healthy dogs, *Sarcoma*, 3:89-94 (1999).

Van Ostade et al., Human tumor necrosis factor mutants with professional binding to and activity on either the R55 or R75 receptor, *Eur. J. Biochem.*, 220:771-9 (1994).

Van Ostade et al., Human TNF mutants with selective activity on the p55 receptor, *Nature*, 361(6409):266-9 (1993).

Van Zee et al., A human tumor necrosis factor (TNF) α mutant that binds exclusively to the p55 TNF receptor produces toxicity in the baboon, *J. Exp. Med.*, 179:1185-91 (1994).

Vandenabeele et al., Functional characterization of the human tumor necrosis factor receptor p75 in a transfected rat/mouse T cell hybridoma, *J. Exp. Med.*, 176:1015-24 (1992).

Waldmann et al., Low dose unresponsiveness with thymus independent antigen, *Nature*. 258: 730-1 (1975).

Williamson et al., Human tumor necrosis factor produced by human B-cell lines: Synergistic cytotoxic interaction with human interferon, *Proc. Natl. Acad. Sci. USA*, 80(17):5397-401 (1983).

Wood et al., Novel cyclization chemistry especially suited for biologically derived, unprotected peptides. *Int. J. Pept. Protein Res.*, 39:533-9 (1992).

Xiang et al., Recombinant bifunctional molecule FV/IFN-γ possesses the anti- tumor FV as well as the gamma interferon activities, *Immunol. Cell Biol.*, 72:275-85 (1994).

Xiang et al., Single-chain antibody variable region-targeted interleukin-2 stimulates T cell killing of human colorectal carcinoma cells, *Cancer Biother*., 8(4):327-37 (1993).

Xiang et al., Targeting cytokines to tumors to induce active antitumor immune responses by recombinant fusion proteins, *Hum. Antibodies*, 9(1): 23-36 (1999).

Yang et al., A genetically engineered fusion protein M4/TNF with increased bifunctional activity refolded in the presence of protein disulfide isomerase, *Hum. Antibod. Hybridomas*, 6(4):129-36 (1995).

Yang et al., A genetically engineered single-chain FV/TNF molecule possesses the anti-tumor immunoreactivity of FV as well as the cytotoxic activity of tumor necrosis factor, *Mol. Immunol.*, 32(12):873-81 (1995).

Yilmaz et al., Pulse treatment of human vascular endothelial calls with high doses of tumor necrosis factor and interferon-gamma results in simultaneous synergistic and reversible effects on proliferation and morphology. *Int. J. Cancer*. 77: 592-9 (1998).

Zagozdzon et al., Effective chemo-immunotherapy of L1210 leukemia in vivo using interleukin-12 combined with doxorubicin but not with cyclophosphamide, paclitaxel or cisplatin, *Int J. Cancer*, 77(5): 720-7 (1998).

Declaration Under 37 C.F.R. §1.132 of Dr. Angelo Corti, U.S. Appl. No. 10/492,144.

Indian Search Report, Indian Patent Application No. 2465/CHENP/2004, dated Aug. 21, 2006.

UK Search Report in GB 0209893.7 dated Oct. 10, 2002.

UK Search Report in GB0209896.0 dated Oct. 10, 2002.

* cited by examiner

SEQUENCE LISTING

```
<160> NUMBER OF SEQ ID NOS: 15

<210> SEQ ID NO 1
<211> LENGTH: 13
<212> TYPE: PRT
<213> ORGANISM: Artificial sequence
<220> FEATURE:
<223> OTHER INFORMATION: Synthetic peptide

<400> SEQUENCE: 1

Cys Asn Gly Arg Cys Val Ser Gly Cys Ala Gly Arg Cys
1               5                   10

<210> SEQ ID NO 2
<211> LENGTH: 6
<212> TYPE: PRT
<213> ORGANISM: Artificial sequence
<220> FEATURE:
<223> OTHER INFORMATION: Synthetic peptide

<400> SEQUENCE: 2

Asn Gly Arg Ala His Ala
1               5

<210> SEQ ID NO 3
<211> LENGTH: 5
<212> TYPE: PRT
<213> ORGANISM: Artificial sequence
<220> FEATURE:
<223> OTHER INFORMATION: Synthetic peptide

<400> SEQUENCE: 3

Gly Asn Gly Arg Gly
1               5

<210> SEQ ID NO 4
<211> LENGTH: 9
<212> TYPE: PRT
<213> ORGANISM: Artificial sequence
```

```
<220> FEATURE:
<223> OTHER INFORMATION: Synthetic peptide

<400> SEQUENCE: 4

Cys Val Leu Asn Gly Arg Met Glu Cys
1               5

<210> SEQ ID NO 5
<211> LENGTH: 5
<212> TYPE: PRT
<213> ORGANISM: Artificial sequence
<220> FEATURE:
<223> OTHER INFORMATION: Synthetic peptide

<400> SEQUENCE: 5

Cys Asn Gly Arg Cys
1               5

<210> SEQ ID NO 6
<211> LENGTH: 6
<212> TYPE: PRT
<213> ORGANISM: Artificial sequence
<220> FEATURE:
<223> OTHER INFORMATION: Synthetic peptide

<400> SEQUENCE: 6

Cys Asn Gly Arg Cys Gly
1               5

<210> SEQ ID NO 7
<211> LENGTH: 5
<212> TYPE: PRT
<213> ORGANISM: Artificial sequence
<220> FEATURE:
<223> OTHER INFORMATION: Synthetic peptide

<400> SEQUENCE: 7

Cys Arg Gly Asp Cys
1               5

<210> SEQ ID NO 8
<211> LENGTH: 6
<212> TYPE: PRT
<213> ORGANISM: Artificial sequence
<220> FEATURE:
<223> OTHER INFORMATION: Synthetic peptide

<400> SEQUENCE: 8

Cys Arg Gly Asp Cys Leu
1               5

<210> SEQ ID NO 9
<211> LENGTH: 6
<212> TYPE: PRT
<213> ORGANISM: Artificial sequence
<220> FEATURE:
<223> OTHER INFORMATION: Synthetic peptide

<400> SEQUENCE: 9

Cys Arg Gly Asp Cys Ala
1               5

<210> SEQ ID NO 10
<211> LENGTH: 10
<212> TYPE: PRT
<213> ORGANISM: Artificial sequence
<220> FEATURE:
```

```
<223> OTHER INFORMATION: Synthetic peptide

<400> SEQUENCE: 10

Gly Ala Cys Arg Gly Asp Cys Leu Gly Ala
1               5                   10

<210> SEQ ID NO 11
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: Misc_feature
<222> LOCATION: (1)..(1)
<223> OTHER INFORMATION: Xaa can be any naturally occurring amino acid
<220> FEATURE:
<221> NAME/KEY: Misc_feature
<222> LOCATION: (5)..(5)
<223> OTHER INFORMATION: Xaa can be Thr or Cys
<220> FEATURE:
<221> NAME/KEY: Misc_feature
<222> LOCATION: (6)..(6)
<223> OTHER INFORMATION: Xaa can be any naturally occurring amino acid

<400> SEQUENCE: 11

Xaa Arg Gly Asp Xaa Xaa
1               5

<210> SEQ ID NO 12
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: Misc_feature
<222> LOCATION: (1)..(1)
<223> OTHER INFORMATION: Xaa can be any naturally occurring amino acid
<220> FEATURE:
<221> NAME/KEY: Misc_feature
<222> LOCATION: (5)..(6)
<223> OTHER INFORMATION: Xaa can be any naturally occurring amino acid

<400> SEQUENCE: 12

Xaa Arg Gly Asp Xaa Xaa
1               5

<210> SEQ ID NO 13
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: Misc_feature
<222> LOCATION: (4)..(4)
<223> OTHER INFORMATION: Xaa can be any naturally occurring amino acid

<400> SEQUENCE: 13

Arg Gly Asp Xaa
1

<210> SEQ ID NO 14
<211> LENGTH: 6
<212> TYPE: PRT
<213> ORGANISM: Artificial sequence
<220> FEATURE:
<223> OTHER INFORMATION: Synthetic peptide

<400> SEQUENCE: 14
```

```
Gly Arg Gly Asp Ala Pro
1               5

<210> SEQ ID NO 15
<211> LENGTH: 6
<212> TYPE: PRT
<213> ORGANISM: Artificial sequence
<220> FEATURE:
<223> OTHER INFORMATION: Synthetic peptide

<400> SEQUENCE: 15

Arg Gly Asp Ser Pro Lys
1               5
```

IMMUNOCONJUGATES FOR THE TREATMENT OF TUMOURS

FIELD OF THE INVENTION

IMMUNOCONJUGATES FOR THE TREATMENT OF TUMOURS

BACKGROUND OF THE INVENTION

The antitumor activity of some cytokines is well known and described. Some cytokines have already been used therapeutically in humans. For example, cytokines such as IL-2 and IFN-γ have shown positive antitumoral activity in patients with different types of tumors, such as kidney metastatic carcinoma, hairy cell leukemia, Kaposi sarcoma, melanoma, multiple mieloma, and the like. Other cytokines like IFNβ, the Tumor Necrosis Factor (TNF)α, TNFβ, IL-1, 4, 6, 12, 15 and the Colony Stimulating Factors (CFSs) have shown a certain antitumoral activity on some types of tumors.

In general, the therapeutic use of cytokines is strongly limited by their systemic toxicity. TNF, for example, was originally discovered for its capacity for inducing the hemorrhagic necrosis of some tumors, and for its in vitro cytotoxic effect on different tumoral lines, but is subsequently proved to have strong pro-inflammatory activity, which can, in case of overproduction conditions, dangerously affect the human body.

As the systemic toxicity is a fundamental problem with the use of pharmacologically active amounts of cytokines in humans, novel derivatives and therapeutic strategies are now under evaluation, aimed at reducing the toxic effects of this class of biological effectors while keeping their therapeutic efficacy.

Some novel approaches are directed to:
a) the development of fusion proteins which can deliver TNF into the tumor and increase the local concentration. For example, the fusion proteins consisting of TNF and tumor specific-antibodies have been produced;
b) the development of TNF mutants which maintain the antitumoral activity and have a reduced systemic toxicity. Accordingly, mutants capable of selectively recognizing only one receptor have already been prepared;
c) the use of anti-TNF antibodies able to reduce some toxic effects of TNF without compromising its antitumoral activity. Such antibodies have already been described in literature;
d) the use of TNF derivatives with a higher half-life (for example TNF conjugated with polyethylene glycol).

The preparation of TNF derivatives capable of selectively targeting the tumoral sites has recently been reported. For example, a fusion protein has been described, obtained by fusing the gene of the heavy chain of an anti-transferrin receptor mAb and the TNF gene, or a fusion protein of TNF with the "hinge" region of a monoclonal antibody against the tumor-associated TAG72 antigen, or a Fv-TNF fusion protein.

EP 251 494 discloses a system for administering a diagnostic or therapeutic agent, which comprises: an antibody conjugated with avidin or streptavidin, an agent capable of complexing the conjugated antibody and a compound consisting of the diagnostic or therapeutic agent conjugated with biotin, which are administered sequentially and adequately delayed, so as to allow the localization of the therapeutic or diagnostic agent through the biotin-streptavidin interaction on the target cell recognized by the antibody. The described therapeutic or diagnostic agents comprise metal chelates, in particular chelates of radionuclides and low molecular weight antitumoral agents such as cis-platinum, doxorubicin, etc.

EP 496 074 discloses a method which provides the sequential administration of a biotinylated antibody, avidin or streptavidin and a biotinylated diagnostic or therapeutic agent. Although cytotoxic agents like ricin are generically mentioned, the application relative to radiolabelled compounds is mostly disclosed.

WO 95/15979 discloses a method for localizing highly toxic agents on cellular targets, based on the administration of a first conjugate comprising the specific target molecule conjugated with a ligand or an anti-ligand followed by the administration of a second conjugate consisting of the toxic agent bound to an anti-ligand or to the ligand.

WO 99/13329 discloses a method for targeting a molecule to tumoral angiogenic vessels, based on the conjugation of said molecule with ligands of NGR receptors. A number of molecules have been suggested as possible candidates, but doxorubicin only is specifically described. No use of ligands of NGR receptors as cytokines vehicles to induce immuno responses is disclosed.

In WO01/61017 the current inventor describes how surprisingly he has found that the therapeutic index of certain cytokines can be remarkably improved and their immunotherapeutic properties can be enhanced by coupling with a ligand of the aminopeptidase-N receptor (CD13). CD13 is a transmembrane glycoprotein of 150 kDa which is highly conserved in various species. It is expressed on normal cells as well as in myeloid tumor lines, in the angiogenic endothelium and in some epithelia. The CD13 receptor is usually identified as the "NGR" receptor, in that its peptide ligands share the amino acid "NGR" motif.

However, there remains a need for further and improved pharmaceutical compositions and methods for the treatment and diagnosis of cancer.

SUMMARY OF THE INVENTION

Drug delivery and penetration into neoplastic cells is critical for the effectiveness of tumor chemotherapy. We have now found that surprisingly targeted delivery of picogram doses of cytokines enhances the penetration of chemotherapeutic drugs. In more detail, we have found that delivery of very low doses of cytokines to tumors and the tumor-associated environment including tumor vasculature represents a new approach to avoiding negative feedback mechanisms and to preserve its ability to alter drug-penetration barriers. The present invention thus represents a novel and surprising strategy for increasing the therapeutic index of chemotherapeutic drugs. In a preferred embodiment, we have found using vascular targeting achieved by coupling TNF with CNGRC (SEQ ID NO: 5), a peptide that targets the tumor neovasculature, that this treatment enhanced 8-10 times the therapeutic efficacy of doxorubicin, with no evidence of increased toxicity. Similarly, vascular targeting enhanced the efficacy of melphalan, a different chemotherapeutic drug. Synergy with chemotherapy was observed with 3-5 ng/kg of targeted TNF (i. p.), $10^6$-fold lower than the $LD_{50}$ and $10^5$-fold lower than the dose required for non-targeted TNF. In addition, we have also found that targeted delivery of low doses of TNF to tumor vessels does not induce the release of soluble TNF receptors in circulation. We have also found that RGD-TNF and IFNγ-NGR are active in the picogram range. We have also shown that NGR-TNF increases the effect of cisplatinum. These results indicate that the delivery of minute amounts of cytokines to tumor vessels represents a new approach to avoid negative feedback mechanisms and to preserve its ability to alter drug-penetration barriers. Vascular targeting in this way represents a novel strategy for increasing the therapeutic index of chemotherapeutic drugs.

STATEMENTS OF THE INVENTION

According to one aspect of the present invention there is provided a pharmaceutical composition comprising a conjugate of a cytokine and a tumor targeting moiety (TTM) and a pharmaceutically acceptable carrier, diluent or excipient, wherein the cytokine is present in an amount which does not induce a negative feedback mechanism. Thus, the cytokine is present in an amount which does not induce soluble cytokine receptor shedding.

Preferably the conjugate is present in an amount to provide a dosage in the range of 0.5 to 500 ng/kg, more preferably 1 to 50 ng/kg, and most preferably 5 to 15 ng/kg.

In one embodiment the cytokine is an inflammatory cytokine.

In another embodiment the cytokine is a chemotherapeutic cytokine.

Preferably the cytokine is selected from: TNF, such as TNFα, TNFβ, IFNα, IFNβ, IFNγ, IL-1, 2, 4, 6, 12, 15, EMAP II, vascular endothelial growth factor (VEGF), PDGF, PD-ECGF or a chemokine.

In a more preferred embodiment the cytokine is TNF-α, TNF-β or IFN-γ, most preferably TNF-α or TNF-β.

In one embodiment the TTM is a binding partner such as a ligand of, or antibody to a tumor cell surface molecule such as a receptor, marker or other extracellular component.

In another embodiment the TTM is a tumor vasculature targeting moiety (TVTM), and may be a binding partner such as a ligand of, or antibody to a tumor vasculature cell surface molecule such as a receptor, marker or other extracellular component.

In one embodiment the TTM is an antibody or fragment thereof.

In another embodiment the TTM is a ligand or fragment thereof.

In a preferred embodiment the TTM is a peptide containing the NGR or RGD motif, or is HIV-tat, Annexin V, Osteopontin, Fibronectin, Collagen Type I or IV, Hyaluronate or Ephrin, or is a binding partner, such as an antibody to oncofetal fibronectin; or is a fragment of any of the foregoing. In a more preferred embodiment the TTM contains the NGR motif. In a most preferred embodiment the TTM is CNGRCVSG-CAGRC (SEQ ID NO: 1), NGRAHA (SEQ ID NO: 2), GNGRG (SEQ ID NO: 3), cycloCVLNGRMEC (SEQ ID NO: 4), linear or cyclic CNGRC (SEQ ID NO: 5).

In another preferred embodiment the TTM is a peptide containing the RGD motif.

In one embodiment the TTM is targeted to VEGFR, ICAM 1, 2 or 3, PECAM-1, CD13, VCAM-1, Selectin, Act RII, ActRIIB, ActRI, ActRIB, CD44, aminopeptidase A, aminopeptidase N (CD13), αvβ3 integrin, αvβ5 integrin, FGF-1, 2, 3, or 4, IL-1R, EPHR, MMP, NG2, tenascin, oncofetal fibronectin, PD-ECGFR, TNFR, PDGFR or PSMA.

Combinations of preferred targeting moieties and cytokines which may be used in the present invention are shown in the Table below.

| Cytokine | Targeting Moiety |
|---|---|
| TNF-α | RGD-CONTAINING PEPTIDE |
| TNF-β | RGD-CONTAINING PEPTIDE |
| IFN-α | RGD-CONTAINING PEPTIDE |

-continued

| Cytokine | Targeting Moiety |
|---|---|
| IFN-β | RGD-CONTAINING PEPTIDE |
| IFN-γ | RGD-CONTAINING PEPTIDE |
| IL-2 | RGD-CONTAINING PEPTIDE |
| IL-12 | RGD-CONTAINING PEPTIDE |
| EMAP II | RGD-CONTAINING PEPTIDE |
| VEGF | RGD-CONTAINING PEPTIDE |
| IL-1 | RGD-CONTAINING PEPTIDE |
| IL-6 | RGD-CONTAINING PEPTIDE |
| IL-12 | RGD-CONTAINING PEPTIDE |
| PDGF | RGD-CONTAINING PEPTIDE |
| PD-ECGF | RGD-CONTAINING PEPTIDE |
| CXC chemokine | RGD-CONTAINING PEPTIDE |
| CC chemokine | RGD-CONTAINING PEPTIDE |
| C chemokine | RGD-CONTAINING PEPTIDE |
| IL-15 | RGD-CONTAINING PEPTIDE |
| TNF-α | NGR-CONTAINING PEPTIDE |
| TNF-β | NGR-CONTAINING PEPTIDE |
| IFN-α | NGR-CONTAINING PEPTIDE |
| IFN-β | NGR-CONTAINING PEPTIDE |
| IFN-γ | NGR-CONTAINING PEPTIDE |
| IL-2 | NGR-CONTAINING PEPTIDE |
| IL-12 | NGR-CONTAINING PEPTIDE |
| EMAP II | NGR-CONTAINING PEPTIDE |
| VEGF | NGR-CONTAINING PEPTIDE |
| IL-1 | NGR-CONTAINING PEPTIDE |
| IL-6 | NGR-CONTAINING PEPTIDE |
| IL-12 | NGR-CONTAINING PEPTIDE |
| PDGF | NGR-CONTAINING PEPTIDE |
| PD-ECGF | NGR-CONTAINING PEPTIDE |
| CXC chemokine | NGR-CONTAINING PEPTIDE |
| CC chemokine | NGR-CONTAINING PEPTIDE |
| C chemokine | NGR-CONTAINING PEPTIDE |
| IL-15 | NGR-CONTAINING PEPTIDE |
| TNF-α | Ligand to VEGFR |
| TNF-β | Ligand to VEGFR |
| IFN-α | Ligand to VEGFR |
| IFN-β | Ligand to VEGFR |
| IFN-γ | Ligand to VEGFR |
| IL-2 | Ligand to VEGFR |
| IL-12 | Ligand to VEGFR |
| EMAP II | Ligand to VEGFR |
| VEGF | Ligand to VEGFR |
| IL-1 | Ligand to VEGFR |
| IL-6 | Ligand to VEGFR |
| IL-12 | Ligand to VEGFR |
| PDGF | Ligand to VEGFR |
| PD-ECGF | Ligand to VEGFR |
| CXC chemokine | Ligand to VEGFR |
| CC chemokine | Ligand to VEGFR |
| C chemokine | Ligand to VEGFR |
| IL-15 | Ligand to VEGFR |
| TNF-α | Ab to VEGFR |
| TNF-β | Ab to VEGFR |
| IFN-α | Ab to VEGFR |
| IFN-β | Ab to VEGFR |
| IFN-γ | Ab to VEGFR |
| IL-2 | Ab to VEGFR |
| IL-12 | Ab to VEGFR |
| EMAP II | Ab to VEGFR |
| VEGF | Ab to VEGFR |
| IL-1 | Ab to VEGFR |
| IL-6 | Ab to VEGFR |
| IL-12 | Ab to VEGFR |
| PDGF | Ab to VEGFR |
| PD-ECGF | Ab to VEGFR |
| CXC chemokine | Ab to VEGFR |
| CC chemokine | Ab to VEGFR |
| C chemokine | Ab to VEGFR |
| IL-15 | Ab to VEGFR |
| TNF-α | HIV-tat |
| TNF-β | HIV-tat |
| IFN-α | HIV-tat |
| IFN-β | HIV-tat |
| IFN-γ | HIV-tat |
| IL-2 | HIV-tat |
| IL-12 | HIV-tat |
| EMAP II | HIV-tat |

-continued

| Cytokine | Targeting Moiety |
|---|---|
| VEGF | HIV-tat |
| IL-1 | HIV-tat |
| IL-6 | HIV-tat |
| IL-12 | HIV-tat |
| PDGF | HIV-tat |
| PD-ECGF | HIV-tat |
| CXC chemokine | HIV-tat |
| CC chemokine | HIV-tat |
| C chemokine | HIV-tat |
| IL-15 | HIV-tat |
| TNF-α | Ligand to ICAM 1, 2 or 3 |
| TNF-β | Ligand to ICAM 1, 2 or 3 |
| IFN-α | Ligand to ICAM 1, 2 or 3 |
| IFN-β | Ligand to ICAM 1, 2 or 3 |
| IFN-γ | Ligand to ICAM 1, 2 or 3 |
| IL-2 | Ligand to ICAM 1, 2 or 3 |
| IL-12 | Ligand to ICAM 1, 2 or 3 |
| EMAP II | Ligand to ICAM 1, 2 or 3 |
| VEGF | Ligand to ICAM 1, 2 or 3 |
| IL-1 | Ligand to ICAM 1, 2 or 3 |
| IL-6 | Ligand to ICAM 1, 2 or 3 |
| IL-12 | Ligand to ICAM 1, 2 or 3 |
| PDGF | Ligand to ICAM 1, 2 or 3 |
| PD-ECGF | Ligand to ICAM 1, 2 or 3 |
| CXC chemokine | Ligand to ICAM 1, 2 or 3 |
| CC chemokine | Ligand to ICAM 1, 2 or 3 |
| C chemokine | Ligand to ICAM 1, 2 or 3 |
| IL-15 | Ligand to ICAM 1, 2 or 3 |
| TNF-α | Ab to ICAM 1, 2 or 3 |
| TNF-β | Ab to ICAM 1, 2 or 3 |
| IFN-α | Ab to ICAM 1, 2 or 3 |
| IFN-β | Ab to ICAM 1, 2 or 3 |
| IFN-γ | Ab to ICAM 1, 2 or 3 |
| IL-2 | Ab to ICAM 1, 2 or 3 |
| IL-12 | Ab to ICAM 1, 2 or 3 |
| EMAP II | Ab to ICAM 1, 2 or 3 |
| VEGF | Ab to ICAM 1, 2 or 3 |
| IL-1 | Ab to ICAM 1, 2 or 3 |
| IL-6 | Ab to ICAM 1, 2 or 3 |
| IL-12 | Ab to ICAM 1, 2 or 3 |
| PDGF | Ab to ICAM 1, 2 or 3 |
| PD-ECGF | Ab to ICAM 1, 2 or 3 |
| CXC chemokine | Ab to ICAM 1, 2 or 3 |
| CC chemokine | Ab to ICAM 1, 2 or 3 |
| C chemokine | Ab to ICAM 1, 2 or 3 |
| IL-15 | Ab to ICAM 1, 2 or 3 |
| TNF-α | Ligand to PECAM-1/CD31 |
| TNF-β | Ligand to PECAM-1/CD31 |
| IFN-α | Ligand to PECAM-1/CD31 |
| IFN-β | Ligand to PECAM-1/CD31 |
| IFN-γ | Ligand to PECAM-1/CD31 |
| IL-2 | Ligand to PECAM-1/CD31 |
| IL-12 | Ligand to PECAM-1/CD31 |
| EMAP II | Ligand to PECAM-1/CD31 |
| VEGF | Ligand to PECAM-1/CD31 |
| IL-1 | Ligand to PECAM-1/CD31 |
| IL-6 | Ligand to PECAM-1/CD31 |
| IL-12 | Ligand to PECAM-1/CD31 |
| PDGF | Ligand to PECAM-1/CD31 |
| PD-ECGF | Ligand to PECAM-1/CD31 |
| CXC chemokine | Ligand to PECAM-1/CD31 |
| CC chemokine | Ligand to PECAM-1/CD31 |
| C chemokine | Ligand to PECAM-1/CD31 |
| IL-15 | Ligand to PECAM-1/CD31 |
| TNF-α | Ab to PECAM-1/CD31 |
| TNF-β | Ab to PECAM-1/CD31 |
| IFN-α | Ab to PECAM-1/CD31 |
| IFN-β | Ab to PECAM-1/CD31 |
| IFN-γ | Ab to PECAM-1/CD31 |
| IL-2 | Ab to PECAM-1/CD31 |
| IL-12 | Ab to PECAM-1/CD31 |
| EMAP II | Ab to PECAM-1/CD31 |
| VEGF | Ab to PECAM-1/CD31 |
| IL-1 | Ab to PECAM-1/CD31 |
| IL-6 | Ab to PECAM-1/CD31 |
| IL-12 | Ab to PECAM-1/CD31 |
| PDGF | Ab to PECAM-1/CD31 |

-continued

| Cytokine | Targeting Moiety |
|---|---|
| PD-ECGF | Ab to PECAM-1/CD31 |
| CXC chemokine | Ab to PECAM-1/CD31 |
| CC chemokine | Ab to PECAM-1/CD31 |
| C chemokine | Ab to PECAM-1/CD31 |
| IL-15 | Ab to PECAM-1/CD31 |
| TNF-α | Ligand to VCAM-1 |
| TNF-β | Ligand to VCAM-1 |
| IFN-α | Ligand to VCAM-1 |
| IFN-β | Ligand to VCAM-1 |
| IFN-γ | Ligand to VCAM-1 |
| IL-2 | Ligand to VCAM-1 |
| IL-12 | Ligand to VCAM-1 |
| EMAP II | Ligand to VCAM-1 |
| VEGF | Ligand to VCAM-1 |
| IL-1 | Ligand to VCAM-1 |
| IL-6 | Ligand to VCAM-1 |
| IL-12 | Ligand to VCAM-1 |
| PDGF | Ligand to VCAM-1 |
| PD-ECGF | Ligand to VCAM-1 |
| CXC chemokine | Ligand to VCAM-1 |
| CC chemokine | Ligand to VCAM-1 |
| C chemokine | Ligand to VCAM-1 |
| IL-15 | Ligand to VCAM-1 |
| TNF-α | Ab to VCAM-1 |
| TNF-β | Ab to VCAM-1 |
| IFN-α | Ab to VCAM-1 |
| IFN-β | Ab to VCAM-1 |
| IFN-γ | Ab to VCAM-1 |
| IL-2 | Ab to VCAM-1 |
| IL-12 | Ab to VCAM-1 |
| EMAP II | Ab to VCAM-1 |
| VEGF | Ab to VCAM-1 |
| IL-1 | Ab to VCAM-1 |
| IL-6 | Ab to VCAM-1 |
| IL-12 | Ab to VCAM-1 |
| PDGF | Ab to VCAM-1 |
| PD-ECGF | Ab to VCAM-1 |
| CXC chemokine | Ab to VCAM-1 |
| CC chemokine | Ab to VCAM-1 |
| C chemokine | Ab to VCAM-1 |
| IL-15 | Ab to VCAM-1 |
| TNF-α | Ligand to Selectin |
| TNF-β | Ligand to Selectin |
| IFN-α | Ligand to Selectin |
| IFN-β | Ligand to Selectin |
| IFN-γ | Ligand to Selectin |
| IL-2 | Ligand to Selectin |
| IL-12 | Ligand to Selectin |
| EMAP II | Ligand to Selectin |
| VEGF | Ligand to Selectin |
| IL-1 | Ligand to Selectin |
| IL-6 | Ligand to Selectin |
| IL-12 | Ligand to Selectin |
| PDGF | Ligand to Selectin |
| PD-ECGF | Ligand to Selectin |
| CXC chemokine | Ligand to Selectin |
| CC chemokine | Ligand to Selectin |
| C chemokine | Ligand to Selectin |
| IL-15 | Ligand to Selectin |
| TNF-α | Ab to Selectin |
| TNF-β | Ab to Selectin |
| IFN-α | Ab to Selectin |
| IFN-β | Ab to Selectin |
| IFN-γ | Ab to Selectin |
| IL-2 | Ab to Selectin |
| IL-12 | Ab to Selectin |
| EMAP II | Ab to Selectin |
| VEGF | Ab to Selectin |
| IL-1 | Ab to Selectin |
| IL-6 | Ab to Selectin |
| IL-12 | Ab to Selectin |
| PDGF | Ab to Selectin |
| PD-ECGF | Ab to Selectin |
| CXC chemokine | Ab to Selectin |
| CC chemokine | Ab to Selectin |
| C chemokine | Ab to Selectin |
| IL-15 | Ab to Selectin |

-continued

| Cytokine | Targeting Moiety |
|---|---|
| TNF-α | Ligand to ActRII, ActRIIB, ActRI or ActRIB |
| TNF-β | Ligand to ActRII, ActRIIB, ActRI or ActRIB |
| IFN-α | Ligand to ActRII, ActRIIB, ActRI or ActRIB |
| IFN-β | Ligand to ActRII, ActRIIB, ActRI or ActRIB |
| IFN-γ | Ligand to ActRII, ActRIIB, ActRI or ActRIB |
| IL-2 | Ligand to ActRII, ActRIIB, ActRI or ActRIB |
| IL-12 | Ligand to ActRII, ActRIIB, ActRI or ActRIB |
| EMAP II | Ligand to ActRII, ActRIIB, ActRI or ActRIB |
| VEGF | Ligand to ActRII, ActRIIB, ActRI or ActRIB |
| IL-1 | Ligand to ActRII, ActRIIB, ActRI or ActRIB |
| IL-6 | Ligand to ActRII, ActRIIB, ActRI or ActRIB |
| IL-12 | Ligand to ActRII, ActRIIB, ActRI or ActRIB |
| PDGF | Ligand to ActRII, ActRIIB, ActRI or ActRIB |
| PD-ECGF | Ligand to ActRII, ActRIIB, ActRI or ActRIB |
| CXC chemokine | Ligand to ActRII, ActRIIB, ActRI or ActRIB |
| CC chemokine | Ligand to ActRII, ActRIIB, ActRI or ActRIB |
| C chemokine | Ligand to ActRII, ActRIIB, ActRI or ActRIB |
| IL-15 | Ligand to ActRII, ActRIIB, ActRI or ActRIB |
| TNF-α | Ab to ActRII, ActRIIB, ActRI or ActRIB |
| TNF-β | Ab to ActRII, ActRIIB, ActRI or ActRIB |
| IFN-α | Ab to ActRII, ActRIIB, ActRI or ActRIB |
| IFN-β | Ab to ActRII, ActRIIB, ActRI or ActRIB |
| IFN-γ | Ab to ActRII, ActRIIB, ActRI or ActRIB |
| IL-2 | Ab to ActRII, ActRIIB, ActRI or ActRIB |
| IL-12 | Ab to ActRII, ActRIIB, ActRI or ActRIB |
| EMAP II | Ab to ActRII, ActRIIB, ActRI or ActRIB |
| VEGF | Ab to ActRII, ActRIIB, ActRI or ActRIB |
| IL-1 | Ab to ActRII, ActRIIB, ActRI or ActRIB |
| IL-6 | Ab to ActRII, ActRIIB, ActRI or ActRIB |
| IL-12 | Ab to ActRII, ActRIIB, ActRI or ActRIB |
| PDGF | Ab to ActRII, ActRIIB, ActRI or ActRIB |
| PD-ECGF | Ab to ActRII, ActRIIB, ActRI or ActRIB |
| CXC chemokine | Ab to ActRII, ActRIIB, ActRI or ActRIB |
| CC chemokine | Ab to ActRII, ActRIIB, ActRI or ActRIB |
| C chemokine | Ab to ActRII, ActRIIB, ActRI or ActRIB |
| IL-15 | Ab to ActRII, ActRIIB, ActRI or ActRIB |
| TNF-α | Annexin V |
| TNF-β | Annexin V |
| IFN-α | Annexin V |
| IFN-β | Annexin V |
| IFN-γ | Annexin V |
| IL-2 | Annexin V |
| IL-12 | Annexin V |
| EMAP II | Annexin V |
| VEGF | Annexin V |
| IL-1 | Annexin V |
| IL-6 | Annexin V |
| IL-12 | Annexin V |
| PDGF | Annexin V |
| PD-ECGF | Annexin V |
| CXC chemokine | Annexin V |
| CC chemokine | Annexin V |
| C chemokine | Annexin V |
| IL-15 | Annexin V |
| TNF-α | Ligand to CD44 |
| TNF-β | Ligand to CD44 |
| IFN-α | Ligand to CD44 |
| IFN-β | Ligand to CD44 |
| IFN-γ | Ligand to CD44 |
| IL-2 | Ligand to CD44 |
| IL-12 | Ligand to CD44 |
| EMAP II | Ligand to CD44 |
| VEGF | Ligand to CD44 |
| IL-1 | Ligand to CD44 |
| IL-6 | Ligand to CD44 |
| IL-12 | Ligand to CD44 |
| PDGF | Ligand to CD44 |
| PD-ECGF | Ligand to CD44 |
| CXC chemokine | Ligand to CD44 |
| CC chemokine | Ligand to CD44 |
| C chemokine | Ligand to CD44 |
| IL-15 | Ligand to CD44 |
| TNF-α | Ab to CD44 |
| TNF-β | Ab to CD44 |
| IFN-α | Ab to CD44 |
| IFN-β | Ab to CD44 |
| IFN-γ | Ab to CD44 |
| IL-2 | Ab to CD44 |
| IL-12 | Ab to CD44 |
| EMAP II | Ab to CD44 |
| VEGF | Ab to CD44 |
| IL-1 | Ab to CD44 |
| IL-6 | Ab to CD44 |
| IL-12 | Ab to CD44 |
| PDGF | Ab to CD44 |
| PD-ECGF | Ab to CD44 |
| CXC chemokine | Ab to CD44 |
| CC chemokine | Ab to CD44 |
| C chemokine | Ab to CD44 |
| IL-15 | Ab to CD44 |
| TNF-α | Osteopontin |
| TNF-β | Osteopontin |
| IFN-α | Osteopontin |
| IFN-β | Osteopontin |
| IFN-γ | Osteopontin |
| IL-2 | Osteopontin |
| IL-12 | Osteopontin |
| EMAP II | Osteopontin |
| VEGF | Osteopontin |
| IL-1 | Osteopontin |
| IL-6 | Osteopontin |
| IL-12 | Osteopontin |
| PDGF | Osteopontin |
| PD-ECGF | Osteopontin |
| CXC chemokine | Osteopontin |
| CC chemokine | Osteopontin |
| C chemokine | Osteopontin |
| IL-15 | Osteopontin |
| TNF-α | Fibronectin |
| TNF-β | Fibronectin |
| IFN-α | Fibronectin |
| IFN-β | Fibronectin |
| IFN-γ | Fibronectin |
| IL-2 | Fibronectin |
| IL-12 | Fibronectin |
| EMAP II | Fibronectin |
| VEGF | Fibronectin |
| IL-1 | Fibronectin |
| IL-6 | Fibronectin |
| IL-12 | Fibronectin |
| PDGF | Fibronectin |
| PD-ECGF | Fibronectin |
| CXC chemokine | Fibronectin |
| CC chemokine | Fibronectin |
| C chemokine | Fibronectin |
| IL-15 | Fibronectin |
| TNF-α | Collagen type I or IV |
| TNF-β | Collagen type I or IV |
| IFN-α | Collagen type I or IV |
| IFN-β | Collagen type I or IV |
| IFN-γ | Collagen type I or IV |
| IL-2 | Collagen type I or IV |
| IL-12 | Collagen type I or IV |
| EMAP II | Collagen type I or IV |
| VEGF | Collagen type I or IV |
| IL-1 | Collagen type I or IV |

| Cytokine | Targeting Moiety |
|---|---|
| IL-6 | Collagen type I or IV |
| IL-12 | Collagen type I or IV |
| PDGF | Collagen type I or IV |
| PD-ECGF | Collagen type I or IV |
| CXC chemokine | Collagen type I or IV |
| CC chemokine | Collagen type I or IV |
| C chemokine | Collagen type I or IV |
| IL-15 | Collagen type I or IV |
| TNF-α | Hyaluronate |
| TNF-β | Hyaluronate |
| IFN-α | Hyaluronate |
| IFN-β | Hyaluronate |
| IFN-γ | Hyaluronate |
| IL-2 | Hyaluronate |
| IL-12 | Hyaluronate |
| EMAP II | Hyaluronate |
| VEGF | Hyaluronate |
| IL-1 | Hyaluronate |
| IL-6 | Hyaluronate |
| IL-12 | Hyaluronate |
| PDGF | Hyaluronate |
| PD-ECGF | Hyaluronate |
| CXC chemokine | Hyaluronate |
| CC chemokine | Hyaluronate |
| C chemokine | Hyaluronate |
| IL-15 | Hyaluronate |
| TNF-α | Ligand to FGF-1, 2, 3 or 4 |
| TNF-β | Ligand to FGF-1, 2, 3 or 4 |
| IFN-α | Ligand to FGF-1, 2, 3 or 4 |
| IFN-β | Ligand to FGF-1, 2, 3 or 4 |
| IFN-γ | Ligand to FGF-1, 2, 3 or 4 |
| IL-2 | Ligand to FGF-1, 2, 3 or 4 |
| IL-12 | Ligand to FGF-1, 2, 3 or 4 |
| EMAP II | Ligand to FGF-1, 2, 3 or 4 |
| VEGF | Ligand to FGF-1, 2, 3 or 4 |
| IL-1 | Ligand to FGF-1, 2, 3 or 4 |
| IL-6 | Ligand to FGF-1, 2, 3 or 4 |
| IL-12 | Ligand to FGF-1, 2, 3 or 4 |
| PDGF | Ligand to FGF-1, 2, 3 or 4 |
| PD-ECGF | Ligand to FGF-1, 2, 3 or 4 |
| CXC chemokine | Ligand to FGF-1, 2, 3 or 4 |
| CC chemokine | Ligand to FGF-1, 2, 3 or 4 |
| C chemokine | Ligand to FGF-1, 2, 3 or 4 |
| IL-15 | Ligand to FGF-1, 2, 3 or 4 |
| TNF-α | Ab to FGF-1, 2, 3 or 4 |
| TNF-β | Ab to FGF-1, 2, 3 or 4 |
| IFN-α | Ab to FGF-1, 2, 3 or 4 |
| IFN-β | Ab to FGF-1, 2, 3 or 4 |
| IFN-γ | Ab to FGF-1, 2, 3 or 4 |
| IL-2 | Ab to FGF-1, 2, 3 or 4 |
| IL-12 | Ab to FGF-1, 2, 3 or 4 |
| EMAP II | Ab to FGF-1, 2, 3 or 4 |
| VEGF | Ab to FGF-1, 2, 3 or 4 |
| IL-1 | Ab to FGF-1, 2, 3 or 4 |
| IL-6 | Ab to FGF-1, 2, 3 or 4 |
| IL-12 | Ab to FGF-1, 2, 3 or 4 |
| PDGF | Ab to FGF-1, 2, 3 or 4 |
| PD-ECGF | Ab to FGF-1, 2, 3 or 4 |
| CXC chemokine | Ab to FGF-1, 2, 3 or 4 |
| CC chemokine | Ab to FGF-1, 2, 3 or 4 |
| C chemokine | Ab to FGF-1, 2, 3 or 4 |
| IL-15 | Ab to FGF-1, 2, 3 or 4 |
| TNF-α | Ligand to IL-1R |
| TNF-β | Ligand to IL-1R |
| IFN-α | Ligand to IL-1R |
| IFN-β | Ligand to IL-1R |
| IFN-γ | Ligand to IL-1R |
| IL-2 | Ligand to IL-1R |
| IL-12 | Ligand to IL-1R |
| EMAP II | Ligand to IL-1R |
| VEGF | Ligand to IL-1R |
| IL-1 | Ligand to IL-1R |
| IL-6 | Ligand to IL-1R |
| IL-12 | Ligand to IL-1R |
| PDGF | Ligand to IL-1R |
| PD-ECGF | Ligand to IL-1R |
| CXC chemokine | Ligand to IL-1R |
| CC chemokine | Ligand to IL-1R |
| C chemokine | Ligand to IL-1R |
| IL-15 | Ligand to IL-1R |
| TNF-α | Ab to IL-1R |
| TNF-β | Ab to IL-1R |
| IFN-α | Ab to IL-1R |
| IFN-β | Ab to IL-1R |
| IFN-γ | Ab to IL-1R |
| IL-2 | Ab to IL-1R |
| IL-12 | Ab to IL-1R |
| EMAP II | Ab to IL-1R |
| VEGF | Ab to IL-1R |
| IL-1 | Ab to IL-1R |
| IL-6 | Ab to IL-1R |
| IL-12 | Ab to IL-1R |
| PDGF | Ab to IL-1R |
| PD-ECGF | Ab to IL-1R |
| CXC chemokine | Ab to IL-1R |
| CC chemokine | Ab to IL-1R |
| C chemokine | Ab to IL-1R |
| IL-15 | Ab to IL-1R |
| TNF-α | Ligand to CD31 |
| TNF-β | Ligand to CD31 |
| IFN-α | Ligand to CD31 |
| IFN-β | Ligand to CD31 |
| IFN-γ | Ligand to CD31 |
| IL-2 | Ligand to CD31 |
| IL-12 | Ligand to CD31 |
| EMAP II | Ligand to CD31 |
| VEGF | Ligand to CD31 |
| IL-1 | Ligand to CD31 |
| IL-6 | Ligand to CD31 |
| IL-12 | Ligand to CD31 |
| PDGF | Ligand to CD31 |
| PD-ECGF | Ligand to CD31 |
| CXC chemokine | Ligand to CD31 |
| CC chemokine | Ligand to CD31 |
| C chemokine | Ligand to CD31 |
| IL-15 | Ligand to CD31 |
| TNF-α | Ab to CD31 |
| TNF-β | Ab to CD31 |
| IFN-α | Ab to CD31 |
| IFN-β | Ab to CD31 |
| IFN-γ | Ab to CD31 |
| IL-2 | Ab to CD31 |
| IL-12 | Ab to CD31 |
| EMAP II | Ab to CD31 |
| VEGF | Ab to CD31 |
| IL-1 | Ab to CD31 |
| IL-6 | Ab to CD31 |
| IL-12 | Ab to CD31 |
| PDGF | Ab to CD31 |
| PD-ECGF | Ab to CD31 |
| CXC chemokine | Ab to CD31 |
| CC chemokine | Ab to CD31 |
| C chemokine | Ab to CD31 |
| IL-15 | Ab to CD31 |
| TNF-α | Ligand to EPHR |
| TNF-β | Ligand to EPHR |
| IFN-α | Ligand to EPHR |
| IFN-β | Ligand to EPHR |
| IFN-γ | Ligand to EPHR |
| IL-2 | Ligand to EPHR |
| IL-12 | Ligand to EPHR |
| EMAP II | Ligand to EPHR |
| VEGF | Ligand to EPHR |
| IL-1 | Ligand to EPHR |
| IL-6 | Ligand to EPHR |
| IL-12 | Ligand to EPHR |
| PDGF | Ligand to EPHR |
| PD-ECGF | Ligand to EPHR |
| CXC chemokine | Ligand to EPHR |
| CC chemokine | Ligand to EPHR |
| C chemokine | Ligand to EPHR |
| IL-15 | Ligand to EPHR |
| TNF-α | Ab to EPHR |
| TNF-β | Ab to EPHR |

| Cytokine | Targeting Moiety |
|---|---|
| IFN-α | Ab to EPHR |
| IFN-β | Ab to EPHR |
| IFN-γ | Ab to EPHR |
| IL-2 | Ab to EPHR |
| IL-12 | Ab to EPHR |
| EMAP II | Ab to EPHR |
| VEGF | Ab to EPHR |
| IL-1 | Ab to EPHR |
| IL-6 | Ab to EPHR |
| IL-12 | Ab to EPHR |
| PDGF | Ab to EPHR |
| PD-ECGF | Ab to EPHR |
| CXC chemokine | Ab to EPHR |
| CC chemokine | Ab to EPHR |
| C chemokine | Ab to EPHR |
| IL-15 | Ab to EPHR |
| TNF-α | Ephrin |
| TNF-β | Ephrin |
| IFN-α | Ephrin |
| IFN-β | Ephrin |
| IFN-γ | Ephrin |
| IL-2 | Ephrin |
| IL-12 | Ephrin |
| EMAP II | Ephrin |
| VEGF | Ephrin |
| IL-1 | Ephrin |
| IL-6 | Ephrin |
| IL-12 | Ephrin |
| PDGF | Ephrin |
| PD-ECGF | Ephrin |
| CXC chemokine | Ephrin |
| CC chemokine | Ephrin |
| C chemokine | Ephrin |
| IL-15 | Ephrin |
| TNF-α | Ligand to MMP |
| TNF-β | Ligand to MMP |
| IFN-α | Ligand to MMP |
| IFN-β | Ligand to MMP |
| IFN-γ | Ligand to MMP |
| IL-2 | Ligand to MMP |
| IL-12 | Ligand to MMP |
| EMAP II | Ligand to MMP |
| VEGF | Ligand to MMP |
| IL-1 | Ligand to MMP |
| IL-6 | Ligand to MMP |
| IL-12 | Ligand to MMP |
| PDGF | Ligand to MMP |
| PD-ECGF | Ligand to MMP |
| CXC chemokine | Ligand to MMP |
| CC chemokine | Ligand to MMP |
| C chemokine | Ligand to MMP |
| IL-15 | Ligand to MMP |
| TNF-α | Ab to MMP |
| TNF-β | Ab to MMP |
| IFN-α | Ab to MMP |
| IFN-β | Ab to MMP |
| IFN-γ | Ab to MMP |
| IL-2 | Ab to MMP |
| IL-12 | Ab to MMP |
| EMAP II | Ab to MMP |
| VEGF | Ab to MMP |
| IL-1 | Ab to MMP |
| IL-6 | Ab to MMP |
| IL-12 | Ab to MMP |
| PDGF | Ab to MMP |
| PD-ECGF | Ab to MMP |
| CXC chemokine | Ab to MMP |
| CC chemokine | Ab to MMP |
| C chemokine | Ab to MMP |
| IL-15 | Ab to MMP |
| TNF-α | Ligand to NG2 |
| TNF-β | Ligand to NG2 |
| IFN-α | Ligand to NG2 |
| IFN-β | Ligand to NG2 |
| IFN-γ | Ligand to NG2 |
| IL-2 | Ligand to NG2 |
| IL-12 | Ligand to NG2 |
| EMAP II | Ligand to NG2 |
| VEGF | Ligand to NG2 |
| IL-1 | Ligand to NG2 |
| IL-6 | Ligand to NG2 |
| IL-12 | Ligand to NG2 |
| PDGF | Ligand to NG2 |
| PD-ECGF | Ligand to NG2 |
| CXC chemokine | Ligand to NG2 |
| CC chemokine | Ligand to NG2 |
| C chemokine | Ligand to NG2 |
| IL-15 | Ligand to NG2 |
| TNF-α | Ab to NG2 |
| TNF-β | Ab to NG2 |
| IFN-α | Ab to NG2 |
| IFN-β | Ab to NG2 |
| IFN-γ | Ab to NG2 |
| IL-2 | Ab to NG2 |
| IL-12 | Ab to NG2 |
| EMAP II | Ab to NG2 |
| VEGF | Ab to NG2 |
| IL-1 | Ab to NG2 |
| IL-6 | Ab to NG2 |
| IL-12 | Ab to NG2 |
| PDGF | Ab to NG2 |
| PD-ECGF | Ab to NG2 |
| CXC chemokine | Ab to NG2 |
| CC chemokine | Ab to NG2 |
| C chemokine | Ab to NG2 |
| IL-15 | Ab to NG2 |
| TNF-α | Ligand to tenascin |
| TNF-β | Ligand to tenascin |
| IFN-α | Ligand to tenascin |
| IFN-β | Ligand to tenascin |
| IFN-γ | Ligand to tenascin |
| IL-2 | Ligand to tenascin |
| IL-12 | Ligand to tenascin |
| EMAP II | Ligand to tenascin |
| VEGF | Ligand to tenascin |
| IL-1 | Ligand to tenascin |
| IL-6 | Ligand to tenascin |
| IL-12 | Ligand to tenascin |
| PDGF | Ligand to tenascin |
| PD-ECGF | Ligand to tenascin |
| CXC chemokine | Ligand to tenascin |
| CC chemokine | Ligand to tenascin |
| C chemokine | Ligand to tenascin |
| IL-15 | Ligand to tenascin |
| TNF-α | Ab to tenascin |
| TNF-β | Ab to tenascin |
| IFN-α | Ab to tenascin |
| IFN-β | Ab to tenascin |
| IFN-γ | Ab to tenascin |
| IL-2 | Ab to tenascin |
| IL-12 | Ab to tenascin |
| EMAP II | Ab to tenascin |
| VEGF | Ab to tenascin |
| IL-1 | Ab to tenascin |
| IL-6 | Ab to tenascin |
| IL-12 | Ab to tenascin |
| PDGF | Ab to tenascin |
| PD-ECGF | Ab to tenascin |
| CXC chemokine | Ab to tenascin |
| CC chemokine | Ab to tenascin |
| C chemokine | Ab to tenascin |
| IL-15 | Ab to tenascin |
| TNF-α | Ligand to PD-ECGFR |
| TNF-β | Ligand to PD-ECGFR |
| IFN-α | Ligand to PD-ECGFR |
| IFN-β | Ligand to PD-ECGFR |
| IFN-γ | Ligand to PD-ECGFR |
| IL-2 | Ligand to PD-ECGFR |
| IL-12 | Ligand to PD-ECGFR |
| EMAP II | Ligand to PD-ECGFR |
| VEGF | Ligand to PD-ECGFR |
| IL-1 | Ligand to PD-ECGFR |
| IL-6 | Ligand to PD-ECGFR |
| IL-12 | Ligand to PD-ECGFR |

-continued

| Cytokine | Targeting Moiety |
|---|---|
| PDGF | Ligand to PD-ECGFR |
| PD-ECGF | Ligand to PD-ECGFR |
| CXC chemokine | Ligand to PD-ECGFR |
| CC chemokine | Ligand to PD-ECGFR |
| C chemokine | Ligand to PD-ECGFR |
| IL-15 | Ligand to PD-ECGFR |
| TNF-α | Ab to PD-ECGFR |
| TNF-β | Ab to PD-ECGFR |
| IFN-α | Ab to PD-ECGFR |
| IFN-β | Ab to PD-ECGFR |
| IFN-γ | Ab to PD-ECGFR |
| IL-2 | Ab to PD-ECGFR |
| IL-12 | Ab to PD-ECGFR |
| EMAP II | Ab to PD-ECGFR |
| VEGF | Ab to PD-ECGFR |
| IL-1 | Ab to PD-ECGFR |
| IL-6 | Ab to PD-ECGFR |
| IL-12 | Ab to PD-ECGFR |
| PDGF | Ab to PD-ECGFR |
| PD-ECGF | Ab to PD-ECGFR |
| CXC chemokine | Ab to PD-ECGFR |
| CC chemokine | Ab to PD-ECGFR |
| C chemokine | Ab to PD-ECGFR |
| IL-15 | Ab to PD-ECGFR |
| TNF-α | Ligand to TNFR |
| TNF-β | Ligand to TNFR |
| IFN-α | Ligand to TNFR |
| IFN-β | Ligand to TNFR |
| IFN-γ | Ligand to TNFR |
| IL-2 | Ligand to TNFR |
| IL-12 | Ligand to TNFR |
| EMAP II | Ligand to TNFR |
| VEGF | Ligand to TNFR |
| IL-1 | Ligand to TNFR |
| IL-6 | Ligand to TNFR |
| IL-12 | Ligand to TNFR |
| PDGF | Ligand to TNFR |
| PD-ECGF | Ligand to TNFR |
| CXC chemokine | Ligand to TNFR |
| CC chemokine | Ligand to TNFR |
| C chemokine | Ligand to TNFR |
| IL-15 | Ligand to TNFR |
| TNF-α | Ab to TNFR |
| TNF-β | Ab to TNFR |
| IFN-α | Ab to TNFR |
| IFN-β | Ab to TNFR |
| IFN-γ | Ab to TNFR |
| IL-2 | Ab to TNFR |
| IL-12 | Ab to TNFR |
| EMAP II | Ab to TNFR |
| VEGF | Ab to TNFR |
| IL-1 | Ab to TNFR |
| IL-6 | Ab to TNFR |
| IL-12 | Ab to TNFR |
| PDGF | Ab to TNFR |
| PD-ECGF | Ab to TNFR |
| CXC chemokine | Ab to TNFR |
| CC chemokine | Ab to TNFR |
| C chemokine | Ab to TNFR |
| IL-15 | Ab to TNFR |
| TNF-α | Ligand to PDGFR |
| TNF-β | Ligand to PDGFR |
| IFN-α | Ligand to PDGFR |
| IFN-β | Ligand to PDGFR |
| IFN-γ | Ligand to PDGFR |
| IL-2 | Ligand to PDGFR |
| IL-12 | Ligand to PDGFR |
| EMAP II | Ligand to PDGFR |
| VEGF | Ligand to PDGFR |
| IL-1 | Ligand to PDGFR |
| IL-6 | Ligand to PDGFR |
| IL-12 | Ligand to PDGFR |
| PDGF | Ligand to PDGFR |
| PD-ECGF | Ligand to PDGFR |
| CXC chemokine | Ligand to PDGFR |
| CC chemokine | Ligand to PDGFR |
| C chemokine | Ligand to PDGFR |

-continued

| Cytokine | Targeting Moiety |
|---|---|
| IL-15 | Ligand to PDGFR |
| TNF-α | Ab to PDGFR |
| TNF-β | Ab to PDGFR |
| IFN-α | Ab to PDGFR |
| IFN-β | Ab to PDGFR |
| IFN-γ | Ab to PDGFR |
| IL-2 | Ab to PDGFR |
| IL-12 | Ab to PDGFR |
| EMAP II | Ab to PDGFR |
| VEGF | Ab to PDGFR |
| IL-1 | Ab to PDGFR |
| IL-6 | Ab to PDGFR |
| IL-12 | Ab to PDGFR |
| PDGF | Ab to PDGFR |
| PD-ECGF | Ab to PDGFR |
| CXC chemokine | Ab to PDGFR |
| CC chemokine | Ab to PDGFR |
| C chemokine | Ab to PDGFR |
| IL-15 | Ab to PDGFR |
| TNF-α | Ligand to PSMA |
| TNF-β | Ligand to PSMA |
| IFN-α | Ligand to PSMA |
| IFN-β | Ligand to PSMA |
| IFN-γ | Ligand to PSMA |
| IL-2 | Ligand to PSMA |
| IL-12 | Ligand to PSMA |
| EMAP II | Ligand to PSMA |
| VEGF | Ligand to PSMA |
| IL-1 | Ligand to PSMA |
| IL-6 | Ligand to PSMA |
| IL-12 | Ligand to PSMA |
| PDGF | Ligand to PSMA |
| PD-ECGF | Ligand to PSMA |
| CXC chemokine | Ligand to PSMA |
| CC chemokine | Ligand to PSMA |
| C chemokine | Ligand to PSMA |
| IL-15 | Ligand to PSMA |
| TNF-α | Ab to PSMA |
| TNF-β | Ab to PSMA |
| IFN-α | Ab to PSMA |
| IFN-β | Ab to PSMA |
| IFN-γ | Ab to PSMA |
| IL-2 | Ab to PSMA |
| IL-12 | Ab to PSMA |
| EMAP II | Ab to PSMA |
| VEGF | Ab to PSMA |
| IL-1 | Ab to PSMA |
| IL-6 | Ab to PSMA |
| IL-12 | Ab to PSMA |
| PDGF | Ab to PSMA |
| PD-ECGF | Ab to PSMA |
| CXC chemokine | Ab to PSMA |
| CC chemokine | Ab to PSMA |
| C chemokine | Ab to PSMA |
| IL-15 | Ab to PSMA |
| TNF-α | Vitronectin |
| TNF-β | Vitronectin |
| IFN-α | Vitronectin |
| IFN-β | Vitronectin |
| IFN-γ | Vitronectin |
| IL-2 | Vitronectin |
| IL-12 | Vitronectin |
| EMAP II | Vitronectin |
| VEGF | Vitronectin |
| IL-1 | Vitronectin |
| IL-6 | Vitronectin |
| IL-12 | Vitronectin |
| PDGF | Vitronectin |
| PD-ECGF | Vitronectin |
| CXC chemokine | Vitronectin |
| CC chemokine | Vitronectin |
| C chemokine | Vitronectin |
| IL-15 | Vitronectin |
| TNF-α | Laminin |
| TNF-β | Laminin |
| IFN-α | Laminin |
| IFN-β | Laminin |

-continued

| Cytokine | Targeting Moiety |
|---|---|
| IFN-γ | Laminin |
| IL-2 | Laminin |
| IL-12 | Laminin |
| EMAP II | Laminin |
| VEGF | Laminin |
| IL-1 | Laminin |
| IL-6 | Laminin |
| IL-12 | Laminin |
| PDGF | Laminin |
| PD-ECGF | Laminin |
| CXC chemokine | Laminin |
| CC chemokine | Laminin |
| C chemokine | Laminin |
| IL-15 | Laminin |
| TNF-α | Ligand to oncofetal fibronectin |
| TNF-β | Ligand to oncofetal fibronectin |
| IFN-α | Ligand to oncofetal fibronectin |
| IFN-β | Ligand to oncofetal fibronectin |
| IFN-γ | Ligand to oncofetal fibronectin |
| IL-2 | Ligand to oncofetal fibronectin |
| IL-12 | Ligand to oncofetal fibronectin |
| EMAP II | Ligand to oncofetal fibronectin |
| VEGF | Ligand to oncofetal fibronectin |
| IL-1 | Ligand to oncofetal fibronectin |
| IL-6 | Ligand to oncofetal fibronectin |
| IL-12 | Ligand to oncofetal fibronectin |
| PDGF | Ligand to oncofetal fibronectin |
| PD-ECGF | Ligand to oncofetal fibronectin |
| CXC chemokine | Ligand to oncofetal fibronectin |
| CC chemokine | Ligand to oncofetal fibronectin |
| C chemokine | Ligand to oncofetal fibronectin |
| IL-15 | Ligand to oncofetal fibronectin |
| TNF-α | Ab to oncofetal fibronectin |
| TNF-β | Ab to oncofetal fibronectin |
| IFN-α | Ab to oncofetal fibronectin |
| IFN-β | Ab to oncofetal fibronectin |
| IFN-γ | Ab to oncofetal fibronectin |
| IL-2 | Ab to oncofetal fibronectin |
| IL-12 | Ab to oncofetal fibronectin |
| EMAP II | Ab to oncofetal fibronectin |
| VEGF | Ab to oncofetal fibronectin |
| IL-1 | Ab to oncofetal fibronectin |
| IL-6 | Ab to oncofetal fibronectin |
| IL-12 | Ab to oncofetal fibronectin |
| PDGF | Ab to oncofetal fibronectin |
| PD-ECGF | Ab to oncofetal fibronectin |
| CXC chemokine | Ab to oncofetal fibronectin |
| CC chemokine | Ab to oncofetal fibronectin |
| C chemokine | Ab to oncofetal fibronectin |
| IL-15 | Ab to oncofetal fibronectin |

It will be appreciated that in the above Table the term "Ab" represents antibody, and that the antibodies and ligands include fragments thereof.

In particularly preferred embodiments the conjugate comprises TNF-α or TNF-β and an NGR-containing peptide, or TNF-α or TNF-β and an RGD-containing peptide. In a preferred embodiment the conjugate is in the form of a fusion protein.

In another embodiment the conjugate is in the form of nucleic acid.

In another embodiment the composition further comprises another antitumor agent or diagnostic tumor-imaging compound. Preferably the further antitumor agent is doxorubicin, melphalan or cisplatin.

According to another aspect of the present invention there is provided use of a conjugate or a pharmaceutical composition according to the present invention for the preparation of a medicament for treatment or diagnosis of cancer.

In other words the present invention provides a method of treating or diagnosing cancer comprising administering to a patient in need of the same a conjugate or a pharmaceutical composition according to the present invention in an effective amount, wherein said amount does not induce a negative feedback mechanism.

Some Key Advantages of the Invention

To reach cancer cells in solid tumors, chemotherapeutic drugs must enter the tumor blood vessels, cross the vessel wall and finally migrate through the interstitium. Heterogeneous tumor perfusion, vascular permeability and cell density, and increased interstitial pressure could represent critical barriers that may limit the penetration of drugs into neoplastic cells distant to from tumor vessels and, consequently, the effectiveness of chemotherapy (1). Strategies aimed at improving drug penetration in tumors are, therefore, of great experimental and clinical interest.

A growing body of evidence suggests that Tumor Necrosis Factor-α (TNF), and inflammatory cytokine endowed with potent anti-tumor activity, could be exploited for this purpose. For example, the addition of TNF to regional isolated limb perfusion with melphalan or doxorubicin has produced higher response rates in patients with extremity soft-tissue sarcomas or melanomas than those obtained with chemotherapeutic drugs alone (2-6). TNF-induced alteration of the endothelial barrier function, reduction of tumor interstitial pressure, increased chemotherapeutic drug penetration and tumor vessel damage are believed to be important mechanisms of the synergy between TNF and chemotherapy (3, 4, 7-10). Unfortunately, systemic administration of TNF is accompanied by prohibitive toxicity, the maximum tolerated dose (8-10 μg/kg) being 10-50 times lower than the estimated effective dose (11, 12). For this reason, systemic administration of TNF has been abandoned and the clinical use of this cytokine is limited to locoregional treatmeants. Nevertheless, some features of the TNF activity, in particular the selectivity for tumor-associated vessels and the synergy with chemotherapeutic drugs, has continued to nourish hopes as regards the possibility of wider therapeutic applications (13).

The vascular effects of TNF provide the rational for developing a "vascular targeting"strategy aimed at increasing the local efficacy and at enabling systemic administration of therapeutic doses. We have shown recently that targeted delivery of TNF to tumor vessels can be achieved by coupling this protein with the CNGRC (SEQ ID NO: 5) peptide, an aminopeptidase N (CD13) ligand that targets the tumor neovasculature (14). In the present work, we have investigated whether vascular targeting with low doses of this conjugate, called NGR-TNF, could enhance the penetration of chemotherapeutic drugs in tumors and improve their efficacy. We show that systemic administration of picogram doses of NGR-TNF (3-5 ng/kg) to mice, six orders of magnitude lower than the $LD_{50}$, is sufficient to enhance the anti-tumor activity of melphalan and doxorubicin, with no evidence of increased toxicity. In addition, we provide evidence that vascular targeting with NGR-TNF can reduce drug-penetration barriers and increase the amount of doxorubicin that reach cancer cells. Finally, we show that the delivery of minute amounts of NGR-TNF to tumor vessels overcomes another major problem associated with systemic administration of relatively high doses of TNF, i.e. the induction of soluble TNF inhibitors.

DETAILED DESCRIPTION

Various preferred features and embodiments of the present invention will now be described by way of non-limiting example.

Although in general the techniques mentioned herein are well known in the art, reference may be made in particular to Sambrook et al., Molecular Cloning, A Laboratory Manual (1989) and Ausubel et al., Short Protocols in Molecular Biology (1999) 4$^{th}$ Ed, John Wiley & Sons, Inc (as well as the complete version Current Protocols in Molecular Biology).

Negative Feedback Mechanisms

Negative feedback mechanisms are known in the art and may include: soluble receptor shedding and the induction of other cytokines, hormones or biological agents at a systemic or local level such that they directly or indirectly impair the activity of the targeted cytokine of the present invention. The induction of soluble inhibitors or decoy receptors are examples of direct inhibitors. TGF-β or other anti-inflammatory cytokines may indirectly prevent the cascade of events triggered by inflammatory cytokines.

Receptor Shedding

This term relates to the ability of cells to cleave off the extracellular domain of a cytokine receptor and to release it into circulation as a soluble product. In many instances these cleavage products are still capable of binding their ligands. In contrast, however, the remaining portion of the membrane-bound receptor does not bind ligands any longer and hence the cells become desensibilised to the action of a particular cytokine. Such soluble receptors have been described for a variety of cytokines, including IL-4, 6, 6, IGF, TNF-α and IFN-γ.

Conjugate

The present invention relates to a conjugate which is a molecule comprising at least one targeting protein linked to at least cytokine formed through genetic fusion or chemical coupling. By "linked" we mean that the first and second sequences are associated such that the second sequence is able to be transported by the first sequence to a target cell. Thus, conjugates include fusion proteins in which the transport protein is linked to a cytokine via their polypeptide backbones through genetic expression of a DNA molecule encoding these proteins, directly synthesised proteins and coupled proteins in which pre-formed sequences are associated by a cross-linking agent. The term is also used herein to include associations, such as aggregates, of the cytokine with the targeting protein. According to one embodiment the second sequence may comprise a polynucleotide sequence. This embodiment may be seen as a protein/nucleic acid complex.

The second sequence may be from the same species as the first sequence, but is present in the conjugate of the invention in a manner different from the natural situation, or from a different species.

The conjugates of the present invention are capable of being directed to a cell so that an effector function corresponding to the polypeptide sequence coupled to the transport sequence can take place.

The peptide can be coupled directly to the cytokine or indirectly through a spacer, which can be a single amino acid, an amino acid sequence or an organic residue, such as 6-aminocapryl-N-hydroxysuccinimide.

The peptide ligand is preferably linked to the cytokine N-terminus thus minimising any interference in the binding of the modified cytokine to its receptor. Alternatively, the peptide can be linked to amino acid residues which are amido- or carboxylic-bond acceptors, which may be naturally occurring on the molecule or artificially inserted using genetic engineering techniques. The modified cytokine is preferably prepared by use of a cDNA comprising a 5'-contiguous sequence encoding the peptide.

According to a preferred embodiment, there is provided a conjugation product between TNF and the CNGRC (SEQ ID NO: 5) sequence in which the amino-terminal of TNF is linked to the CNGRC (SEQ ID NO: 5) peptide through the spacer G (glycine).

Cytokines

Drug penetration into neoplastic cells is critical for the effectiveness of solid-tumor chemotherapy. To reach cancer cells in solid tumors, chemotherapeutic drugs must enter the drug blood vessels, cross the vessel wall and finally migrate through the interstitium. Heterogeneous tumor perfusion, vascular permeability and cell density, and increased interstitial pressure may represent critical barriers that may limit the penetration of drugs into neoplastic cells and, consequently, the effectiveness of chemotherapy. Cytokines which have the effect of affecting these factors are therefore useful in the present invention. A non-limiting list of cytokines which may be used in the present invention is: TNFα, TNFβ, IFNα, IFNβ, IFNγ, IL-1, 2, 4, 6, 12, 15, EMAP II, vascular endothelial growth factor (VEGF), PDGF, PD-ECGF or a chemokine.

TNF

TNF acts as an inflammatory cytokine and has the effect of inducing alteration of the endothelial barrier function, reducing of tumor interstitial pressure, and increasing chemotherapeutic drug penetration and tumor vessel damage.

The first suggestion that a tumor necrotizing molecule existed was made when it was observed that cancer patients occasionally showed spontaneous regression of their tumors following bacterial infections. Subsequent studies in the 1960s indicated that host-associated (or endogenous) mediators, manufactured in response to bacterial products, were likely responsible for the observed effects. In 1975 it was shown that a bacterially-induced circulating factor had strong anti-tumor activity against tumors implanted in the skin in mice. This factor, designated tumor necrosis factor (TNF), was subsequently isolated, cloned, and found to be the prototype of a family of molecules that are involved with immune regulation and inflammation. The receptors for TNF and the other members of the TNF superfamily also constitute a superfamily of related proteins.

TNF-related ligands usually share a number of common features. These features do not include a high degree of overall amino acid (aa) sequence homology. With the exception of nerve growth factor (NGF) and TNF-beta, all ligands are synthesised as type II transmembrane proteins (extracellular C-terminus) that contain a short cytoplasmic segment (10-80 aa residues) and a relatively long extracellular region (140-215 aa residues). NGF, which is structurally unrelated to TNF, is included in this superfamily only because of its ability to bind to the TNFRSF low affinity NGF receptor (LNGFR). NGF has a classic signal sequence peptide and is secreted. TNF-β, in contrast, although also fully secreted, has a primary structure much more related to type II transmembrane proteins. TNF-β might be considered as a type II protein with a non-functional, or inefficient, transmembrane segment. In general, TNFSF members form trimeric structures, and their monomers are composed of beta-strands that orient themselves into a two sheet structure. As a consequence of the trimeric structure of these molecules, it is suggested that the ligands and receptors of the TNSF and TNFRSF superfamilies undergo "clustering" during signal transduction.

TNF-α: Human TNF-α is a 233 aa residue, nonglycosylated polypeptide that exists as either a transmembrane or soluble protein. When expressed as a 26 kDa membrane bound protein, TNF-α consists of a 29 aa residue cytoplasmic domain, a 28 aa residue transmembrane segment, and a 176 aa residue extracellular region: The soluble protein is created by a proteolytic cleavage event via an 85 kDa TNF-alpha converting enzyme (TACE), which generates a 17 kDa, 157 aa residue molecule that normally circulates as a homotrimer.

TNF-β/LT-α: TNF-β, otherwise known as lymphotoxin-α (LT-α) is a molecule whose cloning was contemporary with that of TNF-α. Although TNF-β circulates as a 171 aa residue, 25 kDa glycosylated polypeptide, a larger form has been found that is 194 aa residues long. The human TNF-β cDNA codes for an open reading frame of 205 aa residues (202 in the mouse), and presumably some type of proteolytic processing occurs during secretion. As with TNF-α, circulating TNF-β exists as a non-covalently linked trimer and is known to bind to the same receptors as TNF-α.

In one embodiment the TNF is a mutant form of TNF capable of selectively binding to one of the TNF receptors (Loetscher H et al (1993) J Biol Chem 268:26350-7; Van Ostade X et al (1993) Nature 361:266-9).

Many other inflammatory cytokines also have the property of increasing endothelial vessel permeability, and it will be appreciated that the invention can be applied to such cytokines, together with agents which increase expression of such cytokines. Inflammatory cytokines, also known as pro-inflammatory cytokines, are a number of polypeptides and glycoproteins with molecular weights between 5 kDa and 70 kDa. They have a stimulating effect on the inflammatory response. The most important inflammatory cytokines are TNF, IL-1, IL-6 and IL-8.

A Table of some cytokines classified as inflammatory cytokines is shown below:

| Inflammatory Cytokines | |
| --- | --- |
| Group | Individual cytokines |
| Endogenous cytokines | IL-1, TNF-α, IL-6 |
| Up-regulation | IL-1, TNF-α, IL-6, IFN-α, INF-β, chemokines |
| Stimulation of the production, of acute phase reactants | IL-1, IL-6, IL-11, TNF-α, INF-γ, TGF-β, LIF, OSM, CNTF |
| Chemoattractant cytokines | |
| CXC chemokines | IL-8, PF-4, PBP, NAP-2, β-TG |
| CC chemokines | MIP-1α, MIP-1β, MCP-1, MCP-2, MCP-3, RANTES |
| C chemokines | Lymphotactin |
| Stimulation of inflammatory cytokines | IL-12 |

TGF-β: transforming growth factor,
LIF: leukemia inhibitory factor;
OSM: oncostatin M;
CNTF: ciliary neurotrophic factor;
PF-4: platelet factor 4;
PBP: platelet basic protein;
NAP-2: neutrophil activating protein 2;
β-TG: β-thromboglobulin;
MIP: macrophage inflammatory protein;
MCP: monocyte chemoattractant protein.

The up-regulation of inflammatory response is also performed by IL-11, IFN-α, IFN-β, and especially by the members of the chemokine superfamily. TGF-β in some situations has a number of inflammatory activities including chemoattractant effects on neutrophils, T lymphocytes and inactivated monocytes.

IL-2

Because of the central role of the IL-2/IL-2R system in mediation of the immune and inflammatory responses, it is obvious that monitoring and manipulation of this system has important diagnostic and therapeutic implications. IL-2 has shown promise as an anti-cancer drug by virtue of its ability to stimulate the proliferation and activities of tumor-attacking LAK and TIL (tumor-infiltrating lymphocytes) cells. However, problems with IL-2 toxicity are still of concern and merit investigation. The present invention addresses this problem.

IL-15

Interleukin 15 (IL-15) is a novel cytokine that shares many biological properties with, but lacks amino acid sequence homology to, IL-2. IL-15 was originally identified in media conditioned by a monkey kidney epithelial cell line (CVI/EBNA) based on its mitogenic activity on the murine T cell line, CTLL-2. IL-15 was also independently discovered as a cytokine produced by a human adult T cell leukemia cell line (HuT-102) that stimulated T cell proliferation and was designated IL-T. By virtue of its activity as a stimulator of T cells, NK cells, LAK cells, and TILs, IL-2 is currently in clinical trials testing its potential use in treatments for cancer and for viral infections. Because of its similar biological activities, IL-15 should have similar therapeutic potential.

Chemokines

Chemokines are a superfamily of mostly small, secreted proteins that function in leukocyte trafficking, recruiting, and recirculation. They also play a critical role in many pathophysiological processes such as allergic responses, infectious and autoimmune diseases, angiogenesis, inflammation, tumor growth, and hematopoietic development. Approximately 80 percent of these proteins have from 66 to 78 amino acids (aa) in their mature form. The remainder are larger with additional as occurring upstream of the protein core or as part of an extended C-terminal segment. All chemokines signal through seven transmembrane domain G-protein coupled receptors. There are at least seventeen known chemokine receptors, and many of these receptors exhibit promiscuous binding properties whereby several different chemokines can signal through the same receptor.

Chemokines are divided into subfamilies based on conserved as sequence motifs. Most family members have at least four conserved cysteine residues that form two intramolecular disulfide bonds. The subfamilies are defined by the position of the first two cysteine residues:

The alpha subfamily, also called the CXC chemokines, have one aa separating the first two cysteine residues. This group can be further subdivided based on the presence or absence of a glu-leu-arg (ELR) as motif immediately preceding the first cysteine residue. There are currently five CXC-specific receptors and they are designated CXCR1 to CXCR5. The ELR+ chemokines bind to CXCR2 and generally act as neutrophil chemoattractants and activators. The ELR− chemokines bind CXCR3 to -5 and act primarily on lymphocytes. At the time of this writing, 14 different human genes encoding CXC chemokines have been reported in the scientific literature with some additional diversity contributed by alternative splicing.

In the beta subfamily, also called the CC chemokines, the first two cysteines are adjacent to one another with no intervening aa. There are currently 24 distinct human beta subfamily members. The receptors for this group are designated CCR1 to CCR1. Target cells for different CC family members include most types of leukocytes.

There are two known proteins with chemokine homology that fall outside of the alpha and beta subfamilies. Lymphotactin is the lone member of the gamma class (C chemokine) which has lost the first and third cysteines. The lymphotactin receptor is designated XCR1. Fractalkine, the only known member of the delta class ($CX_3C$ chemokine), has three intervening as between the first two cysteine residues. This molecule is unique among chemokines in that it is a transmembrane protein with the N-terminal chemokine domain fused to a long mucin-like stalk. The fractalkine receptor is known as $CX_3CR1$.

VEGF

The present invention is also applicable to Vasculature Endothelial Growth Factor (VEGF). Angiogenesis is a process of new blood vessel development from pre-existing vasculature. It plays an essential role in embryonic development, normal growth of tissues, wound healing, the female reproductive cycle (i.e., ovulation, menstruation and placental development), as well as a major role in many diseases. Particular interest has focused on cancer, since tumors cannot grow beyond a few millimeters in size without developing a new blood supply. Angiogenesis is also necessary for the spread and growth of tumor cell metastases.

One of the most important growth and survival factors for endothelium is VEGF. VEGF induces angiogenesis and endothelial cell proliferation and it plays an important role in regulating vasculogenesis. VEGF is a heparin-binding glycoprotein that is secreted as a homodimer of 45 kDa. Most types of cells, but usually not endothelial cells themselves, secrete VEGF. Since the initially discovered VEGF, VEGF-A, increases vascular permeability, it was known as vascular permeability factor. In addition, VEGF causes vasodilatation, partly through stimulation of nitric oxide synthase in endothelial cells. VEGF can also stimulate cell migration and inhibit apoptosis. There are several splice variants of VEGF-A. The major ones include: 121, 165, 189 and 206 amino acids (aa), each one comprising a specific exon addition.

EMAP II

Endothelial-Monocyte Activating Polypeptide-II (EMAP-II) is a cytokine that is an antiangiogenic factor in tumor vascular development, and strongly inhibits tumor growth. Recombinant human EMAP-II is an 18.3 kDa protein containing 166 amino acid residues. EMAP II has also bee found to increase endothelial vessel permeability.

PDGF

It has also been proposed that platelet-derived growth factor (PDGF) antagonists might increase drug-uptake and therapeutic effects of a broad range of anti-tumor agents in common solid tumors. PDGF is a cytokine of 30 kDA and is released by platelets on wounding and stimulates nearby cells to grow and repair the wound.

PD-ECGF

As its name suggests, platelet-derived endothelial cell growth factor (PD-ECGF) was originally isolated from platelets based on its ability to induce mitosis in endothelial cells. Its related protein is gliostatin.

Targeting Moiety

We have found that the therapeutic index of cytokines can be increased by homing of targeting the cytokine to tumor vessels. In addition, since it is known that tumor cells can form part of the lining of tumor vasculature, the present invention encompasses targeting to tumor cells directly as well as to its vasculature. Any convenient tumor or tumor vasculature, particular endothelial cell, targeting moiety may be used in the conjugate of the present invention. Many such targeting moieties are known and these and any which subsequently become available are encompassed within the scope of the present invention. In one embodiment, the targeting moiety is a binding partner, such as a ligand, of a receptor expressed by a tumor cell, or a binding partner, such as an antibody, to a marker or a component of the extracellular matrix associated with tumor cells. More particularly the targeting moiety is binding partner, such as a ligand of, a receptor expressed by tumor-associated vessels, or a binding partner, such as an antibody, to an endothelial marker or a component of the extracellular matrix associated with angiogenic vessels. The term binding partner is used here in its broadest sense and includes both natural and synthetic binding domains, including ligand and antibodies or binding fragments thereof. Thus, said binding partner can be an antibody or a fragment thereof such as Fab, Fv, single-chain Fv, a peptide or a peptido-mimetic, namely a peptido-like molecule capable of binding to the receptor, marker of extracellular component of the cell.

The following represent a non-limiting examples of suitable targeting domains and receptors/markers to which the conjugate may be targeted:

CD13

It has surprisingly been found that the therapeutic index of certain cytokines can be remarkably improved and their immunotherapeutic properties can be enhanced by coupling with a ligand of aminopeptidase-N receptor (CD13). CD13 is a trans- membrane glycoprotein of 150 kDa highly conserved in various species. It is expressed on normal cells as well as in myeloid tumor lines, in the angiogenic endothelium and is some epithelia. CD13 receptor is usually identified as "NGR" receptor, in that its peptide ligands share the amino acidic"N-GR"motif. The ligand is preferably a straight or cyclic peptide comprising the NGR motif, such as CNGRCVSGCAGRC (SEQ ID NO: 1), NGRAHA (SEQ ID NO: 2), GNGRG (SEQ ID NO: 3), cycloCVLNGRMEC (SEQ ID NO: 4) or cycloC-NGRC (SEQ ID NO: 5), or more preferably the peptide. CNGRC (SEQ ID NO: 5). Further details can be found in our WO01/61017 which is incorporated herein by reference.

TNF Receptor

As with members of the TNF Superfamily, members of the TNF Receptor Superfamily (TNFRSF) also share a number of common features. In particular, molecules in the TNFRSF are all type I (N-terminus extracellular) transmembrane glycoproteins that contain one to six ligand-binding, 40 aa residue cysteine-rich motifs in their extracellular domain. In addition, functional TNFRSF members are usually trimeric or multimeric complexes that are stabilised by intracysteine disulfide bonds. Unlike most members of the TNFSF, TNFRSF members exist in both membrane-bound and soluble forms. Finally, although an sequence homology in the cytoplasmic domains of the superfamily members does not exceed 25%, a number of receptors are able to transduce apoptotic signals in a variety of cells, suggesting a common function.

CD40: CD40 is a 50 kDa, 277 aa residue transmembrane glycoprotein most often associated with B cell proliferation and differentiation. Expressed on a variety of cell types, human CD40 cDNA encodes a 20 aa residue signal sequence, a 173 aa residue extracellular region, a 22 aa residue transmembrane segment, and a 62 aa residue cytoplasmic domain. There are four cysteine-rich motifs in the extracellular region that are accompanied by a juxtamembrane sequence rich in serines and threonines. Cells known to express CD40 include endothelial cells.

TNFRI/p55/CD120a: TNFRI is a 55 kDa, 455 aa residue transmembrane glycoprotein that is apparently expressed by virtually all nucleated mammalian cells. The molecule has a 190 aa residue extracellular region, a 25 aa residue transmembrane segment, and a 220 aa residue cytoplasmic domain. Both TNF-α and TNF-β bind to TNFRI. Among the numerous cells known to express TNFRI are endothelial cells.

TNFRII/p75/CD120b: Human TNFRII is a 75 kDa, 461 aa residue transmembrane glycoprotein originally isolated from a human lung fibroblast library. This receptor consists of a 240 aa residue extracellular region, a 27 aa residue transmembrane segment and a 173 aa residue cytoplasmic domain.

Soluble forms of TNFRII have been identified, resulting apparently from proteolytic cleavage by a metalloproteinase termed TRRE (TNF-Receptor Releasing Enzyme). The shedding process appears to be independent of that for soluble TNFRI. Among the multitude of cells known to express TNFRII are endothelial cells.

CD134L/OX40L: OX40, the receptor for OX40L, is a T cell activation marker with limited expression that seems to promote the survival (and perhaps prolong the immune response) of CD4$^+$T cells at sites of inflammation. OX40L also shows limited expression. Currently only activated CD4$^+$, CD8$^+$T cells, B cells, and vascular endothelial cells have been reported to express this factor. The human ligand is a 32 kDa, 183 aa residue glycosylated polypeptide that consists of a 21 aa residue cytoplasmic domain, a 23 aa residue transmembrane segment, and a 139 aa residue extracellular region.

VEGF Receptor Family

There are three receptors in the VEGF receptor family. They have the common properties of multiple IgG-like extracellular domains and tyrosine kinase activity. The enzyme domains of VEGF receptor 1 (VEGF R1, also known as Flt-1), VEGF R2 (also known as KDR or Flk-1), and VEGF R3 (also known as Flt-4) are divided by an inserted sequence. Endothelial cells also express additional VEGF receptors, Neuropilin-1 and Neuropilin-2. VEGF-A binds to VEGF R1 and VEGF R2 and to Neuropilin-1 and Neuropilin-2. P1GF and VEGF-B bind VEGF R1 and Neuropilin-1. VEGF-C and -D bind VEGF R3 and VEGF R2. HIV-tat and peptides derived therefrom have also been found to target the VEGFR.

PDGF Receptors

PDGF receptors are expressed in the stromal compartment in most common solid tumors Inhibition of stromally expressed PDGF receptors in a rat colon carcinoma model reduces the tumor interstitial fluid pressure and increases tumor transcapillary transport.

PSMA

Prostate specific membrane antigen (PSMA) is also an excellent tumor endothelial marker, and PSMA antibodies can be generated.

Cell Adhesion Molecules (CAMs)

Cell adhesion molecules (CAMs) are cell surface proteins involved in the binding of cells, usually leukocytes, to each other, to endothelial cells, or to extracellular matrix. Specific signals produced in response to wounding and infection control the expression and activation of certain of these adhesion molecules. The interactions and responses then initiated by binding of these CAMs to their receptors/ligands play important roles in the mediation of the inflammatory and immune reactions that constitute one line of the body's defence against these insults. Most of the CAMs characterised so far fall into three general families of proteins: the immunoglobulin (Ig) superfamily, the integrin family, or the selectin family.

A member of the Selectin family of cell surface molecules, L-Selectin consists of an NH2-terminal lectin type C domain, an EGF-like domain, two complement control domains, a 15 amino acid residue spacer, a transmembrane sequence and a short cytoplasmic domain.

Three ligands for L-Selectin on endothelial cells have been identified, all containing O-glycosylated mucin or mucin-like domains. The first ligand, GlyCAM-1, is expressed almost exclusively in peripheral and mesenteric lymph node high endothelial venules. The second L-Selectin ligand, originally called sgp90, has now been shown to be CD34. This sialomucin-like glycoprotein, often used as a surface marker for the purification of pluripotent stem cells, shows vascular expression in a wide variety of nonlymphoid tissues, as well as on the capillaries of peripheral lymph nodes. The third ligand for L-Selectin is MadCAM 1, a mucin-like glycoprotein found on mucosal lymph node high endothelial venules.

P-Selectin, a member of the Selectin family of cell surface molecules, consists of an NH2-terminal lectin type C domain, an EGF-like domain, nine complement control domains, a transmembrane domain, and a short cytoplasmic domain.

The tetrasaccharide sialyl Lewisx (sLex) has been identified as a ligand for both P- and E-Selectin, but P- E- and L-Selectin can all bind sLex and sLea under appropriate conditions. P-Selectin also reportedly binds selectively to a 160 kDa glycoprotein present on murine myeloid cells and to a glycoprotein on myeloid cells, blood neutrophils, monocytes, and lymphocytes termed P-Selectin glycoprotein ligand-1 (PSGL-1), a ligand that also can bind E-Selectin. P-Selectin-mediated rolling of leukocytes can be completely inhibited by a monoclonal antibody specific for PSLG-1, suggesting that even though P-Selectin can bind to a variety of glycoproteins under in vitro conditions, it is likely that physiologically important binding is more limited. A variety of evidence indicates that P-Selectin is involved in the adhesion of myeloid cells, as well as B and a subset of T cells, to activated endothelium.

Ig Superfamily CAMs

The Ig superfamily CAMs are calcium-independent transmembrane glycoproteins. Members of the Ig superfamily include the intercellular adhesion molecules (ICAMs), vascular-cell adhesion molecule (VCAM-1), platelet-endothelial-cell adhesion molecule (PECAM-1), and neural-cell adhesion molecule (NCAM). Each Ig superfamily CAM has an extracellular domain, which contains several Ig-like intrachain disulfide-bonded loops with conserved cysteine residues, a transmembrane domain, and an intracellular domain that interacts with the cytoskeleton. Typically, they bind integrins or other Ig superfamily CAMs. The neuronal CAMs have been implicated in neuronal patterning. Endothelial CAMs play an important role in immune response and inflammation.

In more detail, vascular cell adhesion molecule (VCAM-1, CD106, or INCAM-110), platelet endothelial cell adhesion molecule (PECAM-1/CD31) and intercellular adhesion molecules 1, 2 & 3 (ICAM-1, 2 & 3) are five functionally related CAM/IgSF molecules that are critically involved in leukocyte-connective tissue/endothelial cell interactions. Expressed principally on endothelial cells, these molecules in general regulate leukocyte migration across blood vessel walls and provide attachment points for developing endothelium during angiogenesis and are all suitable for targeting in the present invention.

Human CD31 is a 130 kDa, type I (extracellular N-terminus) transmembrane glycoprotein that belongs to the cell adhesion molecule (CAM) or C2-like subgroup of the IgSFI. The mature molecule is 711 amino acid (aa) residues in length and contains a 574 aa residue extracellular region, a 19 aa residue transmembrane segment, and a 118 aa residue cytoplasmic tail. In the extracellular region, there are nine potential N-linked glycosylation sites, and, with a predicted molecular weight of 80 kDa, it appears many of these sites are occupied. The most striking feature of the extracellular region is the presence of six Ig-homology units that resemble the C2 domains of the IgSF. Although they vary in number, the presence of these modules is a common feature of all IgSF adhesion molecules (ICAM-1, 2, 3 & VCAM-1).

Integrins

Integrins are non-covalently linked heterodimers of α and β subunits. To date, 16 α subunits and 8β subunits have been identified. These can combine in various ways to form different types of integrin receptors. The ligands for several of the integrins are adhesive extracellular matrix (ECM) proteins such as fibronectin, vitronectin, collagens and laminin. Many integrins recognise the amino acid sequence RGD (arginine-glycine-aspartic acid) which is present in fibronectin or the other adhesive proteins to which they bind. Peptides and protein fragments containing the RGD sequence can be used to modulate the activities of the RGD-recognising integrins. Thus the present invention may employ as the targeting moiety peptides recognised by integrins. These peptides are conventionally known as "RGD-containing peptides". These peptides may include peptides motifs which have been identified as binding to integrins. These motifs include the amino acid sequences: DGR, NGR and CRGDC (SEQ ID NO: 7). The peptide motifs may be linear or cyclic. Such motifs are described in more detail in the following patents which are herein incorporated by reference in relation to their description of an RGD peptides: U.S. Pat. No. 5,536,814 which describes cyclasized CRGDCL (SEQ ID NO: 8), CRGDCA (SEQ ID NO: 9) and GACRGDCLGA (SEQ ID NO: 10). U.S. Pat. No. 4,578,079 relates to synthetic peptides of formula X-RGD-T/C-Y (SEQ ID NO: 11) where X and Y are amino acids. U.S. Pat. No. 5,547,936 describes a peptide counting the sequence X-RGD-XX (SEQ ID NO: 12) where X may be an amino acid. U.S. Pat. No. 4,988,621 describes a number of RGD-counting peptides. U.S. Pat. No. 4,879,237 describes a general peptide of the formula RGD-Y (SEQ ID NO: 13) where Y is an amino acid, and the peptide G-RGD-AP (SEQ ID NO: 14). U.S. Pat. No. 5,169,930 describes the peptide RGDSPK (SEQ ID NO: 15) which binds to, av/31 integrin. U.S. Pat. No. 5,498,694 and U.S. Pat. No. 5,700,908 relate to the cytoplasmic domain of the (33 integrin sub-unit that strictly speaking is not an RGD-containing peptide; although it does contain the sequence RDG. W097/08203 describes cyclic peptides that are structural mimics or RGD-binding sites. U.S. Pat. No. 5,612,311 describes 15 RGD-containing peptides that are capable of being cyclized either by C-C linkage or through other groups such as penicillamine or mecaptopropionic acid analogs. U.S. Pat. No. 5,672,585 describes a general formula encompassing RGD-containing peptides. A preferred group of peptides are those where the aspartic acid residue of RGD is derivatised into an O-methoxy tyrosine derivative. U.S. Pat. No. 5,120,829 describes an RGD cell attachment promoting binding site and a hydrophobic attachment domain. The D form is described in U.S. Pat. No. 5,587,456. U.S. Pat. No. 5,648,330 describes a cyclic RGD-containing peptide that has high affinity for GP Iib/IIIa.

In a preferred embodiment of the present invention the targeting moiety is a ligand for αv β3 or αv β5 integrin.

Activin

Cells known to express ActRII include endothelial cells. ActRIIB expression parallels that for ActRII, and is again found in endothelial cells. Cells known to express ActRI include vascular endothelial cells. ActRIB has also been identified in endothelial cells.

Angiogenin

Angiogenin (ANG) is a 14 kDa, non-glycosylated polypeptide so named for its ability to induce new blood vessel growth.

Annexin V

Annexin V is a member of a calcium and phospholipid binding family of proteins with vascular anticoagulant activity. Various synonyms for Annexin V exist: placental protein 4 (PP4), placental anticoagulant protein I (PAP I), calphobindin I (CPB-I), calcium dependent phospholipid binding protein 33 (CaBP33), vascular anticoagulant protein alpha (VACa), anchorin CII, lipocortin-V, endonexin II, and thromboplastin inhibitor. The number of binding sites for Annexin V has been reported as 6–24×106/cell in tumor cells and 8.8×106/cell for endothelial cells.

CD44

Another molecule apparently involved in white cell adhesive events is CD44, a molecule ubiquitously expressed on both hematopoietic and non-hematopoietic cells. CD44 is remarkable for its ability to generate alternatively spliced forms, many of which differ in their activities. This remarkable flexibility has led to speculation that CD44, via its changing nature, plays a role in some of the methods that tumor cells use to progress successfully through growth and metastasis. CD44 is a 80-250 kDa type I (extracellular N-terminus) transmembrane glycoprotein. Cells known to express CD44H include vascular endothelial cells.

There are multiple ligands for CD44, including osteopontin, fibronectin, collagen types I and IV and hyaluronate. Binding to fibronectin is reported to be limited to CD44 variants expressing chrondroitin sulfate, with the chrondroitin sulfate attachment site localised to exons v8-v11. Hyaluronate binding is suggested to be possible for virtually all CD44 isoforms. One of the principal binding sites is proposed to be centred in exon 2 and to involve lysine and arginine residues. Factors other than the simple expression of a known hyaluronate-binding motif also appear to be necessary for hyaluronate binding. Successful hyaluronate binding is facilitated by the combination of exons expressed, a distinctive cytoplasmic tail, glycosylation patterns, and the activity state of the cell. Thus, in terms of its hyaluronate-binding function, a great deal of "potential" flexibility exists within each CD44-expressing cell.

Fibroblast Growth Factor (FGF)

The name "fibroblast growth factor" (FGF) is a limiting description for this family of cytokines. The function of FGFs is not restricted to cell growth. Although some of the FGFs do, indeed, induce fibroblast proliferation, the original FGF molecule (FGF-2 or FGF basic) is now known to also induce proliferation of endothelial cells, chondrocytes, smooth muscle cells, melanocytes, as well as other cells. It can also promote adipocyte differentiation, induce macrophage and fibroblast TL-6 production, stimulate astrocyte migration, and prolong neuronal survival. To date, the FGF superfamily consists of 23 members, all of which contain a conserved 120 amino acid (aa) core region that contains six identical, interspersed amino acids.

FGF-1: Human FGF-1 (also known as FGF acidic, FGFa, ECGF and HBGF-1) is a 17-18 kDa non-glycosylated polypeptide that is expressed by a variety of cells from all three germ layers. The binding molecule may be either an FGF receptor. Cells known to express FGF-1 include endothelial cells.

FGF-2: Human FGF-2, otherwise known as FGF basic, HBGF-2, and EDGF, is an 18 kDa, non-glycosylated polypeptide that shows both intracellular and extracellular activity. Following secretion, FGF-2 is sequestered on either cell surface HS or matrix glycosaminoglycans. Although FGF-2 is secreted as a monomer, cell surface HS seems to dimerize monomeric FGF-2 in a non-covalent side-to-side configuration that is subsequently capable of dimerizing and activating FGF receptors. Cells known to express FGF-2 include endothelial cells.

FGF-3: Human FGF-3 is the product of the int-2 gene [i.e., derived from integration region-2, a region on mouse chromosome 7 that contains a gene (int-2/FGF-3) accidentally activated following retroviral insertion]. The molecule is synthesised as a 28-32 kDa, 222 as glycoprotein that contains a number of peptide motifs. Cells reported to express FGF-3 are limited to developmental cells and tumors. Tumors known to express FGF-3 include breast carcinomas and colon cancer cell lines.

FGF-4: Human FGF-4 is a 22 kDa, 176 aa glycoprotein that is the product of a developmentally-regulated gene. The molecule is synthesised as a 206 aa precursor that contains a large, ill-defined 30 aa signal sequence plus two heparin-binding motifs (at aa 51-55 and 140-143). The heparin-binding sites directly relate to FGF-4 activity; heparin/heparan regulate the ability of FGF-4 to activate FGFR1 and FGFR2. Cells known to express FGF-4 include both tumor cells and embryonic cells. Its identification in human stomach cancer gives rise to one alternative designation (/hst-1/hst), while its isolation in Kaposi's sarcoma provides grounds for another (K-FGF).

IL-1R

IL-1 exerts its effects by binding to specific receptors. Two distinct IL-1 receptor binding proteins, plus a non-binding signalling accessory protein have been identified. Each have three extracellular immunoglobulin-like (Ig-like) domains, qualifying them for membership in the type IV cytokine receptor family. The two receptor binding proteins are termed type I IL-1 receptor (IL-1 RI) and type II IL-1 receptor (IL-1 RII) respectively. Human IL-1 RI is a 552 aa, 80 kDa transmembrane glycoprotein that has been isolated from endothelium cells.

RTK

The new family of receptor tyrosine kinase (RTK), the Eph receptors and their ligands ephrins, have been found to be involved in vascular assembly, angiogenesis, tumorigenesis, and metastasis. It has also been that class A Eph receptors and their ligands are elevated in tumor and associated vasculature.

MMP

Matrix metalloproteinases (MMPs) have been implicated in tumor growth, angiogenesis, invasion, and metastasis. They have also been suggested for use as tumor markers.

NG2

NG2 is a large, integral membrane, chondroitin sulfate proteoglycan that was first identified as a cell surface molecule expressed by immature neural cells. Subsequently NG2 was found to be expressed by a wide variety of immature cells as well as several types of tumors with high malignancy. NG2 has been suggested as a target molecule in the tumor vasculature. In particular, collagenase-1 (C1) is the predominant matrix metalloproteinase present in newly formed microvessels and serves as a marker of neovascularization.

Oncofetal Fibronectin

The expression of the oncofetal fragment of fibronectin (Fn-f) has also been found to be increased during angiogenesis and has been suggested as a marker of tumor angiogenesis. In one embodiment the TTM is an antibody or fragment thereof to the oncofetal ED-B domain of fibronectin. The preparation of such an antibody and its conjugation with IL-12 is described in Hahn et al (2002) Nature Biotechnology 20:264-269.

Tenascin

Tenascin is a matrix glycoprotein seen in malignant tumors including brain and breast cancers and melanoma. Its expression is malignant but not well differentiated tumors and association with the blood vessels of tumors makes it an important target for both understanding the biology of malignant tumors and angiogenesis, but is a therapeutic cancer target and marker as well.

The targeting moiety is preferably a polypeptide which is capable of binding to a tumor cell or tumor vasculature surface molecule. As well as those mentioned above other such surface molecules which are known or become available may also be targeted by the first sequence.

It will be appreciated that one can apply conventional protein binding assays to identify molecules which bind to surface molecules. It will also be appreciated that one can apply structural-based drug design to develop sequences which bind to surface molecules.

High throughput screening, as described above for synthetic compounds, can also be used for identifying targeting molecules.

This invention also contemplates the use of competitive drug screening assays in which neutralising antibodies capable of binding a target specifically compete with a test compound for binding to a target.

Binding Partner (BP)

The targeting moiety generally take the form of a binding partner (BP) to a surface molecule comprising or consisting of one or more binding domains.

Ligand

The targeting moiety of the present invention may take the form of a ligand. The ligands may be natural or synthetic. The term "ligand" also refers to a chemically modified ligand. The one or more binding domains of the BP may consist of, for example, a natural ligand for a receptor, which natural ligand may be an adhesion molecule or a growth-factor receptor ligand (e.g. epidermal growth factor), or a fragment of a natural ligand which retains binding affinity for the receptor.

Synthetic ligands include the designer ligands. As used herein, the term means "designer ligands" refers to agents which are likely to bind to the receptor based on their three dimensional shape compared to that of the receptor.

Antibodies

Alternatively, the binding domains may be derived from heavy and light chain sequences from an immunoglobulin (Ig) variable region. Such a variable region may be derived from a natural human antibody or an antibody from another species such as a rodent antibody. Alternatively the variable region may be derived from an engineered antibody such as a humanised antibody or from a phage display library from an immunised or a non-immunised animal or a mutagenised phage-display library. As a second alternative, the variable region may be derived from a single-chain variable fragment (scFv). The BP may contain other sequences to achieve multimerisation or to act as spacers between the binding domains or which result from the insertion of restriction sites in the genes encoding the BP, including Ig hinge sequences or novel spacers and engineered linker sequences.

The BP may comprise, in addition to one or more immunoglobulin variable regions, all or part of an Ig heavy chain constant region and so may comprise a natural whole Ig, an engineered Ig, an engineered Ig-like molecule, a single-chain Ig or a single-chain Ig-like molecule. Alternatively, or in addition, the BP may contain one or more domains from another protein such as a toxin.

As used herein, an "antibody" refers to a protein consisting of one or more polypeptides substantially encoded by immunoglobulin genes or fragments of immunoglobulin genes. Antibodies may exist as intact immunoglobulins or as a number of fragments, including those well-characterised fragments produced by digestion with various peptidases. While various antibody fragments are defined in terms of the digestion of an intact antibody, one of skill will appreciate that antibody fragments may be synthesised de novo either chemically or by utilising recombinant DNA methodology. Thus, the term antibody, as used herein also includes antibody fragments either produced by the modification of whole antibodies or synthesised de novo using recombinant DNA methodologies. Antibody fragments encompassed by the use of the term "antibodies" include, but are not limited to, Fab, Fab', F (ab')2, scFv, Fv, dsFv diabody, and Fd fragments.

The invention also provides monoclonal or polyclonal antibodies to the surface proteins. Thus, the present invention further provides a process for the production of monoclonal or polyclonal antibodies to polypeptides of the invention.

If polyclonal antibodies are desired, a selected mammal (e.g., mouse, rabbit, goat, horse, etc.) is immunised with an immunogenic polypeptide bearing an epitope(s). Serum from the immunised animal is collected and treated according to known procedures. If serum containing polyclonal antibodies to an epitope contains antibodies to other antigens, the polyclonal antibodies can be purified by immunoaffinity chromatography. Techniques for producing and processing polyclonal antisera are known in the art. In order that such antibodies may be made, the invention also provides polypeptides of the invention or fragments thereof haptenised to another polypeptide for use as immunogens in animals or humans.

Monoclonal antibodies directed against binding cell surface epitopes in the polypeptides can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. Panels of monoclonal antibodies produced against epitopes can be screened for various properties; i.e., for isotype and epitope affinity.

An alternative technique involves screening phage display libraries where, for example the phage express scFv fragments on the surface of their coat with a large variety of complementarity determining regions (CDRs). This technique is well known in the art.

For the purposes of this invention, the term "antibody", unless specified to the contrary, includes fragments of whole antibodies which retain their binding activity for a target antigen. As mentioned above such fragments include Fv, F(ab') and F(ab')$_2$ fragments, as the use of the term "antibodies" include, but are not limited to, Fab, Fab', F (ab')2, scFv, Fv, dsFv diabody, and Fd fragments.

The invention also provides monoclonal or polyclonal antibodies to the surface proteins. Thus, the present invention further provides a process for the production of monoclonal or polyclonal antibodies to polypeptides of the invention.

If polyclonal antibodies are desired, a selected mammal (e.g., mouse, rabbit, goat, horse, etc.) is immunised with an immunogenic polypeptide bearing an epitope(s). Serum from the immunised animal is collected and treated according to known procedures. If serum containing polyclonal antibodies to an epitope contains antibodies to other antigens, the polyclonal antibodies can be purified by immunoaffinity chromatography. Techniques for producing and processing polyclonal antisera are known in the art. In order that such antibodies may be made, the invention also provides polypeptides of the invention or fragments thereof haptenised to another polypeptide for use as immunogens in animals or humans.

Monoclonal antibodies directed against binding cell surface epitopes in the polypeptides can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. Panels of monoclonal antibodies produced against epitopes can be screened for various properties; i.e., for isotype and epitope affinity.

An alternative technique involves screening phage display libraries where, for example the phage express scFv fragments on the surface of their coat with a large variety of complementarity determining regions (CDRs). This technique is well known in the art.

For the purposes of this invention, the term "antibody", unless specified to the contrary, includes fragments of whole antibodies which retain their binding activity for a target antigen. As mentioned above such fragments include Fv, F(ab') and F(ab')$_2$ fragments, as well as single chain antibodies (scFv). Furthermore, the antibodies and fragments thereof may be humanised antibodies, for example as described in EP-A-239400.

Screens

In one aspect, the invention relates to a method of screening for an agent capable of binding to a tumor or tumor vasculature cell surface molecule, the method comprising contacting the cell surface molecule with an agent and determining if said agent binds to said cell surface molecule.

As used herein, the term "agent" includes, but is not limited to, a compound, such as a test compound, which may be obtainable from or produced by any suitable source, whether natural or not. The agent may be designed or obtained from a library of compounds which may comprise peptides, as well as other compounds, such as small organic molecules and particularly new lead compounds. By way of example, the agent may be a natural substance, a biological macromolecule, or an extract made from biological materials such as bacteria, fungi, or animal (particularly mammalian) cells or tissues, an organic or an inorganic molecule, a synthetic test compound, a semi-synthetic test compound, a structural or functional mimetic, a peptide, a peptidomimetics, a derivatised test compound, a peptide cleaved from a whole protein, or a peptides synthesised synthetically (such as, by way of example, either using a peptide synthesizer) or by recombinant techniques or combinations thereof, a recombinant test compound, a natural or a non-natural test compound, a fusion protein or equivalent thereof and mutants, derivatives or combinations thereof.

The agent can be an amino acid sequence or a chemical derivative thereof. The substance may even be an organic compound or other chemical. The agent may even be a nucleotide sequence—which may be a sense sequence or an antisense sequence.

Protein

The term "protein" includes single-chain polypeptide molecules as well as multiple-polypeptide complexes where individual constituent polypeptides are linked by covalent or non-covalent means. The term "polypeptide" includes peptides of two or more amino acids in length, typically having more than 5, 10 or 20 amino acids.

Polypeptide Homologues

It will be understood that polypeptide sequences for use in the invention are not limited to the particular sequences or fragments thereof but also include homologous sequences obtained from any source, for example related viral/bacterial proteins, cellular homologues and synthetic peptides, as well as variants or derivatives thereof. Polypeptide sequences of the present invention also include polypeptides encoded by polynucleotides of the present invention.

Polypeptide Variants, Derivatives and Fragments

The terms "variant" or "derivative" in relation to the amino acid sequences of the present invention includes any substitution of, variation of, modification of, replacement of, deletion of or addition of one (or more) amino acids from or to the sequence providing the resultant amino acid sequence preferably has targeting activity, preferably having at least 25 to 50% of the activity as the polypeptides presented in the sequence listings, more preferably at least substantially the same activity.

Thus, sequences may be modified for use in the present invention. Typically, modifications are made that maintain the activity of the sequence. Thus, in one embodiment, amino acid substitutions may be made, for example from 1, 2 or 3 to 10, 20 or 30 substitutions provided that the modified sequence retains at least about 25 to 50% of, or substantially the same activity. However, in an alternative embodiment, modifications to the amino acid sequences of a polypeptide of the invention may be made intentionally to reduce the biological activity of the polypeptide. For example truncated polypeptides that remain capable of binding to target molecule but lack functional effector domains may be useful.

In general, preferably less than 20%, 10% or 5% of the amino acid residues of a variant or derivative are altered as compared with the corresponding region depicted in the sequence listings.

Amino acid substitutions may include the use of non-naturally occurring analogues, for example to increase blood plasma half-life of a therapeutically administered polypeptide (see below for further details on the production of peptide derivatives for use in therapy).

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

Polypeptides of the invention also include fragments of the above mentioned polypeptides and variants thereof, including fragments of the sequences. Preferred fragments include those which include an epitope. Suitable fragments will be at least about 5, e.g. 10, 12, 15 or 20 amino acids in length. They may also be less than 200, 100 or 50 amino acids in length. Polypeptide fragments of the proteins and allelic and species variants thereof may contain one or more (e.g. 2, 3, 5, or 10) substitutions, deletions or insertions, including conserved substitutions. Where substitutions, deletion and/or insertions have been made, for example by means of recombinant technology, preferably less than 20%, 10% or 5% of the amino acid residues depicted in the sequence listings are altered.

Proteins of the invention are typically made by recombinant means, for example as described below. However they may also be made by synthetic means using techniques well known to skilled persons such as solid phase synthesis. Various techniques for chemical synthesising peptides are reviewed by Borgia and Fields, 2000, TibTech 18: 243-251 and described in detail in the references contained therein.

Therapeutic Peptides

Peptides of the present invention may be administered therapeutically to patients. It is preferred to use peptides that do not consisting solely of naturally-occurring amino acids but which have been modified, for example to reduce immunogenicity, to increase circulatory half-life in the body of the patient, to enhance bioavailability and/or to enhance efficacy and/or specificity.

A number of approaches have been used to modify peptides for therapeutic application. One approach is to link the peptides or proteins to a variety of polymers, such as polyethylene glycol (PEG) and polypropylene glycol (PPG)—see for example U.S. Pat. Nos. 5,091,176, 5,214,131 and U.S. Pat. No. 5,264,209.

Replacement of naturally-occurring amino acids with a variety of uncoded or modified amino acids such as D-amino acids and N-methyl amino acids may also be used to modify peptides Another approach is to use bifunctional crosslinkers, such as N-succinimidyl 3-(2 pyridyldithio) propionate, succinimidyl 6-[3-(2 pyridyldithio) propionamido] hexanoate, and sulfosuccinimidyl 6-[3-(2 pyridyldithio) propionamido]hexanoate (see U.S. Pat. No. 5,580,853).

It may be desirable to use derivatives of the peptides of the invention which are conformationally constrained. Conformational constraint refers to the stability and preferred conformation of the three-dimensional shape assumed by a peptide. Conformational constraints include local constraints, involving restricting the conformational mobility of a single residue in a peptide; regional constraints, involving restricting the conformational mobility of a group of residues, which residues may form some secondary structural unit; and global constraints, involving the entire peptide structure.

The active conformation of the peptide may be stabilised by a covalent modification, such as cyclization or by incorporation of gamma-lactam or other types of bridges. For example, side chains can be cyclized to the backbone so as create a L-gamma-lactam moiety on each side of the interaction site. See, generally, Hruby et al., "Applications of Synthetic Peptides," in Synthetic Peptides: A User's Guide: 259-345 (W. H. Freeman & Co. 1992). Cyclization also can be achieved, for example, by formation of cysteine bridges, coupling of amino and carboxy terminal groups of respective terminal amino acids, or coupling of the amino group of a Lys residue or a related homolog with a carboxy group of Asp, Glu or a related homolog. Coupling of the .alpha-amino group of a polypeptide with the epsilon-amino group of a lysine residue, using iodoacetic anhydride, can be also undertaken. See Wood and Wetzel, 1992, Int'l J. Peptide Protein Res. 39: 533-39.

Another approach described in U.S. Pat. No. 5,891,418 is to include a metal-ion complexing backbone in the peptide structure. Typically, the preferred metal-peptide backbone is based on the requisite number of particular coordinating groups required by the coordination sphere of a given complexing metal ion. In general, most of the metal ions that may prove useful have a coordination number of four to six. The nature of the coordinating groups in the peptide chain includes nitrogen atoms with amine, amide, imidazole, or guanidino functionalities; sulfur atoms of thiols or disulfides; and oxygen atoms of hydroxy, phenolic, carbonyl, or carboxyl functionalities. In addition, the peptide chain or individual amino acids can be chemically altered to include a coordinating group, such as for example oxime, hydrazino, sulfhydryl, phosphate, cyano, pyridino, piperidino, or morpholino. The peptide construct can be either linear or cyclic, however a linear construct is typically preferred. One example of a small linear peptide is Gly-Gly-Gly-Gly which has four nitrogens (an $N_4$ complexation system) in the back bone that can complex to a metal ion with a coordination number of four.

A further technique for improving the properties of therapeutic peptides is to use non-peptide peptidomimetics. A wide variety of useful techniques may be used to elucidating the precise structure of a peptide. These techniques include amino acid sequencing, x-ray crystallography, mass spectroscopy, nuclear magnetic resonance spectroscopy, computer-assisted molecular modelling, peptide mapping, and combinations thereof. Structural analysis of a peptide generally provides a large body of data which comprise the amino acid sequence of the peptide as well as the three-dimensional positioning of its atomic components. From this information, non-peptide peptidomimetics may be designed that have the required chemical functionalities for therapeutic activity but are more stable, for example less susceptible to biological degradation. An example of this approach is provided in U.S. Pat. No. 5,811,512.

Techniques for chemically synthesising therapeutic peptides of the invention are described in the above references and also reviewed by Borgia and Fields, 2000, TibTech 18: 243-251 and described in detail in the references contained therein.

Bifunctional Derivatives

A further embodiment of the invention is provided by bifunctional derivatives in which the cytokines modified with a TTM are conjugated with antibodies, or their fragments, against tumoral antigens or other tumor angiogenic markers, e.g. αv integrins, metalloproteases or the vascular growth factor, or antibodies or fragments thereof directed against components of the extracellular matrix, such as anti-tenascin antibodies or anti-fibronectin EDB domain. The preparation of a fusion product between TNF and the hinge region of a mAb against the tumor-associated TAG72 antigen expressed by gastric and ovarian adenocarcinoma has recently been reported.

A further embodiment of the invention is provided by the tumoral pre-targeting with the biotin/avidin system. According to this approach, a ternary complex is obtained on the tumoral antigenic site, at different stages, which is formed by 1) biotinylated mAb, 2) avidin (or streptavidin) and 3) bivalent cytokine modified with the TTM and biotin. A number of papers proved that the pre-targeting approach, compared with conventional targeting with immunoconjugates, can actually increase the ratio of active molecule homed at the target to free active molecule, thus reducing the treatment toxicity. This approach produced favorable results with biotinylated TNF, which was capable of inducing cytotoxicity vitro and decreasing the tumor cells growth under conditions in which normal TNF was inactive. The pre-targeting approach can also be carried out with a two-phase procedure by using a bispecific antibody which at the same time binds the tumoral antigen and the modified cytokine. The use of a bispecific antibody directed against a carcinoembryonic antigen and TNF has recently been described as a means for TNF turmoral pre-targeting.

According to a further embodiment, the invention comprises a cytokine conjugated to both a TTM and an antibody, or a fragment thereof (directly or indirectly via a boitin-avidin bridge), on different TNF subunits, where the antibody or its fragments are directed against an antigen expressed on tumor cells or other components of the tumor stroma, e.g. tenacin and fibronectin EDB domain. This results in a further improvement of the tumor homing properties of the modified cytokine and in the slow release of the latter in the tumor microenvironment through trimer-monomer-trimer transitions. The modified subunits of e.g. TNF conjugates can disassociate from the targeting complexes and reassociate so as to form unmodified trimeric TNF molecules, which then diffuse in the tumor microenvironment. The release of bioactive TNF has been shown to occur within 24-48 hours after targeting.

The preparation of cytokines in the form of liposomes can improve the biological activity thereof. It has, in fact, been observed that acylation of the TNF amino groups induces an increase in its hydrophobicity without loss of biological activity in vitro. Furthermore, it has been reported that TNF bound to lipids has unaffected cytotoxicity in vitro, immunomodulating effects and reduced toxicity in vivo.

Polynucleotides

Polynucleotides for use in the invention comprise nucleic acid sequences encoding the polypeptide conjugate of the invention. It will be understood by a skilled person that numerous different polynucleotides can encode the same polypeptide as a result of the degeneracy of the genetic code. In addition, it is to be understood that skilled persons may, using routine techniques, make nucleotide substitutions that do not affect the polypeptide sequence encoded by the polynucleotides of the invention to reflect the codon usage of any particular host organism in which the polypeptides of the invention are to be expressed.

Polynucleotides of the invention may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the present invention, it is to be understood that the polynucleotides described herein may be modified by any method available in the art. Such modifications may be carried out in order to enhance the in vivo activity or life span of polynucleotides of the invention.

Nucleotide Vectors

Polynucleotides of the invention can be incorporated into a recombinant replicable vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells include bacteria such as E. coli, yeast, mammalian cell lines and other eukaryotic cell lines, for example insect Sf9 cells.

Preferably, a polynucleotide of the invention in a vector is operably linked to a control sequence that is capable of providing for the expression of the coding sequence by the host cell, i.e. the vector is an expression vector. The term "operably linked" means that the components described are in a relationship permitting them to function in their intended manner. A regulatory sequence "operably linked" to a coding sequence is ligated in such a way that expression of the coding sequence is achieved under condition compatible with the control sequences.

The control sequences may be modified, for example by the addition of further transcriptional regulatory elements to make the level of transcription directed by the control sequences more responsive to transcriptional modulators.

Vectors of the invention may be transformed or transfected into a suitable host cell as described below to provide for expression of a protein of the invention. This process may comprise culturing a host cell transformed with an expression vector as described above under conditions to provide for expression by the vector of a coding sequence encoding the protein, and optionally recovering the expressed protein.

The vectors may be for example, plasmid or virus vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid or a neomycin resistance gene for a mammalian vector. Vectors may be used, for example, to transfect or transform a host cell.

Control sequences operably linked to sequences encoding the protein of the invention include promoters/enhancers and other expression regulation signals. These control sequences may be selected to be compatible with the host cell for which the expression vector is designed to be used in. The term "promoter" is well-known in the art and encompasses nucleic acid regions ranging in size and complexity from minimal promoters to promoters including upstream elements and enhancers.

The promoter is typically selected from promoters which are functional in mammalian cells, although prokaryotic promoters and promoters functional in other eukaryotic cells may be used. The promoter is typically derived from promoter sequences of viral or eukaryotic genes. For example, it may be a promoter derived from the genome of a cell in which expression is to occur. With respect to eukaryotic promoters, they may be promoters that function in a ubiquitous manner (such as promoters of a-actin, b-actin, tubulin) or, alternatively, a tissue-specific manner (such as promoters of the genes for pyruvate kinase). Tissue-specific promoters specific for certain cells may also be used. They may also be promoters that respond to specific stimuli, for example promoters that bind steroid hormone receptors. Viral promoters may also be used, for example the Moloney murine leukaemia virus long terminal repeat (MMLV LTR) promoter, the rous sarcoma virus (RSV) LTR promoter or the human cytomegalovirus (CMV) IE promoter.

It may also be advantageous for the promoters to be inducible so that the levels of expression of the heterologous gene can be regulated during the life-time of the cell. Inducible means that the levels of expression obtained using the promoter can be regulated.

In addition, any of these promoters may be modified by the addition of further to regulatory sequences, for example enhancer sequences. Chimeric promoters may also be used comprising sequence elements from two or more different promoters described above.

Host Cells

Vectors and polynucleotides of the invention may be introduced into host cells for the purpose of replicating the vectors/polynucleotides and/or expressing the proteins of the invention encoded by the polynucleotides of the invention. Although the proteins of the invention may be produced using prokaryotic cells as host cells, it is preferred to use eukaryotic cells, for example yeast, insect or mammalian cells, in particular mammalian cells.

Vectors/polynucleotides of the invention may introduced into suitable host cells using a variety of techniques known in the art, such as transfection, transformation and electroporation. Where vectors/polynucleotides of the invention are to be administered to animals, several techniques are known in the art, for example infection with recombinant viral vectors such as retroviruses, herpes simplex viruses and adenoviruses, direct injection of nucleic acids and biolistic transformation.

Protein Expression and Purification

Host cells comprising polynucleotides of the invention may be used to express proteins of the invention. Host cells may be cultured under suitable conditions which allow expression of the proteins of the invention. Expression of the proteins of the invention may be constitutive such that they are continually produced, or inducible, requiring a stimulus to initiate expression. In the case of inducible expression, protein production can be initiated when required by, for example, addition of an inducer substance to the culture medium, for example dexamethasone or IPTG.

Proteins of the invention can be extracted from host cells by a variety of techniques known in the art, including enzymatic, chemical and/or osmotic lysis and physical disruption.

Administration

Proteins of the invention may preferably be combined with various components to produce compositions of the invention. Preferably the compositions are combined with a pharmaceutically acceptable carrier, diluent or excipient to produce a pharmaceutical composition (which may be for human or animal use). Suitable carriers and diluents include isotonic saline solutions, for example phosphate-buffered saline. Details of excipients may be found in The Handbook of Pharmaceutical Excipients, 2nd Edn, Eds Wade & Weller, American Pharmaceutical Association. The composition of the invention may be administered by direct injection. The composition may be formulated for parenteral, intramuscular, intravenous, subcutaneous, intraocular, oral or transdermal administration. Typically, each protein may be administered at a dose of from in the range of 0.5 to 500 ng/kg, preferably in the range of 1 to 50 ng/kg, more preferably in the range of 5 to 15 ng/kg.

In an alternative aspect the present invention provides a pharmaceutical composition comprising a conjugate, wherein the conjugate is present in an amount such that the conjugate or a metabolite thereof is provided to the blood plasma of the subject to be treated in an amount of no greater than about 35,000 ng/day, preferably about 3,500 ng/day, more preferably about 1,000 ng/day.

The above dosage relate to a dosage for a 70 kg subject. A person skilled in the art would readily be able to modify the recited dosage for a subject having as mass other than 70 kg.

The dosage per day is calculated by dividing the dose to be administered to the subject by the anticipated dosage period in days. The anticipated dosage period will typically be the period until the next administration, the period over which the dose is to have effect or the period over which the dose is required to have effect.

The composition may be formulated such that administration daily, weekly or monthly will provide the desired daily dosage. It will be appreciated that the composition may be conveniently formulated for administrated less frequently, such as every 2, 4, 6, 8, 10 or 12 hours.

Polynucleotides/vectors encoding polypeptide components may be administered directly as a naked nucleic acid construct, preferably further comprising flanking sequences homologous to the host cell genome.

Uptake of naked nucleic acid constructs by mammalian cells is enhanced by several known transfection techniques for example those including the use of transfection agents. Example of these agents include cationic agents (for example calcium phosphate and DEAE-dextran) and lipofectants (for example Lipofectam™ and Transfectam™). Typically, nucleic acid constructs are mixed with the transfection agent to produce a composition.

Preferably the polynucleotide or vector of the invention is combined with a pharmaceutically acceptable carrier or diluent to produce a pharmaceutical composition. Suitable carriers and diluents include isotonic saline solutions, for example phosphate-buffered saline. The composition may be formulated for parenteral, intramuscular, intravenous, subcutaneous, intraocular or transdermal administration.

The routes of administration and dosage regimens described are intended only as a guide since a skilled practitioner will be able to determine readily the optimum route of administration and dosage regimens for any particular patient and condition.

Viral Vectors

In a preferred embodiment the conjugate is administered using a viral vector, more preferably a retroviral vector.

Retroviruses

The retroviral vector for use the present invention may be derived from or may be derivable from any suitable retrovirus. A large number of different retroviruses have been identified. Examples include: murine leukemia virus (MLV), human immunodeficiency virus (HIV), simian immunodeficiency virus, human T-cell leukemia virus (HTLV). equine infectious anaemia virus (EIAV), mouse mammary tumor virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV). A detailed list of retroviruses may be found in Coffin et al., 1997, "retroviruses", Cold Spring Harbour Laboratory Press Eds: J M Coffin, S M Hughes, H E Varmus pp 758-763.

Details on the genomic structure of some retroviruses may be found in the art. By way of example, details on HIV and Mo-MLV may be found from the NCBI Genbank (Genome Accession Nos. AF033819 and AF033811, respectively).

Retroviruses may be broadly divided into two categories: namely, "simple" and "complex". Retroviruses may even be further divided into seven groups. Five of these groups represent retroviruses with oncogenic potential. The remaining two groups are the lentiviruses and the spumaviruses. A review of these retroviruses is presented in Coffin et al., 1997 (ibid).

The lentivirus group can be split even further into "primate" and "on-primate". Examples of primate lentiviruses include human immunodeficiency virus (HIV), the causative agent of human auto-immunodeficiency syndrome (AIDS), and simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiency virus (FIV) and bovine immunodeficiency virus (BIV).

This invention also relates to the use of vectors for the delivery of a conjugate in the form of a nucleotide sequence to a haematopoietic stem cell (HSC).

Gene transfer involves the delivery to target cells, such as HSCs, of an expression cassette made up of one or more nucleotide sequences and the sequences controlling their expression. This can be carried out ex vivo in a procedure in which the cassette is transferred to cells in the laboratory and the modified cells are then administered to a recipient. Alternatively, gene transfer can be carried out in vivo in a procedure in which the expression cassette is transferred directly to cells within an individual. In both strategies, the transfer process is usually aided by a vector that helps deliver the cassette to the appropriate intracellular site.

Bone marrow has been the traditional source of HSCs for transduction, more recent studies have suggested that peripheral blood stem cells or cord blood cells may be equally good or better target cells (Cassel et al 1993 Exp Hematol 21: 585-591; Bregni et al 1992 Blood 80: 1418-1422; Lu et al 1993 J Exp Med 178: 2089-2096).

Further Anticancer Agents

The conjugate of the present invention may be used in combination with one or more other active agents, such as one or more cytotoxic drugs. Thus, in one aspect of the present invention the method further comprises administering another active pharmaceutical ingredient, such as a cytotoxic drug, either in combined dosage form with the conjugate or in a separate dosage form. Such separate cytotoxic drug dosage form may include solid oral, oral solution, syrup, elixir, injectable, transdermal, transmucosal, or other dosage form. The conjugate and the other active pharmaceutical ingredient can be combined in one dosage form or supplied in separate dosage forms that are usable together or sequentially.

Examples of cytotoxic drugs which may be used in the present invention include: the alkylating drugs, such as cyclophosphamide, ifospfamide, chlorambucil, melphalan, busulfan, lomustine, carmustine, chlormethhine (mustine), estramustine, treosulfan, thiotepa, mitobronitol; cytotoxic antibiotics, such as doxorubicin, epirubicin, aclarubicin, idarubicin, daunorubicin, mitoxantrone (mitozantrone), bleomycin, dactinomycin and to mitomycin; antimetabolites, such as methotrexate, capecitabine, cytarabine, fludarabine, cladribine, gemcitabine, fluorouracil, raltitrexed, mercaptopurine, tegafur and tioguanine; vinca alkaloids, such as vinblastine, vincristine, vindesine and vinorelbine, and etoposide; other neoplastic drugs, such as amsacrine, altretamine, crisantaspase, dacarbazine and temozolomide, hydroxycarbamide (hydroxyurea), pentostatin, platinum compounds including: carboplatin, cisplatin and oxaliplatin, porfimer sodium, procarbazine, razoxane, taxanes including: docetaxel and paclitaxel, topoisomerase I inhibitors including: irinotecan and topotecan, trastuzumab, and tretinoin.

In a preferred embodiment the further cytotoxic drug is doxorubicin, melphalan or cisplatin.

The conjugate of the present invention can also be used to use the permeability of tumor cells and vessels to compounds for diagnostic purposes. For instance, the conjugate can be used to increase the tumor uptake of radiolabelled antibodies or hormones (tumor-imaging compounds) in radioimmunoscintigraphy or radiotherapy of tumors.

FIGURES AND EXAMPLES

The present invention will further be described by reference to the following non-limiting Examples and Figures in which:

FIG. 1 Effect of mTNF and NGR-mTNF on tumor growth and body weight of animals bearing RMA-T lymphomas.

Animals bearing RMA-T tumors (5 mice/group) were treated i.p. with NGR-mTNF or mTNF at day 12 after tumor implantation (A) or at day 10, 11 and 12 (B), in two separate experiments (Exp. 1 and Exp. 2). Tumor volumes in Exp. 1 (A) and Exp. 2 (B) and animal body weight in Exp. 1 (C) 1-4 days after treatment are shown. The arrowheads in panel C indicate the time of treatment.

Figure 2:
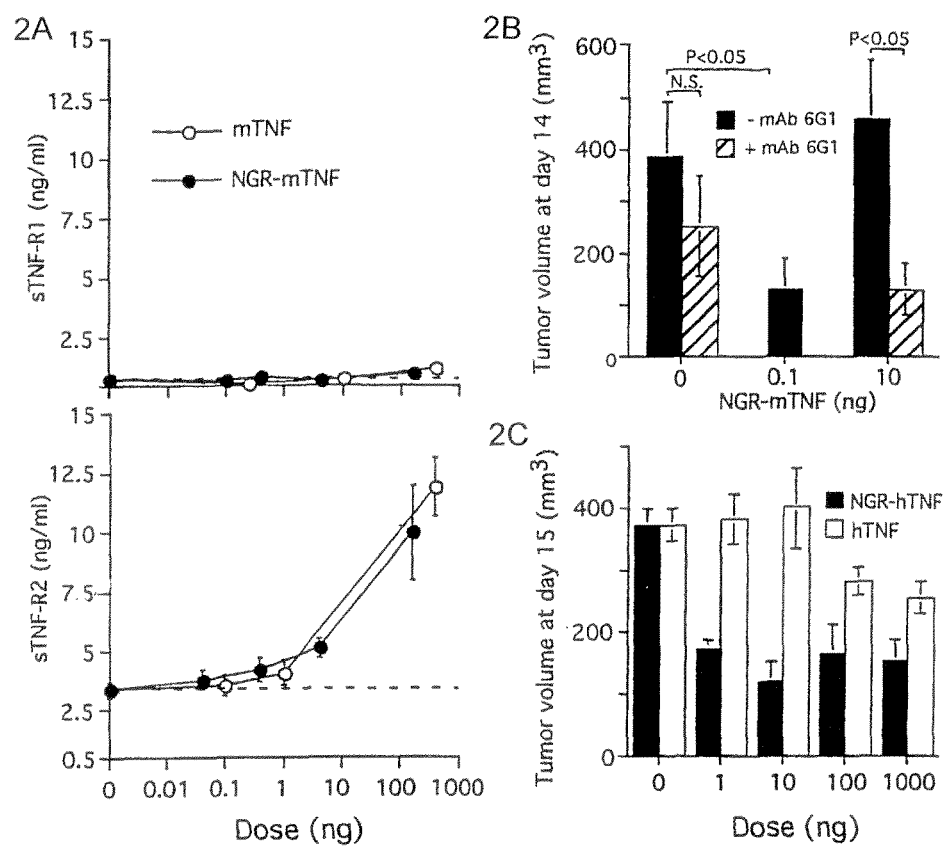

FIG. 2 Circulating levels of sTNF-R2 and their role in regulating the activity of NGR-mTNF and NGR-hTNF.

Panel A: serum levels of sTNF-R1 and sTNF-R2 in B16F1 tumor bearing mice 1 hour after treatment with various doses of NGR-mTNF or mTNF. Animals (3 mice/group) were treated at day 6.

Panel B: effect of the anti-sTNF-R2 mAb 6G1 on the anti-tumor activity of NGR-mTNF. MAb 6G1 (100 μg) was administered to animals bearing B16F1 tumors at day 5 and 8. One hour later each animal was treated with NGR-mTNF at the indicated doses, and 2 hours later with melphalan (90 μg, 5 mice/group).

Panel C: effect NGR-hTNF and hTNF on the growth of RMA-T tumors. Mice were treated with various doses of each cytokine at day 11. N.S.: not significant (t-test).

Figure 3:
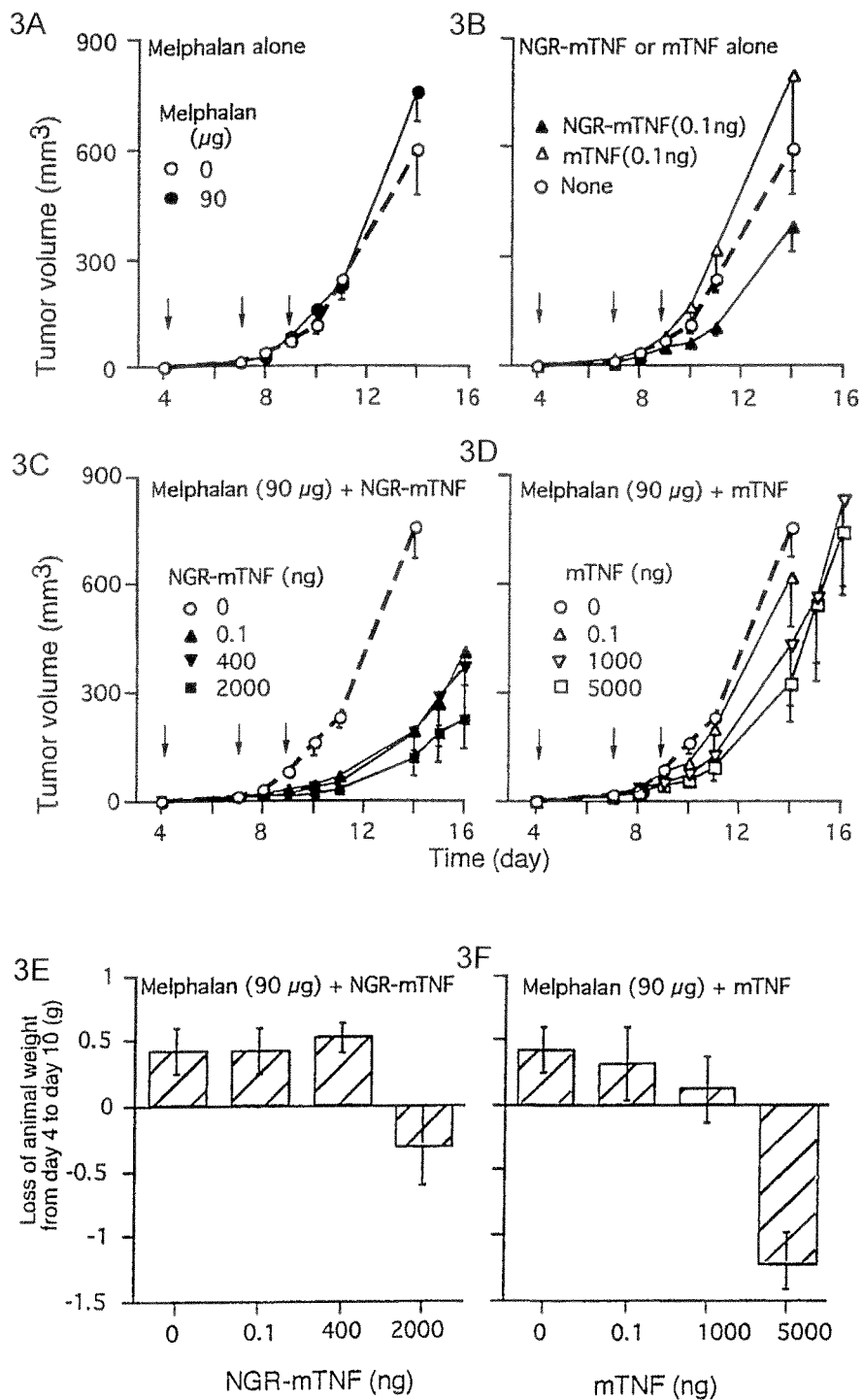

FIG. 3 Effect of melphalan, alone (A) or in combination with NGR-mTNF (C) or mTNF (D), on the tumor growth (A-D) and body weight (E-F) of mice bearing B16F1 melanoma.

The animals were treated (i.p.) with the drugs and the doses indicated in each panel (5 animals/group) at day 4, 7 and 9 after tumor implantation (indicated by arrows).

Figure 4:
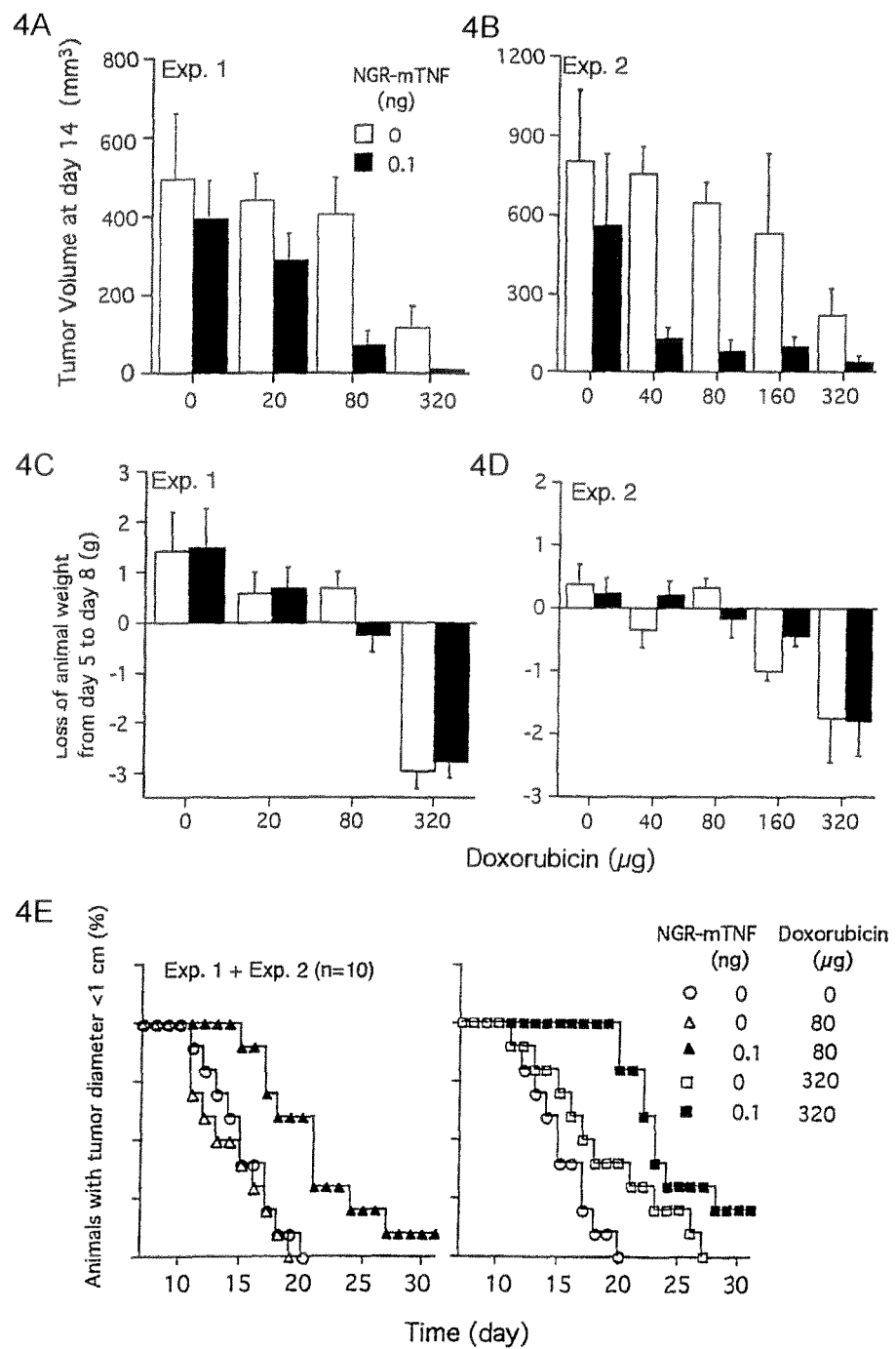

FIG. 4 Effect of various doses of doxorubicin, alone (white bars) or in combination with NGR-mTNF (black bars) on the tumor growth (A, B) body weight (C. D) and survival (E) of mice bearing B16F1 melanomas.

The drugs were administered to the animals (5 mice/group i.p.) 5 days after tumor implantation.

Figure 5:
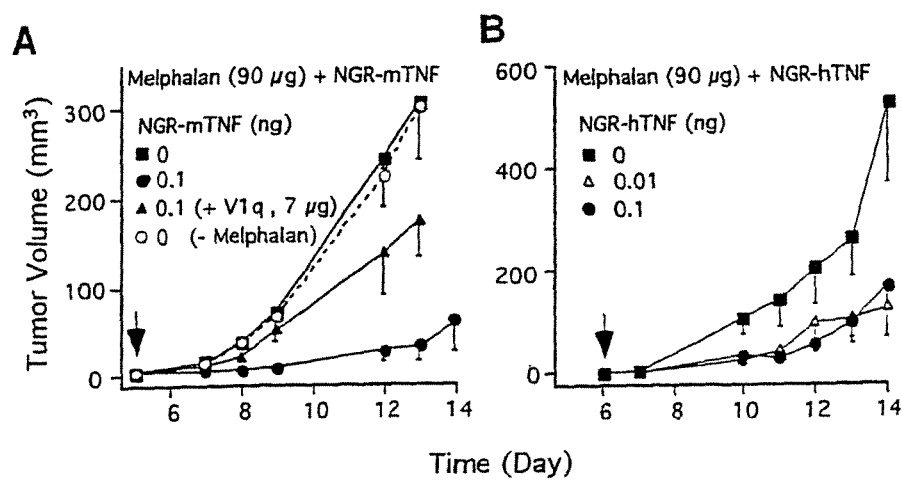

FIG. 5 Role of TNF receptors in the synergistic activity of NGR-mTNF and melphalan.

Panel A: effect of mAb V1q (an anti-mINF neutralizing antibody) on the anti-tumor activity of melphalan in combination with NGR-mTNF in the B16F1 model. The drugs were administered at day 5. Mab V1q and NGR-TNF were premixed and incubated for 1 hour before injection into animals.

Panel B: effect of melphalan in combination with NGR-hTNF at the indicated doses.

Figure 6:
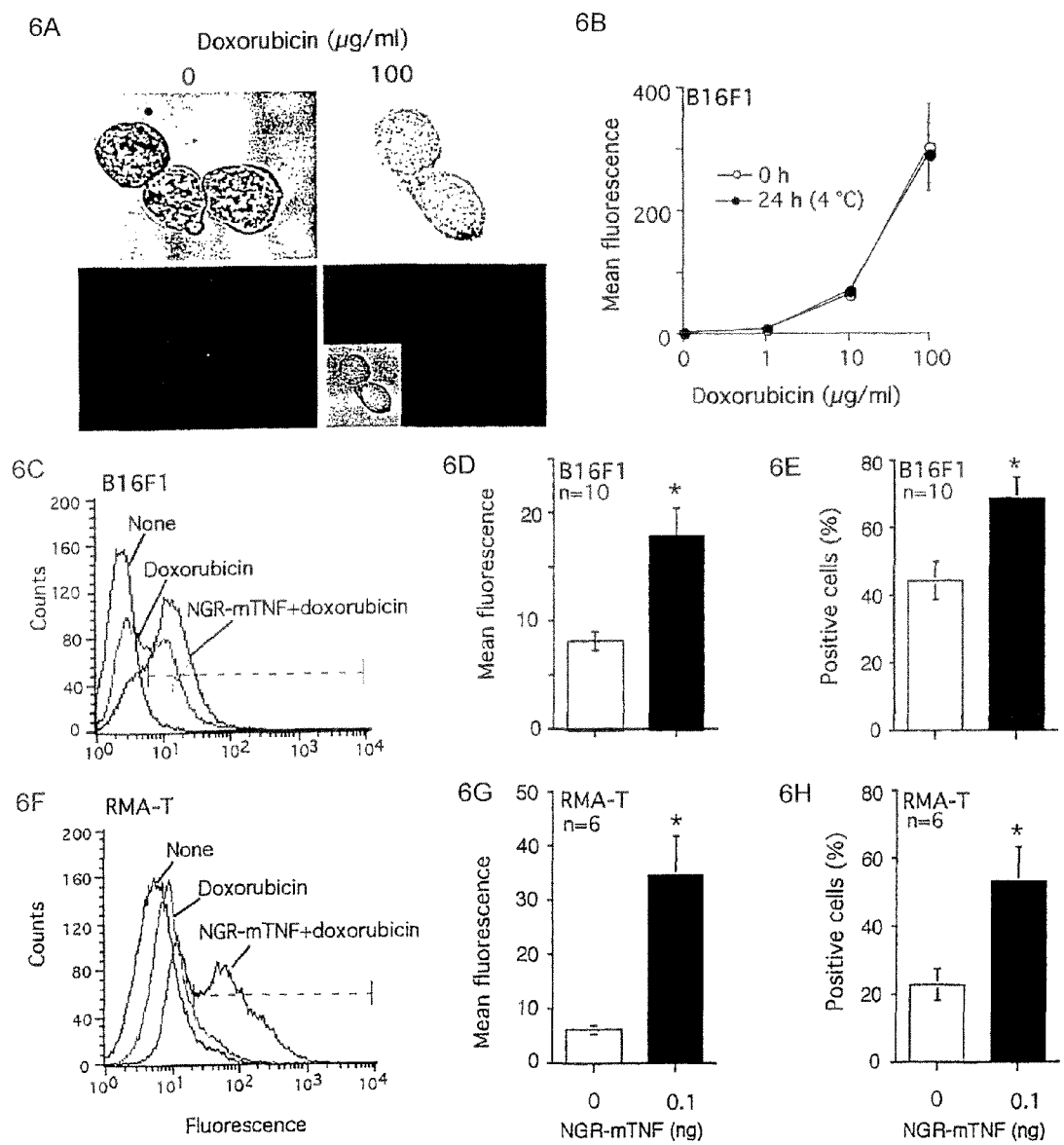

FIG. 6 Effect of NGR-mTNF on the penetration of doxorubicin in B16F1 and RMA-T tumors.

Panel A: bright field (upper panels) and fluorescence (lower panels) microscopy of B16F1 cells incubated in vitro with 100 µg/ml doxorubicin (30 min, 37° C.). Inset: merge of bright field and fluorescence images.

Panel B: stability of the B16F1 fluorescence signal after in vitro treatment with doxorubicin. B16F1 cells were incubated with various doses of doxorubicin in culture medium (30 min, 37° C.), washed with 0.9% sodium chloride, and fixed with 4% formaldehyde. The cells were then incubated for 0 hours or 24 hours in culture medium at 4° C., washed again and analyzed by FACS.

Panel C, F: representative FACS analysis of cells recovered from B16F1 (C) or RMA-T (F) tumors 2 hours after in vitro administration of doxorubicin alone (320 µg) or in combination with NGR-mTNF (0.1 ng). Dashed lines indicate the fluorescence interval considered positive.

Panel D, G: mean±SE fluorescence of B16F1 (D) or RMA-T (G) cells recovered from tumors.

Panel E, H: mean±SE of positive cells recovered from B16F1 (E) RMA-T (H) tumors.

Statistical analysis by two-tailed t-test, P<0.05 (*).

Figure 7:
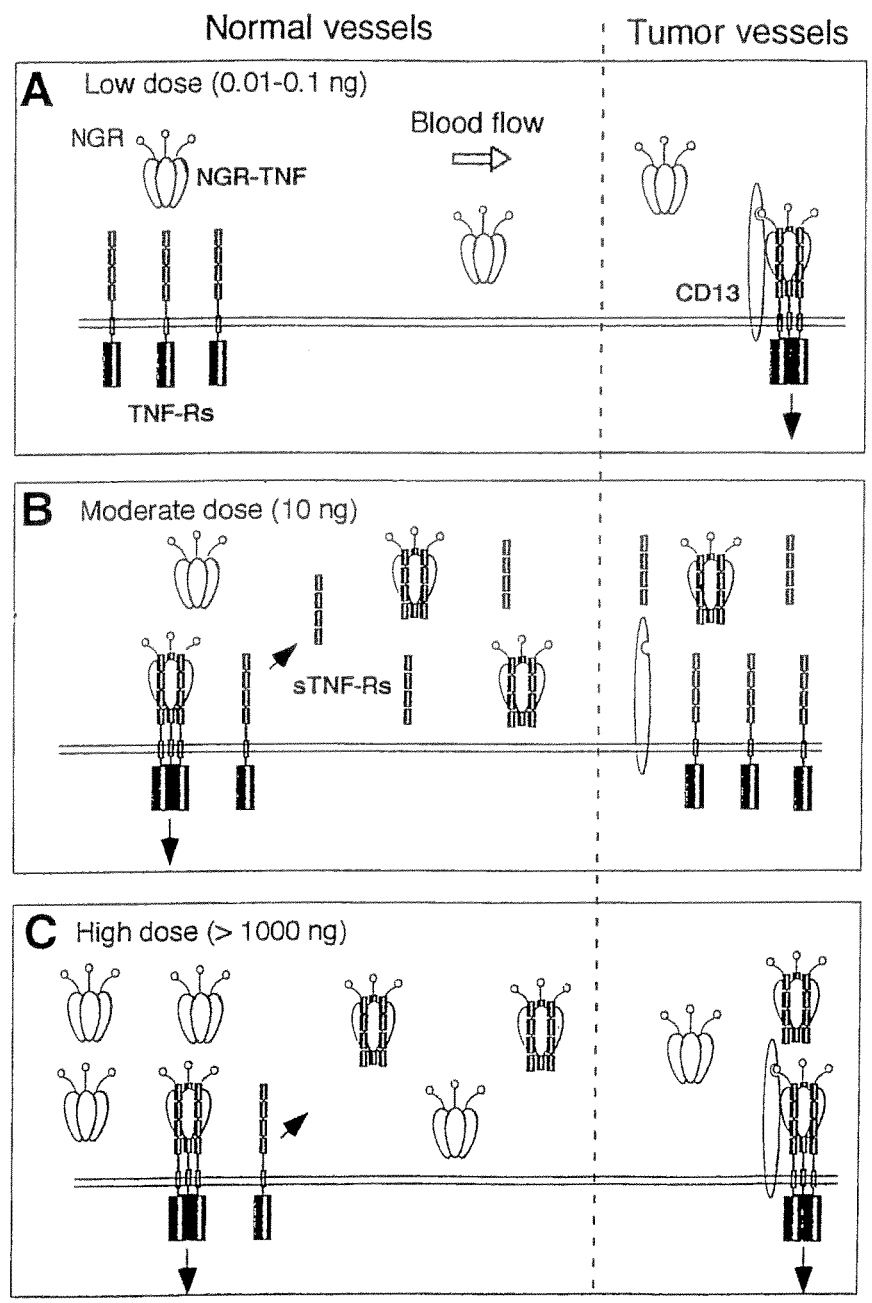

FIG. 7 Schematic representation of the hypothetical interations of low (A), moderate (B) and high (C) doses of NGR-TNF with soluble and membrane receptors in normal vessels (CD13-negative) and in tumor associated vessels (CD13-positive).

Black arrows indicate TNF receptor signalling or extracellular domain shedding.

Figure 8:
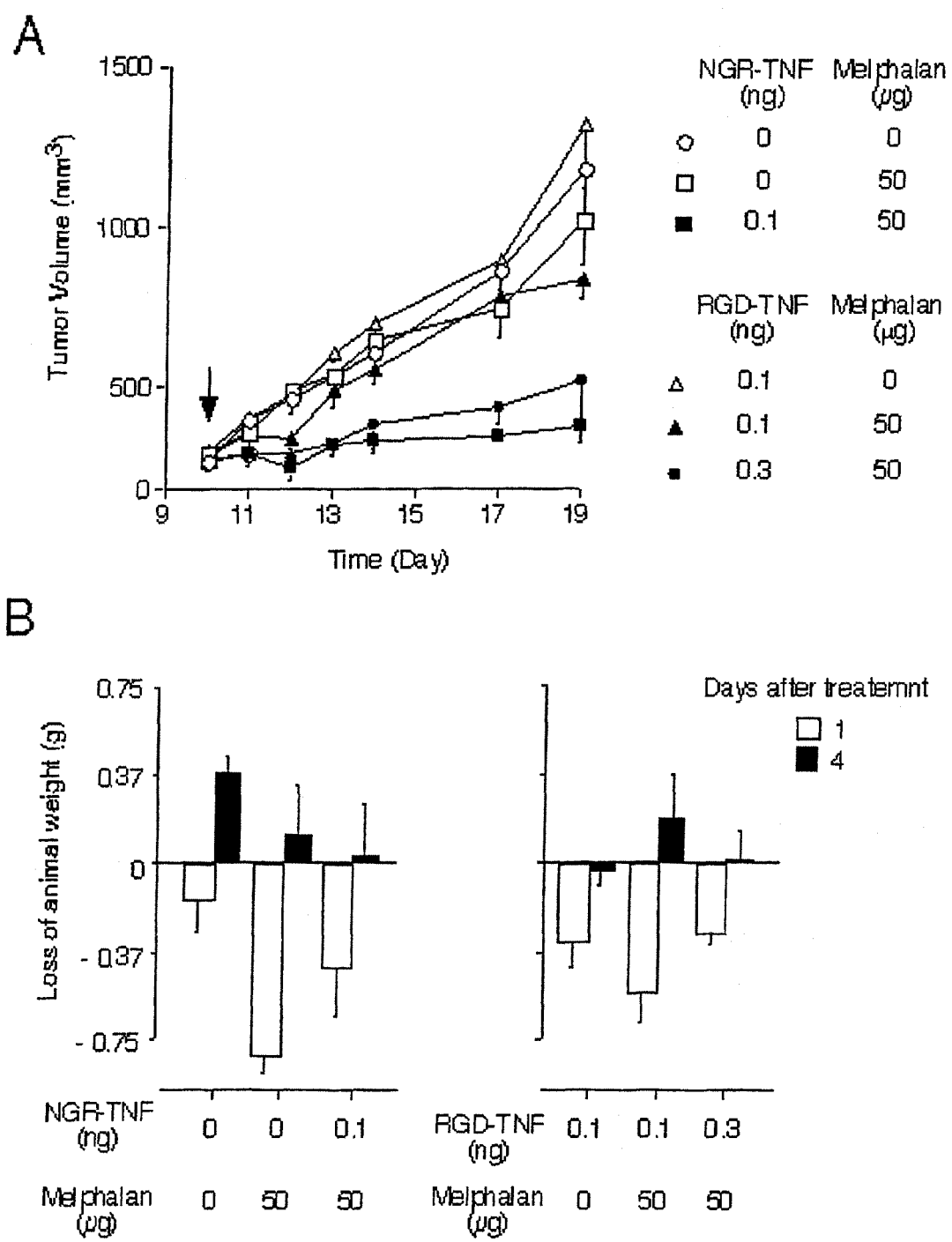

FIG. 8 Effect of RGD-TNF on the tumor growth (FIG. 8A) and body weight (FIG. 8B) of an animal bearing RMA-T.

Figure 9:
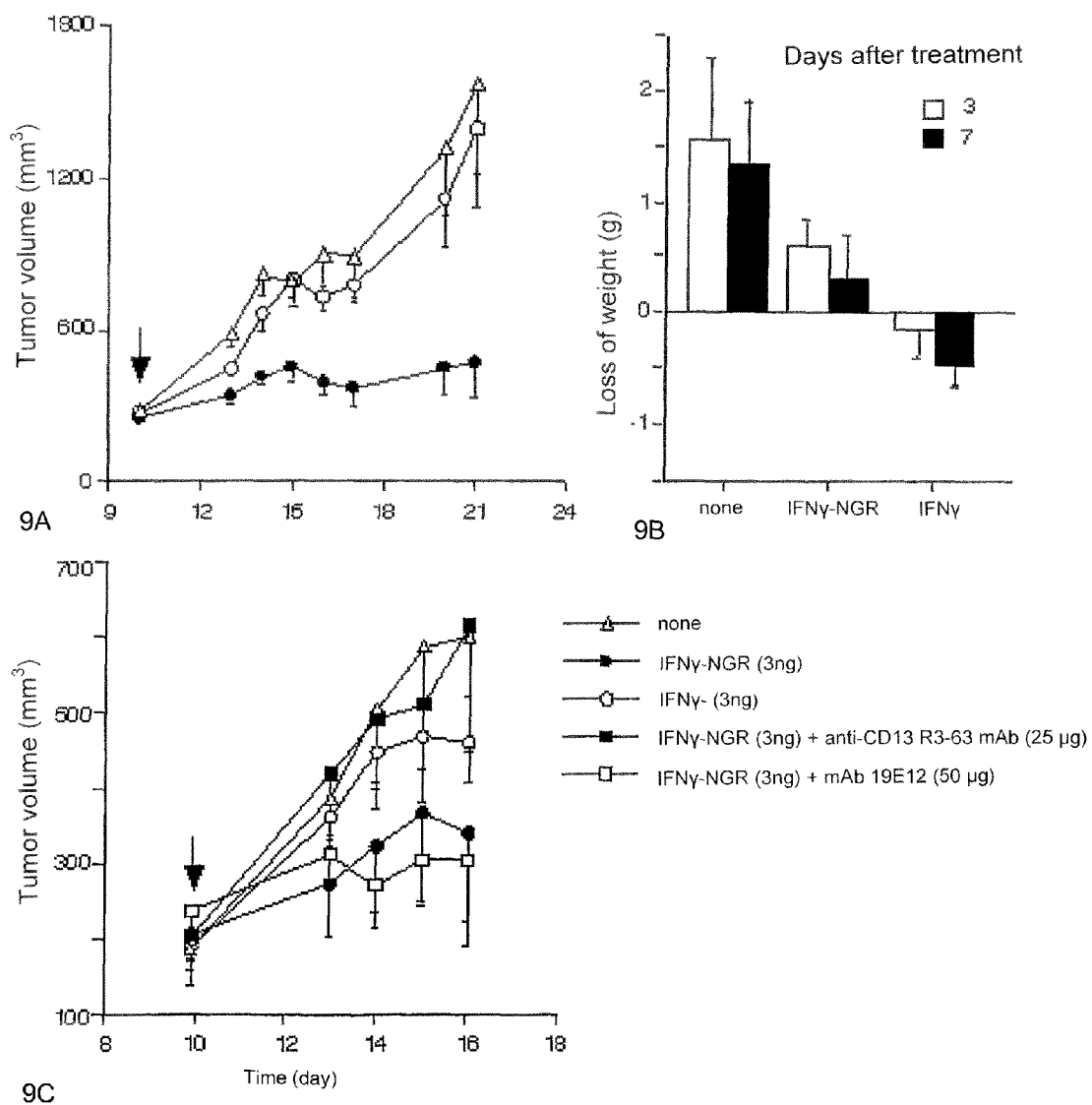

FIG. 9 Effect of a single treatement (arrow) with IFNγ-NGR on the growth of RMA lymphoma tumors in C57B6 mice (FIG. 9A & FIG. 9C) and on animal weight (FIG. 9B).

Figure 10:
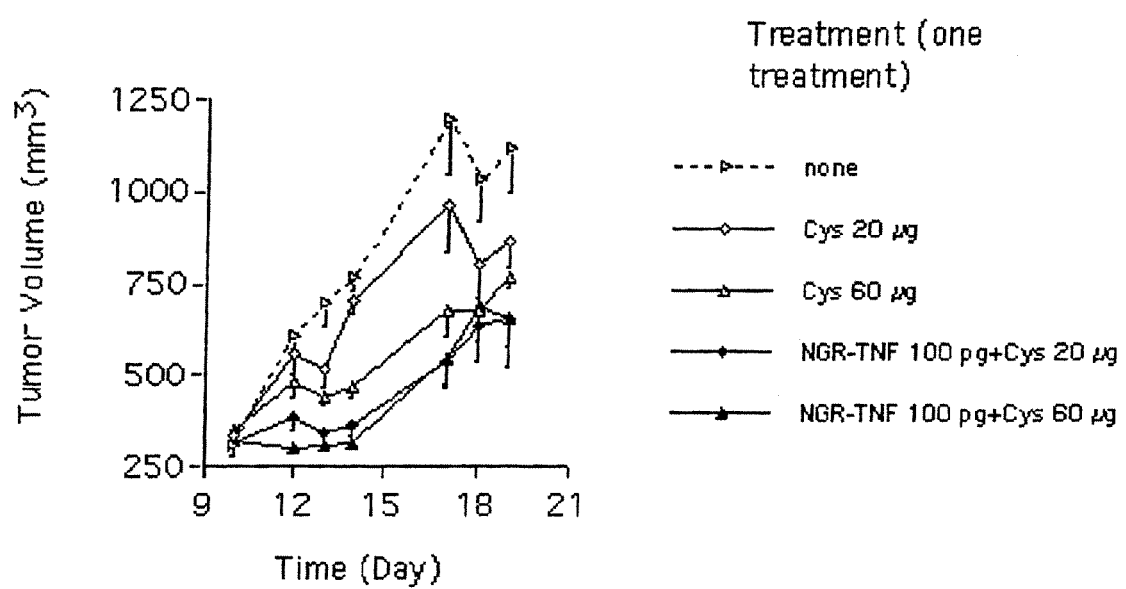

FIG. 10 Effect of NGR-TNF and cisplatinum on RMA tumors in C57/BL6 mice.

Example 1

Tumor Cell Lines and Reagents

Mouse B16F1 melanoma and RMA-T lymphoma cells were cultured as described previously (14, 15). MAb 6G1 (rat anti-p75 mTNF receptor antagonist) was produced and characterized as described previously (16, 17). MAb V1q (rat anti-mTNF) (was kindly supplied by Dr. D. Mannel (University of Regensburg, Germany). Melphalan (Alkeran) was obtained from Glaxo-Wellcome (London, Great Britain). Doxorubicin (Adriblastina) was purchased from Pharmacia-Upjohn (Milan, Italy).

Example 2

Preparation of Human and Murine TNF and NGR-TNF

Human and murine TNF and NGR-TNF (consisting of TNF fused with the C-terminus of CNGRCG (SEQ ID NO: 6)) were prepared by recombinant DNA technology and purified from *E. coli* cell extracts, as described (14). All solutions used in the chromatographic steps were prepared with sterile and endotoxin-free water (Salf, Bergamo, Italy). Protein concentration was measured with a commercial protein quantification assay kit (Pierce, Rockford, IL). The in vitro cytolytic activity of human TNF (hTNF), estimated from a standard cytolytic assay with L-M mouse fibroblasts (18), was 5.4 x $10^7$ Units/mg, whereas that of purified NGR-hTNF was 1.4 x $10^8$ Units/mg. The cytolytic activity of murine TNF (mTNF), was 7.6 x $10^7$ Units/mg, whereas that of NGR-mTNF was 9.1 x $10^7$ Units/mg. The hydrodynamic volumes of NGR-mTNF, NGR-hTNF and mTNF were similar to those of hTNF, a homotrimeric protein (19), by gel filtration chromatography on a Superdex 75 HR column (Pharmacia, Sweden). Electrospray mass spectrometry of each product determined the following molecular masses: NGR-hTNF, 17937.6 ±1.9 Da (expected for CNGRCG (SEQ ID NO: 6)-hTNF$_{1-157}$ monomers, 17939.4 Da); hTNF, 17349 ±1.3 (expected for hTNF$_{1-157}$, 17350.7); NGR-mTNF, 17841.16 ±2.5 (expected for CNGRCG (SEQ ID NO: 6)-mTNF$_{1-156}$, 17844 ±2), mTNF, 17384.9 ±2 (expected for Met-mTNF$_{1-156}$, 17386.7). The endotoxin content of each product, measured using the quantitative chromogenic limulus amoebocyte lysate (LAL) test (BioWhittaker), was: NGR-hTNF, 0.079 Units/µg; hTNF, 0.117 Units/µg; NGR-mTNF, 0.082 Units/µg; mTNF, 1.61 Units/µg.

Example 3

In vivo Studies

Studies on animal models were approved by the Ethical Committee of the San Raffaele H Scientific Institute and performed according to the prescribed guidelines. C57BL/6 mice (Charles River Laboratories, Calco, Italy) weighing 16-18 g were challenged with subcutaneous injection in the left flank of 5×10⁴ RMA-T or B16F1 living cells; 4-12 days later, the mice were treated with TNF or NGR-TNF solutions (100 µl) followed 2 hours later by administration of melphalan or doxorubicin solution (100 µl). Unless specified, all drugs were administered intraperitoneally (i.p.). All drugs were diluted with 0.9% sodium chloride, containing 100 µg/ml endotoxin-free human serum albumin (Farma-Biagini, Lucca, Italy), except for doxorubicin, which was diluted with 0.9% sodium chloride alone. Tumor growth was monitored daily by measuring the tumors with calipers as previously described (20). Animals were sacrificed before the tumors reached 1.0-1.5 cm in diameter. Tumor sizes are shown as mean±SE (5 animals/group).

Example 4

Soluble TNF Receptor Assays

Soluble p55-TNF receptor (sTNF-R1) and soluble p75-TNF receptor (sTNF-R2) in animal sera were measured using the Quantikine M kit (R & D Systems, Minneapolis, Minn. 55413).

Example 5

Detection of Doxorubicin in Tumors

C57/BL6 mice bearing B16F1 or RMA-T tumors (diameter, 0.5-1 cm) were treated with or without NGR-mTNF (0.1 ng, i.p.), followed 2 hours later by doxorubicin (320 µg, i.p.). After 2 hours the animals were sacrificed and the tumors were excised. Each tumor was weighed, disaggregated, resuspended in cold phosphate-buffered saline (PBS) and filtered through 70 µm filters. The cells were resuspended with cold PBS (50 ml), centrifuged (1500 rpm, 10 min, 4° C.), resuspended in cold PBS (2.5 ml/g of tumor tissue) and mixed with freshly prepared PBS containing 8% formaldehyde (2.5 ml/g of tissue). The cells were stored in the dark at 4° C. overnight, and then analyzed by FACS. The FACScan (Becton-Dickinson) was calibrated with cells recovered from untreated tumors. Each sample was then analyzed using the FL-3 filter and Cell Quest software.

Example 6

Dose-Response Curves of NGR-mTNF and mTNF in Murine Lymphoma and Melanoma Models The anti-tumor activity of NGR-mTNF and mTNF was first characterized in the absence of chemotherapeutic drugs. To compare the dose-response curves of NGR-mTNF and mTNF we performed several experiments based on single or repeated administration (i.p.) of various doses of NGR-mTNF and mTNF (from 0.01 to 10000 ng) to RMA-T lymphoma- or B16F1 melanoma-bearing mice. Murine TNF delayed tumor growth when adminstered at high doses (10000 ng) (FIG. 1A); no effects were induced by doses lower than 100 ng, either with single (FIG. 1A) or repeated administrations (FIG. 1B). NGR-mTNF was markedly more potent. In this case we observed anti-tumor effects even with doses as low as 0.01 ng (FIG. 1A, B). However, the dose-response curve was more complex. For instance, the effect of 10 ng was surprisingly lower than that of 0.01-0.1 ng and 1000-10000 ng. A bell-shaped dose-response curve was observed in several other experiments conducted in the RMA-T model as well as in the B16F1 melanoma model (not shown). These results suggest that 1) the efficacy of low doses of NGR-mTNF is markedly higher than that of mTNF, and 2) doses of NGR-mTNF greater than 1-10 ng activate negative feed-back mechanisms that inhibit its potential anti-tumor activity.

Example 7

Nanogram Doses of NGR-TNF, but not Picograms, Induce Soluble TNF Receptor Shedding The protective mechanisms responsible for the bell-shaped dose-response curve of NGR-mTNF were then investigated. Since exogenously administered TNF can induce soluble TNF receptor (sTNF-Rs) shedding in vivo (21), we hypothesized that the lower efficacy of 10 ng of NGR-TNF was related to induction of sTNF-R1 and/or sTNF-R2 and, consequently, to neutralization of its interation with membrane receptors.

To test this hypothesis, we measured the levels of sTNF-R1 and sTNF-R2 in the serum of tumor bearing mice collected 1 hour after administration of various doses of mTNF and NGR-mTNF. As expected, both products induced sTNF-R2 shedding, but not sTNF-R1 shedding, at doses greater than 4 ng (FIG. 2A).

To assess whether sTNF-R2 shedding regulates the activity of NGR-mTNF, we coadminstered this cytokine with mAb 6G1, an antagonist anti-sTNF-R2 antibody that prevents the binding of mTNF to soluble and membrane murine TNF-R2 (16). The anti-tumor activity of 10 ng of NGR-mTNF was potentiated by mAb 6G1 (FIG. 2B), in line with the hypothesis that sTNF-R2 plays a role in inhibiting the anti-tumor effects of NGR-mTNF.

To further support this hypothesis we compared the in vivo dose-response curve of NGR-mTNF with that of NGR-hTNF, taking advantage of the fact that the human cytokine cannot bind murine sTNF-R2 (22). We found that the dose-response curve of NGR-hTNF was not bell-shaped and that 10 ng of NGR-hTNF is as active as 1 ng (FIG. 2C). It is also remarkable that 1 ng was sufficient to induce the maximum anti-tumor effect. This may suggest that receptor binding on vessels can be achieved with very low blood levels of NGR-hTNF.

Taken together, the results of these experiments strongly suggest that NGR-mTNF and mTNF, at doses greater than 4 ng, induce shedding of sTNF-R2 in amounts sufficient to inhibit their anti-tumor activity.

Example 8

Picogram Doses of NGR-MTNF are Sufficient to Enhance the Therapeutic Effect of Melphalan and Doxorubicin We then investigated whether targeted delivery of low doses of NGR-mTNF to tumor vessles could enhance the anti-tumor activity of chemotherapeutic drugs. These experiments were conducted in the B16F1 model, a spontaneous mouse melanoma characterized by scarce immunogenicity and low sensitivity to melphalan. Melphalan (90 µg) was unable to effect the growth of tumors when injected alone (FIG. 3A). Similarly, mTNF (0.1 ng alone, i.p.) was virtually inactive, while the same dose of NGR-mTNF modestly delayed the tumor growth (FIG. 3B, upper panels). The combination of melphalan with 0.1 ng of NGR-mTNF induced stronger anti-tumor effects than the single agents, indicating a synergistic effect (FIG. 3C). Remarkably, the combination of melphalan with 0.1 ng of NGR-mTNF was more effective than the combination with 5000 ng of mTNF (FIG. 3C-D). We observed this synergisim even when NGR-mTNF (0.1 ng) was injected i.v. (not shown).

Two similar experiments were conducted with doxorubicin in the B16F1 model. Animals were treated five days after tumor implantation, with or without NGR-mTNR and, 2 hours later, with various doses of doxorubicin (20-320 µg, i.p.). In both experiments, the effect of doxorubicin plus NGR-mTNF was stronger than that of doxorubicin alone (FIG. 4A, B, E), indicating that NGR-mTNF markedly improves the efficacy of this drug. For example, the effect of doxorubicin (40 µg) plus NGR-mTNF (0.1 ng) was, stronger than that of 320 µg of doxorubicin alone (FIG. 4B), while, the effect of doxorubicin (20 µg) plus NGR-mTNF was lower (FIG. 4A). From these results we estimate that the activity of doxorubicin is potentiated 8-10 fold by NGR-mTNF.

In conclusion, these results suggest that picogram doses of NGR-TNF are sufficient to improve the response of tumors to both melphalan and doxorubicin.

Example 9

Low Doses of NGR-mTNF are not Toxic and do not Increase the Toxicity of Melphalan To estimate the efficacy/toxicity ratio of each treatment, we monitored the animal body weight daily and animal survival after treatment. While therapeutic doses of mTNF (10000 ng) induced marked loss of body weight in RMA-T bearing animals (FIG. 1C, left), therapeutic doses of NGR-mTNF (0.01-1 ng) did not cause loss of body weight (FIG. 1C, right). Moreover, neither NGR-mTNF nor mTNF (1 ng each) increased the lethality of 200 μg of melphalan in mice bearing the RNA-T tumor (Table 1).

TABLE 1

Effect of mTNF and NGR-mTNF on the toxicity of Melphalan (high dose) in tumor-bearing mice[a]

| Treatment | No. of mice alive 3 days after treatment |
|---|---|
| None | 5/5 (100%) |
| Melphalan | 7/10 (70%) |
| Melphalan + mTNF | 8/10 (80%) |
| Melphalan + NGR-mTNF | 8/10 (80%) |

[a]C57BL6 mice, bearing 11-day old tumors, were treated (i.p.) with 1 ng of NGR-mTNF or mTNF and, 2 hours later, with 200 μg of melphalan.

In the B16F1 model, therapeutic doses of NGR-mTNF (0.1 ng) did not cause loss of body weight, even when combined with melphalan (FIG. 3E). In contrast, melphalan combined with therapeutic doses of mTNF (5 μg) induced marked loss of body weight (FIG. 3F). In addition, NGR-mTNF (0.1 ng) did not increase the loss of body weight causes by high doses of doxorubicin (FIG. 4C-D).

These results suggest that picogram doses of NGR-mTNF increase the response of tumors to melphalan and doxorubicin with no evidence of increased toxicity.

Example 10

TNF-R1 Activation is Necessary and Sufficient for the Synergism Between NGR-TNF and Chemotherapeutic Drugs The mechanisms of the synergism between low doses of NGR-mTNF and chemotherapy were then investigated.

To assess whether these mechanisms rely on TNF-Rs activation we tested the effect of mAbV1q, a neutralizing anti-mTNF antibody, on the anti-tumor activity of NGR-mTNF (0.1 ng) in combination with melphalan (90 μg). MAb V1q inhibited, at least partially, the anti-tumor activity of these drugs in the B16F1 model (FIG. 5A). This suggests that the interaction between the TNF moity and TNF-Rs is critical for the activity of the conjugate.

The role of TNF-R1 and TNF-R2 was then studied. To this end, we evaluated the effect of melphalan in combination with 0.01 ng or 0.1 ng of NGR-hTNF, a TNF-R1 specific agonist (22). The effect of melphalan in the B16F1 model was potentiated by NGR-hTNF (FIG. 5B) suggesting that TNF-R1 activation is sufficient for the synergism.

Example 11

The Synergy Between NGR-TNF and Chemotherapy is not Dependent on Tumor Cell Cytotoxicity To assess whether the synergism depends directly on cytotoxicity against tumor cells we measured the effect of each compound, alone or in combination, on cultured B16F1 cells. Neither melphalan or NGR-mTNF, alone or in combination, killed these cells in a 48 hour in vitro assay (not shown). Similarly, NGR-mTNF did not enhance the cytotoxic activity of doxorubicin in vitro (not shown). These results suggest that the synergism observed in vivo is not directly dependent on cytotoxic effects against tumor cells and points to an indirect role of a component of the tumor stroma, e.g. the endothelial lining of tumor vessels.

Example 12

NGR-TNF Increases the Penetration of Doxorubicin in Murine Melanomas and Lymphomas We then investigated whether NGR-mTNF could increase the penetration of chemotherapeutic drugs in tumors. To this aim we measured the amount of doxorubicin that had penetrated B16F1 and RMA-T tumors, 2 hours after administration, taking advantage from the fluorescent properties of this drug (23). Preliminary experiments showed that the nuclei of B16F1 cells become fluorescent after these cells are exposed to doxorubicin in vitro (FIG. 6A). The fluorescence signal is dose-dependent and stable for at least 24 hours, when the cells are fixed with formaldehyde and kept at 4° C., as measured by FACS (FIG. 6B). Thus, the fluorescence intensity of tumor cells recovered from animals after treatment is an indication of the amount of doxorubicin that has penetrated tumors. We observed that 0.1 ng of NGR-mTNF, administered 2 hours before doxorubicin, increased the fluorescence intensity and the percentage of positive cells recovered from both B16F1 and RMA-T tumors, 2 hours after treatment (2-5-fold, FIG. 6C-H). This suggests that NGR-mTNF increased the number of cells that were reached by doxorubicin as well as the intracellular amount of drug.

Example 13

Effect of RGD-TNF on Tumors

C57/BL6 mice bearing RMA-T tumors (5 mice/group) were treated intraperitoneally with melphalan alone, or in combination with RGD-TNF or NGR-TNF. The effect on tumor volume is shown in FIG. 8A and the effect on animal weight is shown in FIG. 8B. These results demonstrate that RGD-TNF is also active in the picogram range.

Example 14

Effect of IFNγ-NGR on Tumors

C57/BL6 mice bearing RMA lymphoma tumors were treated with or without IFNγ (3 ng) or IFNγ-NGR (3 ng). After 21 days the animals were sacrificed. The results of tumor volume and of animal weight loss can be seen in FIGS. 9A and 9B. In addition, C57/BL6 mice bearing RMA lymphoma tumors were treated with or without IFNγ (3 ng), IFNγ-NGR (3 ng), IFNγ-NGR (3 ng) plus anti-CD13 R3-63 mAb (25 μg) or IFNγ-NGR (3 ng) plus mAB 19E12 (50 μg). The mAB 19E12 is an irrelevant IgG used as a negative control in the experiment. The results demonstrate that IFNγ-NGR is active in the picogram range.

Example 15

Picogram Doses of NGR-TNF are Sufficient to Enhance the Therapeutic Effect of Cisplatinum We investigated whether targeted delivery of low doses of NGR-TNF to tumor vessels could enhance the anti-tumor activity of the anti-cancer drug, cisplatinum. These experiments were carried out in C57/BL6/N mice bearing RMA-T tumors of initial age 8 weeks. The mice were treated with or without cisplatinum or NGR-mTNF with treatment at day 10. The results are shown in FIG. 10. In this figure, Cys=Cisplatino Teva solution 0.5 mg/ml; NGR=NGR-mTNF. The diluent was HAS 100 mg/ml in NaCl 0.9%. The results suggest that picogram doses of NGR-TNF are sufficient to enhance the therapeutic effect of cisplatinum.

Summary of Advantages

Alteration of vascular permeability and interstitial pressure, endothelial cell damage and fibrin deposition are important mechanisms for the anti-tumor activity of TNF, either alone or in combination with chemotherapeutic drugs. After, infusion in animals or patients TNF can also induce negative feedback mechanisms that neutralize most of these effects. For example, TNF, even at moderate doses, can induce the release of soluble p55 and p75 TNF receptors that may prevent its interation with membrane receptos (21, 24). Although these soluble inhibitors may protect the body from the harmful effects of this cytokine, they may also prevent its anti-tumor activity and could explain, in part, the need of high doses of TNF for effective therapy. In this work we postulated that homing low doses of TNF to tumor vessels represents a new strategy to avoid toxic reactions as well as negative feedback mechanisms, while preserving its synergism with chemotherapy. To verify this hypothesis, we have investigated the anti-tumor activity of high and low doses of NGR-mTNF and mTNF, ranging from picogram to microgram quantities, in two murine models based on subcutaneous RMA-T lymphoma and B16F1 melanoma tumors. The study was carried out using these cytokines alone or in combination with melphalan or doxorubicin. While mTNF was virtually inactive in these models at lower doses than 100-1000 ng, we found that NGR-mTNF, even alone, could induce anti-tumor effects with doses as low as 0.01-0.1 ng. Since the $LD_{50}$ values of mTNF and NGR-mTNF are similar and correspond to about 50,000 ng in RMA-T tumor-bearing mice (14), these results indicate that the efficacy/toxicity ratio of NGR-mTNF is $10^4$-$10^5$ times greater than that of mTNF.

Administration of minute amounts of NGR-mTNF (0.1 ng) to tumor-bearing animals potentiated the anti-tumor activity of melphalan and doxorubicin with no evidence of increased toxicity, as judged by tumor mass reduction, animal survival and weight loss after treatment. This suggests that NGR-mTNF improves the therapeutic index of these drugs. It is noteworthy that $5\times10^4$-fold greater doses of mTNF were necessary to enhance the effect of melphalan to comparable levels, causing marked loss of body weight.

The fact that both melphalan and doxorubicin at doses virtually inactive in the B16F1 model reduced tumor growth when combined with NGR-mTNF indicates that these drugs act synergistically. Studies on the mechanism of action showed that the synergism relies on the interaction of NGR-mTNF with TNF-R1 on stromal cells, most likely endothelial cells, and much less on tumor cells. In addition, we found that vascular targeting with NGR-mTNF improves cytotoxic drug penetration in tumors. Noteworthy, NGR-mTNF increased both the percentage of cancer cells that can be reached by doxorubicin in 2 hours as well as the intracellular amount of drug, suggesting that NGR-TNF can alter drug-penetration barriers. Previous studies showed that TNF can rapidly increase endothelial permeability (25, 26), and can decrease interstitial fluid pressure (8) that are believed to be important barriers for drug penetration in tumors (1). Possibly, these mechanisms increase convective transport of drugs through the tumor vessel wall and interstitium, finally resulting in increased drug uptake by tumor cells. The timing of administration is likely critical for these mechanisms, as TNF can also induce intravascular coagulation (27) leading to vessel occlusion and reduction of tumor perfusion. According to this view, we observed that the effect of melphalan was higher when this drug was administered 2 hours after NGR-TNF than after 6 hours (data not shown).

The hypothesis that vascular targeting could avoid negative feedback mechanisms, usually associated with TNF therapy, is supported by the observation that picogram doses of NGR-mTNF do not induce soluble receptor shedding, while both NGR-mTNF and mTNF rapidly induce the release of sTNF-R2 into the circulation at doses greater than 4-10 ng. These levels of sTNF-R2 inhibited most of the anti-tumor activity of 10 ng of NGR-mTNF and may explain the paradoxical observation that 10 ng is less active than 0.1 ng. Likely, a large proportion of injected molecules were rapidly complexed by sTNF-Rs and their activity was blocked.

The molecular mechanisms underlying the selective interaction of low doses of NGR-mTNF with tumor blood vessels has been partially elucidated. We have shown recently that different CD13 isoforms are expressed in tumor-associated vessels, in epithelia and in myeloid cells, and that the NGR domain of NGR-TNF selectively recognizes a CD13 isoform associated with tumor vessels (28). We hypothesize, therefore, that low blood levels of NGR-mTNF can rapidly interact with CD13-positive endothelial cells because of high-avidity multivalent binding involving both CD13 and TNF-Rs, and little or not at all with CD13-negative endothelial cells of normal vessels, because of lower avidity. A schematic representation of these concepts and of the hypothetical interactions of NGR-TNF with soluble and membrane receptors is shown in FIG. 7.

We have also found that RGD-TNF and IFNγ-NGR are active in the picogram range. We have also shown that NGR-TNF increases the effect of cisplatinum.

In conclusion, we have found that targeted delivery of picogram doses of cytokines to tumor vessels enhances the anti-tumor activity of chemotherapeutic drugs in mice without inducing soluble receptor shedding. Given that the CNGRC (SEQ ID NO: 5) motif is expected to target murine as well as human tumor associated vessels (29), our results suggest that the combination of low doses of targeted cytokines with anti-cancer drugs could increase their therapeutic index in human patients.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments.

Indeed, various modifications of the described modes for carrying out the invention which are apparent to those skilled in molecular biology or related fields are intended to be within the scope of the following claims.

REFERENCES

1. Jain, R. K. 1994. *Sci Am.* 271:58-65.
2. Lienard, D., et al. 1992 *J. Clin. Oncol.* 10:52-60.
3. Eggermont, A. M., et al. 1996. *J. Clin. Oncol.* 14:2653-2665.
4. Lejeune, F. J. 1995. *Eur. J. Cancer.* 31A:1009-1016.
5, Fraker, D. L., et al. 1996. *J. Clin. Oncol.* 14:479-489.
6. Rossi, C. R., et al. 1999. *Cancer.* 86:1742-1749.
7. van der Veen, A. H., et al. 2000. *Br. J. Cancer.* 82:973-980.
8. Kristensen, C. A., et al. 1996. *Br. J. Cancer.* 74:533-536.
9. Suzuki, S., et al. 1990. *Int. J. Cancer.* 46:1095-1100.
10. de Wilt, J. H., et al. 2000. *Br. J. Cancer.* 82:1000-1003.
11. Fiers, W. 1995. Biologic therapy with TNF: preclinical studies. In Biologic therapy of cancer: principles and practice. V. De Vita, S. Hellman, and S. Rosenberg, editors. J.B. Lippincott Company, Philadelphia. 295-327.
12. Fraker, D. L., H. R. Alexander, and H. I. Pass. 1995. Biologic therapy with TNF: systemic administration and isolation-perfusion. In Biologic therapy of cancer: principles and practice. V. De Vita, S. Hellman and S. Rosenberg, editors. J.B. Lippincott Company, Philadelphia 329-345.
13. Corti, A., and F. Marcucci. 1998. *J. Drug Targ.* 5:403-413.
14. Curnis, F., A et al. 2000. *Nat. Biotechnol.* 18:1185-1190.
15. Moro, M., et al. 1997. *Cancer Res.* 57:1922-1928.
16. Corti, A., et al. 1999. *Infect Immun.* 67:5762-5767.
17. Pelagi, M., et al. 2000. *Eur. Cytokine Net.* 11:580-588.
18. Corti, A., et al. 1994. *J. Immunol. Meth.* 177:191-198.
19. Smith, R. A., and C. Baglioni. 1987. *J. Biol. Chem.* 262:6951-6954.
20. Gasparri, A., et al. 1999. *Cancer Res.* 59:2917-2923.
21. Aderka, D., et al. 1998. *J. Clin. Invest.* 101:650-659.
22. Tartaglia, L. A., et al. 1991. *Proc. Natl. Acad. Sci. USA.* 88:9292-9296.
23. Luk, C. K., and I. F. Tannock. 1989. *J. Natl. Cancer Inst.* 81:55-59.
24. Sella, A., et al. 1995. *Cancer Biother.* 10:225-235.
25. Brett, J., et al. 1989. *J. Exp. Med.* 169:1977-1991.
26. Goldblum, S. E., and W. L. Sun. 1990. *Am. J. Physiol.* 258:L57-67.
27. Clauss, M., et al. 1992. Modulation of endothelial cell hemostatic properties by TNF: insights into the role of endothelium in the host response to inflammatory stimuli. In Tumour necrosis factors: the molecules and their emerging roles in medicine. B. Beutler, editor, Raven Press, New York. 49-63.
28. Curnis, F., et al. 2002. *Cancer Res.*:62:867-874.
29. Arap, W., et al. 1998. *Science.* 279:377-380.

The invention claimed is:

1. A method of treating cancer consisting of administering to a patient in need of the same a conjugate of a cytokine and at least one tumor targeting moiety (TTM) containing the NGR motif, wherein the conjugate is administered in a dosage range of 5-15 ng/kg, and wherein the cytokine is TNFα.

2. The method according to claim 1, wherein the TTM is a tumor vasculature targeting moiety (TVTM).

3. The method according to claim 2, wherein the TVTM is a binding partner of a tumor vasculature receptor, marker or other extracellular component.

4. The method according to claim 1, wherein the TTM is a binding partner of a tumor receptor, marker or other extracellular component.

5. The method according to claim 1, wherein the TTM is targeted to aminopeptidase N (CD13).

6. The method according to claim 1, wherein the TTM is CNGRCVSGCAGRC (SEQ ID NO: 1), NGRAHA (SEQ ID NO: 2), GNGRG (SEQ ID NO: 3), cycloCVLNGRMEC (SEQ ID NO: 4), linear or cyclic CNGRC (SEQ ID NO: 5).

7. The method according to claim 1, wherein the cytokine is linked to the TTM through a spacer.

8. The method according to claim 1, wherein the TTM is CNGRC (SEQ ID NO: 5) and wherein the amino terminal of TNFα is linked to the CNGRC peptide (SEQ ID NO: 5) through the spacer G (glycine).

9. The method according to claim 1, wherein the conjugate is in the form of a fusion protein.

10. A method of treating cancer consisting of administering to a patient in need of the same at least one cytotoxic drug in combination with a conjugate of TNFα and at least one tumor targeting moiety (TTM) containing the NGR motif, wherein the conjugate is administered in a dosage range of 5-15 ng/kg.

11. The method according to claim 10, wherein the cytotoxic drug is doxorubicin, melphalan, or cisplatin.

12. A method of treating cancer comprising administering to a patient in need of the same a cytokine, wherein the only cytokine administered to the patient consists of TNFα conjugated to at least one tumor targeting moiety (TTM) containing the NGR motif, and wherein the cytokine is administered in a dosage range of 5-15 ng/kg.

13. The method according to claim 12, wherein the TTM is CNGRC (SEQ ID NO: 5) and wherein the amino terminal of TNFα is linked to the CNGRC peptide (SEQ ID NO: 5) through the spacer G (glycine).

14. In a method of treating a patient with cancer that includes administering to the patient a cytokine, the improvement wherein the only cytokine that is administered to the patient consists of TNFα conjugated to at least one tumor targeting moiety (TTM) containing an NGR motif, and wherein the cytokine is administered to the patient in a dosage range of 5-15 ng/kg.

15. The method of claim 14, further comprising administering to the patient a cytoxic drug selected from doxorubicin, melphalan, and cisplatin.

* * * * *